(12) United States Patent
Shyu et al.

(10) Patent No.: US 11,529,373 B2
(45) Date of Patent: Dec. 20, 2022

(54) METHOD FOR ENHANCING EXPRESSION OF INSULIN LIKE GROWTH FACTOR 1 RECEPTOR IN MESENCHYMAL STEM CELL, METHOD FOR OBTAINING MESENCHYMAL STEM CELL, AND METHOD FOR TREATING BRAIN TISSUE DAMAGE

(71) Applicant: China Medical University, Taichung (TW)

(72) Inventors: Woei-Cherng Shyu, Taichung (TW); Chen-Huan Lin, Taichung (TW); Wei Lee, Taipei (TW); Chia-Hung Hsieh, Taichung (TW); Chung-Y. Hsu, Taichung (TW); Chang-Hai Tsai, Taichung (TW)

(73) Assignee: China Medical University, Taichung (TW)

( * ) Notice: Subject to any disclaimer, the term of this patent is extended or adjusted under 35 U.S.C. 154(b) by 296 days.

(21) Appl. No.: 16/835,771

(22) Filed: Mar. 31, 2020

(65) Prior Publication Data
US 2020/0246388 A1    Aug. 6, 2020

Related U.S. Application Data

(62) Division of application No. 15/853,989, filed on Dec. 26, 2017, now Pat. No. 10,660,918, which is a division of application No. 14/934,162, filed on Nov. 6, 2015, now abandoned.

(30) Foreign Application Priority Data

Jul. 22, 2015   (TW) ................. 104123719

(51) Int. Cl.
| | | |
|---|---|---|
| *A61K 35/28* | (2015.01) | |
| *C12N 5/073* | (2010.01) | |
| *C12N 5/0775* | (2010.01) | |
| *A61K 38/17* | (2006.01) | |
| *A61P 25/28* | (2006.01) | |
| *A61K 38/18* | (2006.01) | |
| *A61K 45/06* | (2006.01) | |
| *A61K 35/12* | (2015.01) | |

(52) U.S. Cl.
CPC ............ *A61K 35/28* (2013.01); *A61K 38/179* (2013.01); *A61K 38/1858* (2013.01); *A61P 25/28* (2018.01); *C12N 5/0605* (2013.01); *C12N 5/0665* (2013.01); *C12N 5/0668* (2013.01); *A61K 45/06* (2013.01); *A61K 2035/124* (2013.01); *C12N 2500/84* (2013.01)

(58) Field of Classification Search
CPC .. A61K 35/28; A61K 38/179; A61K 38/1858; A61K 45/06; A61P 25/28; C12N 5/0605; C12N 5/0668; C12N 2500/84
See application file for complete search history.

(56) References Cited

U.S. PATENT DOCUMENTS

2008/0131405 A1    6/2008   Jeun

FOREIGN PATENT DOCUMENTS

| CN | 101642469 A | 2/2010 |
|---|---|---|
| CN | 101690731 A | 4/2010 |
| JP | 2009153514 A | 7/2009 |
| JP | 2010511381 A | 4/2010 |
| WO | 2008066330 A1 | 6/2008 |
| WO | 2008085564 A2 | 7/2008 |

OTHER PUBLICATIONS

Nagamura-Inoue et al. Umbilical cord-derived mesenchymal stem cells: Their advantages and potential clinical utility. World J Stem Cells Apr. 26, 2014; 6(2): 195-202 (Year: 2014).*
"Transplantation of human umbilical cord mesenchymal stem cells at different gestational age for myocradium revascularization after myocardial infarction", 14 pgs.
Ding, Dah-Ching , et al., "Enhancement of neuroplasticity through upregulation of β1-integrin in human umbilical cord-derived stromal cell implanted stroke model", Neurobiology of Disease, published in Sep. 2007, vol. 27, issue 3, pp. 339-353, published by Elsevier Inc., United States.
El-Sherbiny, Yasser , et al., "IL-22 Drives the Proliferation and Differentiation of Human Bone Marrow Mesenchymal Stem Cells (MSCs); A Novel Pathway That May Contribute to Aberrant New Bone Formation in Human Spa and Beyond", 2015 ACR/ARHP Annual Meeting, dated on Nov. 9, 2015, abstract No. 1377, poster, United States.
Granero-Molto, Froilan , et al., "Mesenchymal Stem Cells Expressing Insulin-like Growth Factor-I (MSCIGF) Promote Fracture Healing and Restore New Bone Formation in Irs1 Knock-out Mice: Analyses of MSCIGF Autocrine and Paracrine Regenerative Effects", Stem Cells, published in Oct. 2011, vol. 29, issue 10, pp. 1537-1548, published by AlphaMed Press, United States.
Julavijitphong, Suphakde , et al., "Axeno-free culture method that enhances Wharton's jelly mesenchymal stromal cell culture efficiency over traditional animal serum-supplemented cultures", Cytotherapy, 16, 2014, 683-691.
Lin, Yu-Ching , et al., "Human Umbilical Mesenchymal Stem Cells Promote Recovery After Ischemic Stroke", Stroke, published in Jul. 2011, vol. 42, issue 7, pp. 2045-2053, published by American Heart Association, Inc., United States.
Liu, Shih-Ping , et al., "Nonsenescent Hsp27-Upregulated MSCs Implantation Promotes Neuroplasticity in Stroke Model", Cell Transplantation, published on Oct. 1, 2010, vol. 19, issue 10, pp. 1261-1279, published by SAGE Publishing, United States.

(Continued)

*Primary Examiner* — Taeyoon Kim

(57) ABSTRACT

A method for enhancing an expression of insulin like growth factor 1 receptor in a mesenchymal stem cell is provided. The method includes culturing the mesenchymal stem cell expressing insulin-like growth factor 1 receptor in a medium containing platelet-derived growth factor BB (PDGF-BB) to enhance the expression of insulin like growth factor 1 receptor in the mesenchymal stem cell.

4 Claims, 48 Drawing Sheets
(13 of 48 Drawing Sheet(s) Filed in Color)

(56) References Cited

OTHER PUBLICATIONS

Malgieri, Arianna, et al., "Bone marrow and umbilical cord blood human mesenchymal stem cells: state of the art", International Journal of Clinical and Experimental Medicine, published in 2010, vol. 3, No. 4, pp. 248-269, published by e-Century Publishing Corporation, United States.

Murphy, Matthew J., et al., "Adult and umbilical cord blood-derived platelet-rich plasma for mesenchymal stem cell proliferation, chemotaxis, and cryo-preservation", Biomaterials 33, 2012, 5308-5316.

Shetty, P., et al., "Human umbilical cord blood serum can replace fetal bovine serum in the culture of mesenchymal stem cells", Cell Biology International, published in Mar. 2007, vol. 31, issue 3, pp. 293-298, published by Portland Press, United Kingdom.

Weiss, Mark L., et al., "Human Umbilical Cord Matrix Stem Cells: Preliminary Characterization and Effect of Transplantation in a Rodent Model of Parkinson's Disease", Stem Cells, published in Mar. 2006, vol. 24, issue 3, pp. 781-792, published by AlphaMed Press, United States.

Wu, Li-Ping, et al., Transplantation of human umbilical cord mesenchymal stem cells at different gestational age for myocardium revascularization after myocardial infarction, "Chinese Journal of Tissue Engineering", Research, published Dec. 3, 2013, vol. 17, No. 49, p. 8521 left-hand column paragraph 2 and 6, p. 8521 right-hand column para. 4 and p. 8525 left-hand column paragraph 3, published by the Journal of Tissue Engineering Research, China.

Wu, Li-Ping, et al., "Transplantation of human umbilical cord mesenchymal stem cells at different gestational age for myocradium revascularization after myocardial infarction", Chinese Journal of Tissue Engineering Research, vol. 17, No. 49, Dec. 3, 2013, 14 pgs.

Youssef, Amer, et al., "Low-Oxygen Tension and IGF-I Promote Proliferation and Multipotency of Placental Mesenchymal Stem Cells (PMSCs) from Different Gestations via Distinct Signaling Pathways", Endocrinology, published on Apr. 1, 2014, vol. 155, issue 4, pp. 1386-1397, published by Oxford University Press, United Kingdom.

Youssef, Amer, et al., "The Roles of Insulin-Like Growth Factors in Mesenchymal Stem Cell Niche", Stem Cells International, published on Feb. 16, 2017, vol. 2017, article ID 9453108, pp. 1-12, published by Hindawi Publishing Corporation, Egypt.

* cited by examiner

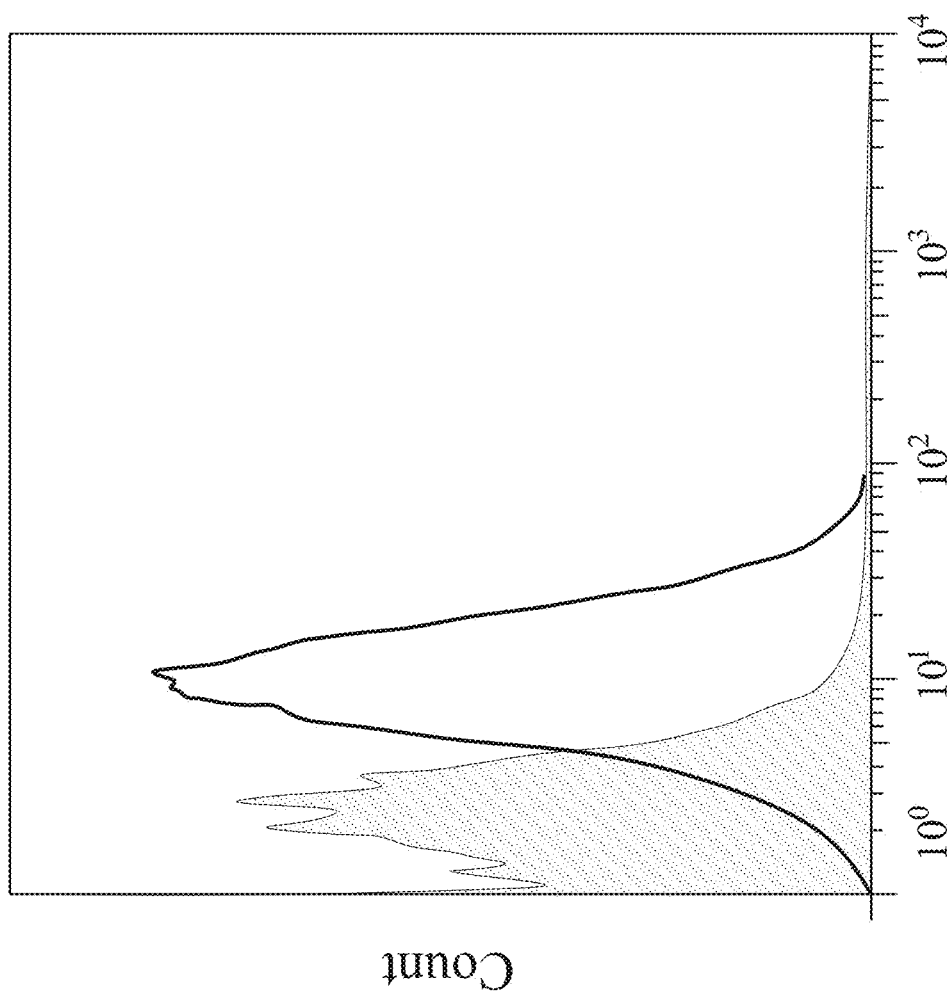

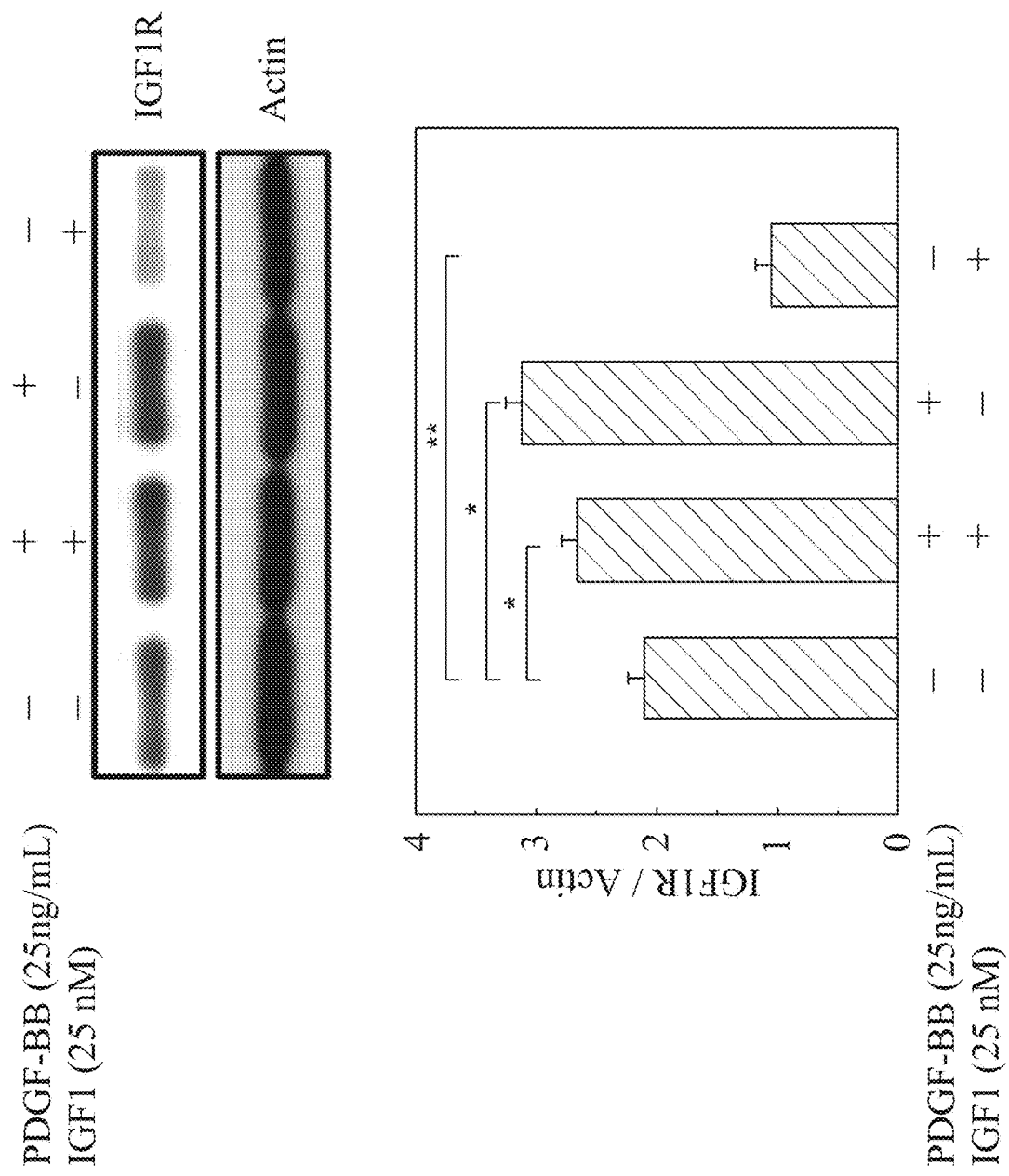

METHOD FOR ENHANCING EXPRESSION OF INSULIN LIKE GROWTH FACTOR 1 RECEPTOR IN MESENCHYMAL STEM CELL, METHOD FOR OBTAINING MESENCHYMAL STEM CELL, AND METHOD FOR TREATING BRAIN TISSUE DAMAGE

RELATED APPLICATIONS

The present application is a Divisional Application of the application Ser. No. 15/853,989, filed Dec. 26, 2017, which is a Divisional Application of the application Ser. No. 14/934,162, filed Nov. 6, 2015, and claims priority to Taiwan Application Serial Number 104123719, filed Jul. 22, 2015, all of which are herein incorporated by reference.

BACKGROUND

Field of Invention

The present disclosure relates to a mesenchymal stem cell. More particularly, the present disclosure relates to the mesenchymal stem cell expressing a special receptor.

Description of Related Art

Stem cells are undifferentiated biological cells that have abilities to duplicate and self-renew for long periods of time and differentiate into mature cells with specialized cell type and function. The stem cells can be classified into embryonic stem cells (ESCs) and adult stem cells according to their origin. The ESCs can be obtained from an inner cell mass of a blastocyst, and the adult stem cells can be obtained from various tissues. The stem cells can be further classified into totipotent stem cells, pluripotent stem cells, and multipotent stem cells according to their pluripotent ability. The totipotent stem cells have a full differentiation capability to develop into a complete embryo or an organism. The pluripotent stem cells have the potential to differentiate into three germ layers and then differentiate into almost any cells in a tissue or an organ, but the pluripotent stem cells are unable to develop into the complete embryo or the organism. The multipotent stem cells are the stem cells of specialized tissues, such as neural stem cells, hematopoietic stem cells, hepatic stem cells, and epidermal stem cells.

Mesenchymal stem cells, a kind of the adult stem cells, belong to multipotent stem cells. Therefore, the mesenchymal stem cells are capable of proliferation and multipotent differentiation; that is, they can differentiate into a variety of mesenchymal tissues such as neurocytes, vascular cells, glial cells, adipocytes or osteocytes. The mesenchymal stem cells can be obtained from the mesenchymal tissues of a bone marrow, an adipose, a dental pulp or an umbilical cord. The mesenchymal stem cells have a tendency ability to differentiate into specific tissues based on their origins of the tissues. Furthermore, when body tissues damage; the mesenchymal stem cells can proceed to repair the damaged tissue directly or indirectly.

The mesenchymal stem cells can be applied for repairing damage of a nerve, a heart, a liver, a lung, a kidney, a bone, a cartilage and a retinal. In recent years, it is also found that the mesenchymal stem cells have the capability of an immune adjustment. As such, the mesenchymal stem cells are potentially used for treating abnormal immune diseases. In addition, since the mesenchymal stem cells have lower antigenicity than that of other stem cells, accurate matching is not required for the mesenchymal stem cells before transplantation, unlike that in the clinical applications of the hematopoietic stem cells. Also, the applications of the mesenchymal stem cells have no ethical concerns as that in the use of ESCs. Therefore, the mesenchymal stem cells are an ideal source of cell treatment. In the clinical applications, the capabilities of self-renew and multipotent differentiation of the mesenchymal stem cells are essential. Accordingly, cell surface receptors associated with pluripotency maintain of the mesenchymal stem cells become one of the main topics in the stem cell medical technology research and development.

SUMMARY

According to one aspect of the present disclosure, a method for enhancing an expression of insulin like growth factor 1 receptor in a mesenchymal stem cell is provided. The method includes culturing the mesenchymal stem cell expressing insulin-like growth factor 1 receptor in a medium containing platelet-derived growth factor BB (PDGF-BB) at 2.5-50 ng/mL to enhance the expression of insulin like growth factor 1 receptor in the mesenchymal stem cell.

In another aspect, a method for obtaining a plurality of multipotent mesenchymal stem cells is provided. The method includes providing a human umbilical cord tissue and performing an isolation step. The isolation step isolates a plurality of cells that express insulin-like growth factor 1 receptor (IGF1R) and CD13, CD29, CD44, CD73, CD90, CD105, CD166, HLA-ABC, Oct-4, Sox-2, Nanog and SSEA-4 from the human umbilical cord tissue to obtain the multipotent IGF1R positive mesenchymal stem cells expressing higher levels of Oct-4, Sox-2, Nanog and SSEA-4, which are the representative markers for the multipotent capability.

In yet another aspect, a method for treating a brain tissue damage is provided. The method includes administering a composition containing a plurality of umbilical cord mesenchymal stem cells to a subject in need for a treatment of the brain tissue damage, wherein the umbilical cord mesenchymal stem cell isolated by using an insulin-like growth factor 1 receptor antibody and then cultured in a medium containing platelet-derived growth factor BB (PDGF-BB) at 2.5-50 ng/mL to enhance the expression of insulin-like growth factor 1 receptor in the mesenchymal stem cell.

BRIEF DESCRIPTION OF THE DRAWINGS

The patent or application file contains at least one drawing executed in color. Copies of this patent or patent application publication with color drawing(s) will be provided by Office upon request and payment of the necessary fee. The present disclosure can be more fully understood by reading the following detailed description of the embodiment, with reference made to the accompanying drawings as follows:

FIG. 1C shows the analytical result of interleukin 22 receptor alpha 1 (IL22RA1) expressions of the MSCs according to one embodiment of the present disclosure;

FIG. 7C shows analytical results of the IGF1R expression and the CXCR4 expression of the MSCs after treating different dose of the IGF1 and the PDGF-BB simultaneously according to one embodiment of the present disclosure;

DETAILED DESCRIPTION

Figure 1A:
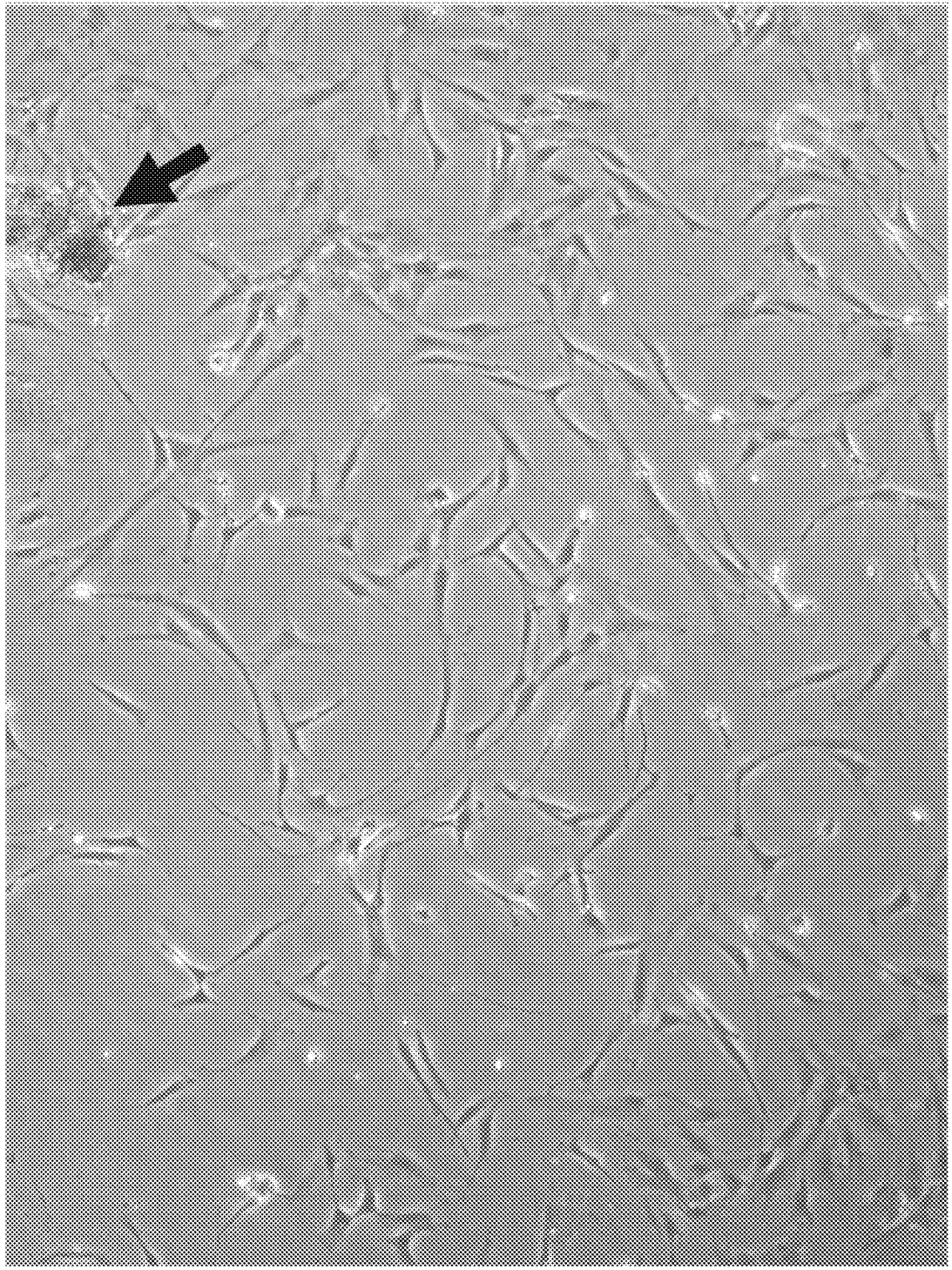
FIG. 1A is a micrograph of a primary cell culture of umbilical mesenchymal stem cells (UMSCs)

A mesenchymal stem cell (MSC) expressing a special cell receptor is provided. The MSC has a self-renewal capability and a multipotent capability. A method for a clonogenic expansion of a plurality of mesenchymal stem cells (MSCs) is also provided. The method can enhance a special cell receptor expression of the MSCs and maintain the multipotent capability of the MSCs. A method for obtaining a plurality of multipotent MSCs is further provided. The method can quickly and specifically screen the MSCs having the multipotent capability from a mammalian tissue cell mixture. Furthermore, uses of the mesenchymal stem cell are provided for treating an ischemic heart disease and a brain tissue damage.

In more details, aforementioned MSC expresses an insulin-like growth factor 1 receptor (IGF1R). The term "IGF1R$^+$ mesenchymal stem cell (IGF1R$^+$ MSCs)" is used in the specification to represent the MSC of the present disclosure. The IGF1R$^+$ MSCs are multipotent. The IGF1R$^+$ MSCs can be human cells; especially the IGF1R$^+$ MSCs can be umbilical cord mesenchymal stem cells (UMSCs). The method for the clonogenic expansion of a plurality of MSCs includes culturing the IGF1R$^+$ MSCs in media containing a human cord blood serum (hUCS). A concentration of the hUCS is 1-10% (v/v); preferably, the concentration of the hUCS is 2% (v/v). The method for obtaining a plurality of the multipotent MSCs includes screening IGF1R positive cells from the mammalian tissue cell mixture to obtain the multipotent MSCs. The method for obtaining a plurality of the multipotent MSCs can further screen interleukin 22 receptor alpha 1 (IL22RA1) positive cells from the mammalian tissue cell mixture to obtain the multipotent MSCs. The mammalian tissue can be selected from the group consisting of a bone marrow, a dental pulp, a placenta, an umbilical cord, an adipose tissue, and combinations thereof.

The IGF1R$^+$ MSCs can be used for treating the ischemic heart disease and the brain tissue damage. In more details, the IGF1R$^+$ MSCs can attenuate post-myocardial infarction (MI) left ventricle (LV) dysfunction, reduce an infarct size after the MI, reduce a fibrosis caused by the MI, and reduce an inflammatory effect on the MI. Therefore, the IGF1R$^+$ MSCs can treat the ischemic heart disease, wherein the ischemic heart disease can be the MI. Furthermore, the IGF1R$^+$ MSCs can increase a glucose metabolic activity of the subject, enhance an angiogenesis of the subject, and augments a neurite regeneration of the subject. The IGF1R$^+$ MSCs have a neuroplasticity effect through IGF1R and C-X-C chemokine receptor type 4 (CXCR4) interactions. Therefore, the IGF1R$^+$ MSCs can treat the brain tissue damage, wherein the brain tissue damage can be a cerebral ischemic disease (such as a stroke) or a neural degenerative disease (such as a Parkinson's disease).

The following are descriptions of the specific terms used in the specification:

The term "IGF1R (insulin-like growth factor 1 receptor)" means a protein found on the surface of human cells, and the IGF1R is a transmembrane receptor that is activated by a hormone called insulin-like growth factor 1 (IGF1). The IGF1R belongs to the large class of tyrosine kinase receptors. The IGF1 is a polypeptide protein hormone similar in molecular structure to insulin. In addition, the IGF1 plays an important role in growths and anabolism of adults.

The term "IL22RA1 (interleukin 22 receptor alpha 1)" means a protein shown to be a receptor for interleukin 22 (IL22). The IL22 is a cytokine having both anti-inflammatory and pro-inflammatory effects, and the IL22 is secreted by a variety of immune cells.

The term "CXCR4 (C-X-C chemokine receptor type 4)" means an alpha-chemokine receptor specific for stromal-derived-factor-1 (SDF-1), a molecule endowed with a potent chemotactic activity for lymphocytes. The CXCR4 is expressed on most body tissues and organs. The CXCR4 is a G protein-coupled receptor (GPCR) composed of 352 amino acids, and the CXCR4 has seven transmembrane structures.

Reference will now be made in detail to the present embodiments of the present disclosure, examples of which are illustrated in the accompanying drawings. Wherever possible, the same reference numbers are used in the drawings and the description to refer to the same or like parts.

EXAMPLES

I. The IGF1R$^+$ MSCs 1.1 Preparation of the IGF1R$^+$ MSCs

To prepare the IGF1R$^+$ MSCs, the mammalian tissues used in this example are human umbilical cord tissues. The UMSCs of the human umbilical cord tissue are stored in Wharton's jellies. The collected human umbilical cord tissues are washed three times with Ca2$^+$ and Mg2$^+$-free PBS (DPBS, Life Technology). The human umbilical cord tissues are mechanically cut by scissors in a midline direction and the vessels of the umbilical artery, vein and outlining membrane are dissociated from the Wharton's jelly. The Wharton's jelly is then extensively cut into pieces smaller than 0.5 cm$^3$, treated with collagenase type 1 (Sigma), and then incubated for 14-18 hours at 37° C. in a 95% air/5% CO$_2$ humidified atmosphere. Explants then are cultured in DMEM containing 2% hUCS or 10% fetal calf serum (FCS) and antibiotics at 37° C. in a 95% air/5% CO$_2$ humidified atmosphere. They are left undisturbed for 5-7 days to allow for migration of the cells from the explants.

FIG. 1A is a micrograph of primary cell culture of the UMSCs, wherein the black arrow indicates the explant. In FIG. 1A, the cells migrate from the explants, and a cellular morphology of the cells becomes homogenously spindle shaped in cultures after 4-8 passages.

The specific surface molecules of the cells from the Wharton's jelly are characterized by a flow cytometric analysis. The specific surface molecules detected in this example are the IGF1R, the IL22RA1, Wharton's jelly specific cell surface molecules, and pluripotent markers. The Wharton's jelly specific cell surface molecules include CD13, CD29, CD34, CD44, CD45, CD73, CD90, CD105, CD117, CD166, HLA-ABC, and HLA-DR. The pluripotent markers include Oct-4, Sox-2, Nanog, and SSEA-4.

Figure 1B:
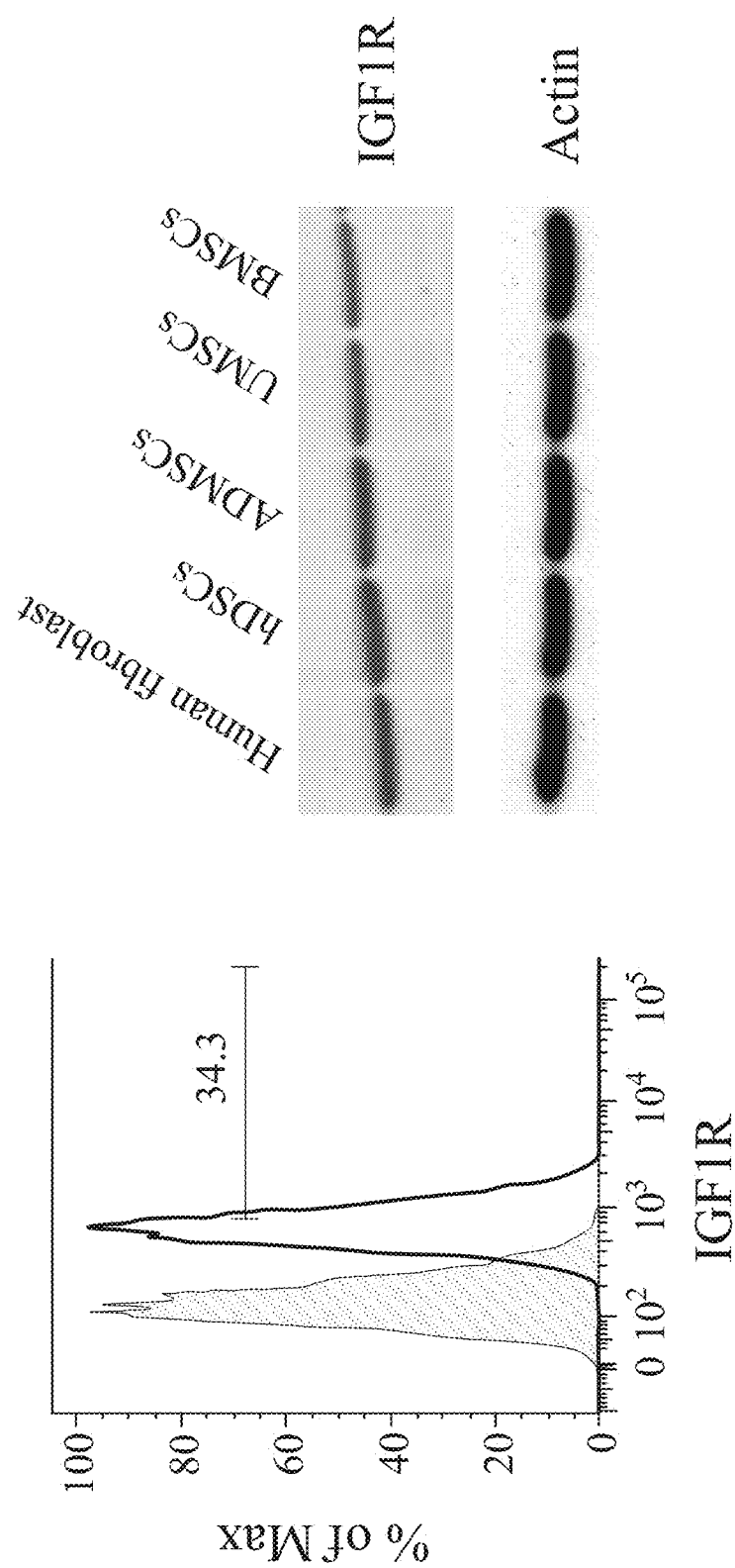
FIG. 1B shows analytical results of insulin-like growth factor 1 receptor (IGF1R) expressions of mesenchymal stem cells (MSCs) according to one embodiment of the present disclosure.
Figure 1D:
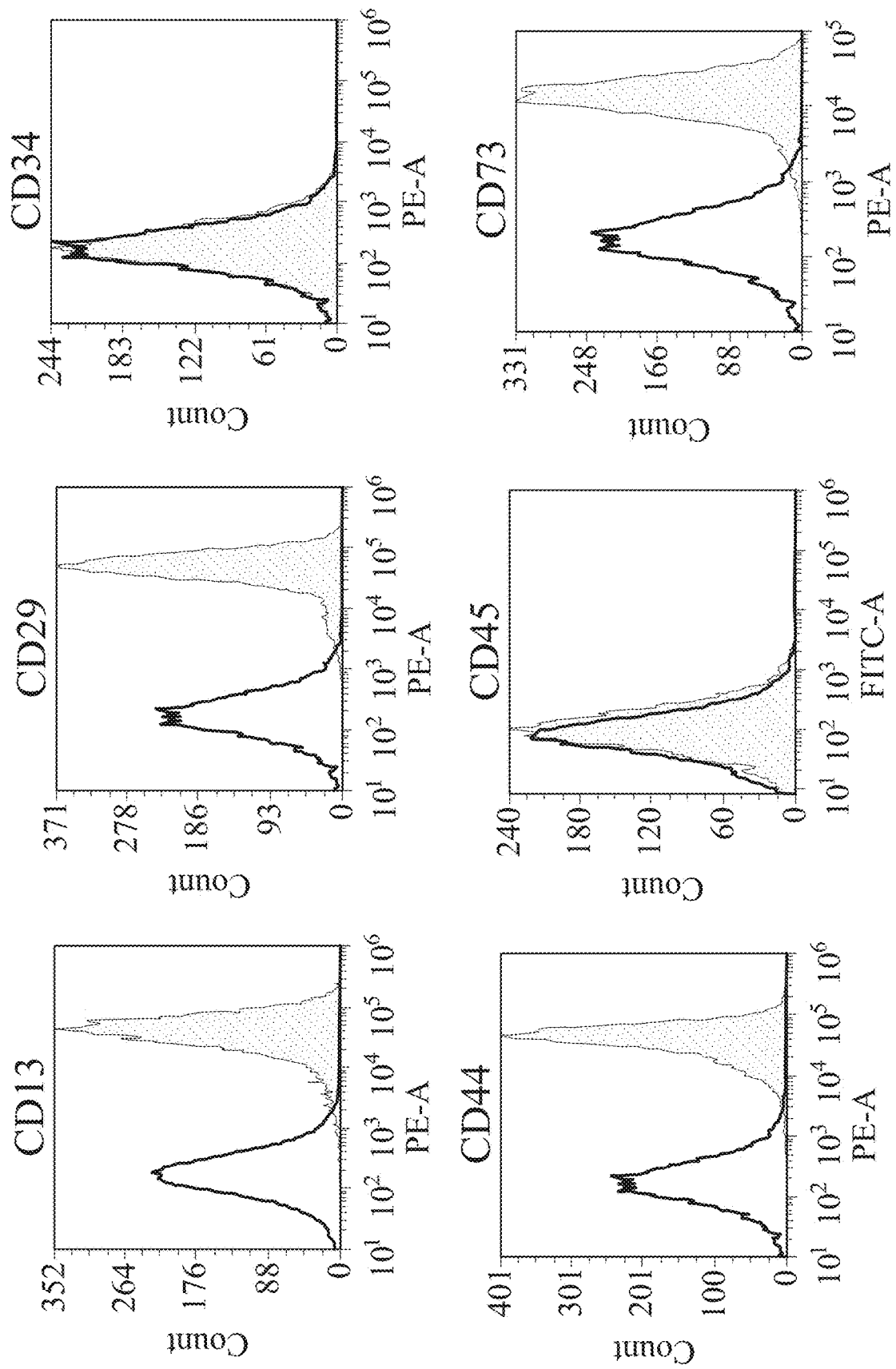
FIGS. 1D and 1E is a set of histograms of FACS (fluorescence-activated cell sorting) analysis showing Wharton's jelly specific cell surface molecules expressions of the MSCs according to one embodiment of the present disclosure.
Figure 1E:
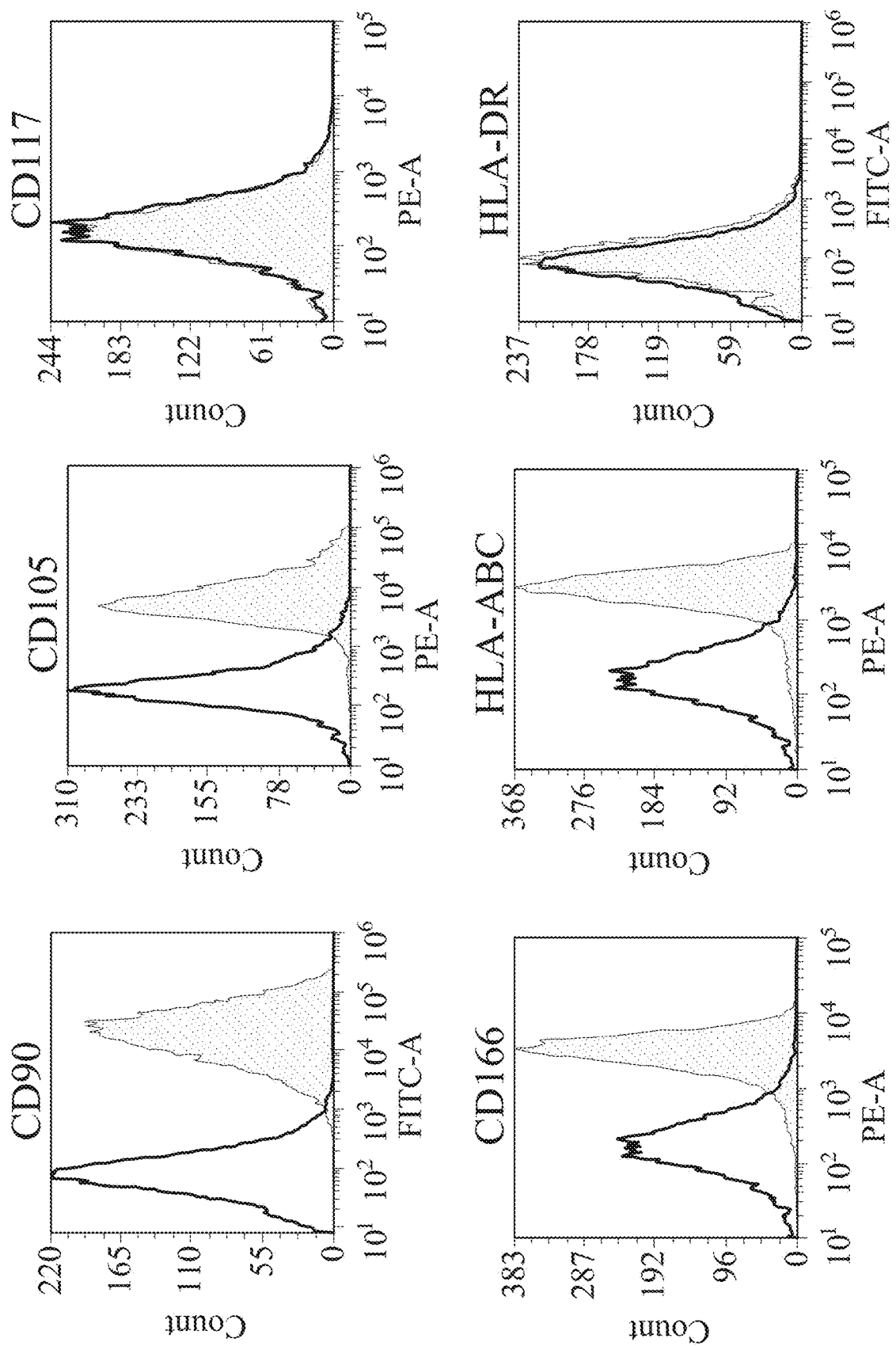
Figure 1F:
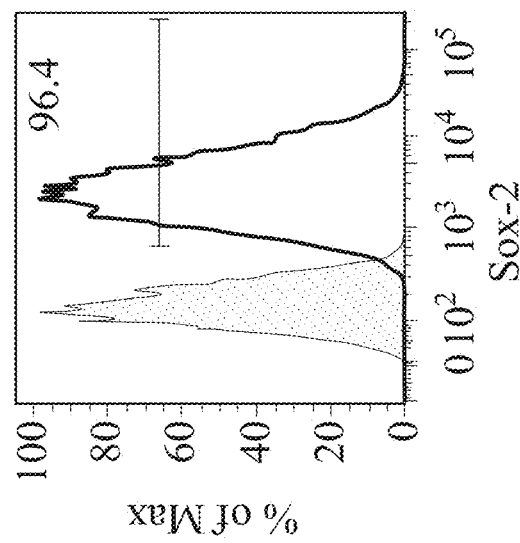
FIG. 1F shows analytical results of pluripotent markers expressions of the MSCs according to one embodiment of the present disclosure.
Figure 1F:
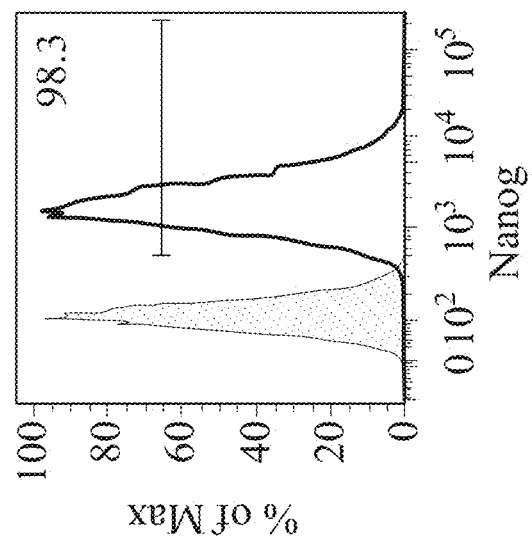
Figure 1F:
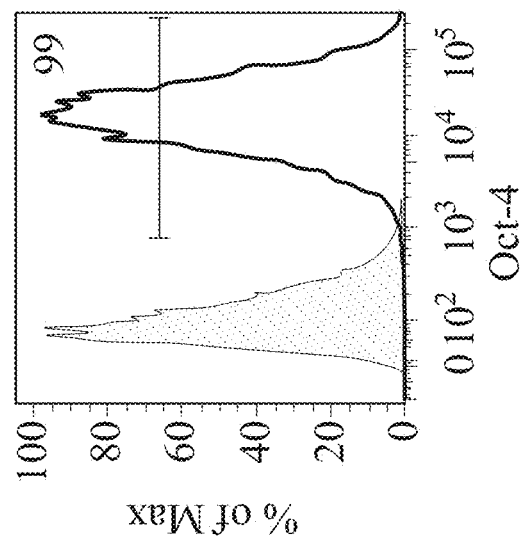
Figure 1F:
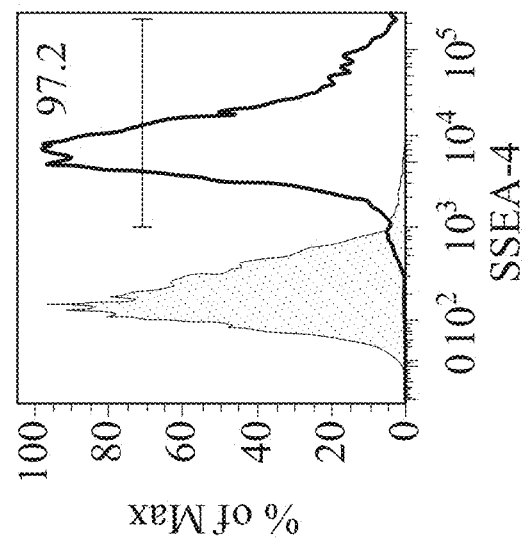

FIG. 1B shows analytical results of the IGF1R expressions of the IGF1R$^+$ MSCs. FIG. 1C shows the analytical result of interleukin 22 receptor alpha 1 (IL22RA1) expressions of the IGF1R$^+$ MSCs. FIGS. 1D and 1E is a set of histograms of FACS (fluorescence-activated cell sorting) analysis showing Wharton's jelly specific cell surface molecules expressions of the IGF1R$^+$ MSCs. FIG. 1F shows the analytical results of pluripotent markers expressions of the IGF1R$^+$ MSCs.

In FIG. 1B, we first detect the IGF1R expression on the cells from the Wharton's jelly by the flow cytometric analysis, and then detect the IGF1R expression on the MSCs form different tissues by a Western blotting analysis. The MSCs analyzed in the Western blotting analysis are human fibroblasts, human decidua-derived stem cells (hDSCs), human adipose derived stem cells (ADSCs), the UMSCs, and human bone marrow stromal cell (BMSC). Based on the analytical results, the cells from the Wharton's jelly (UM- SCs) express the surface markers of the IGF1R, which shows consensus expression in the BMSCs, ADMSCs, and hDSCs.

In FIGS. 1C-1F, IL22RA1, Wharton's jelly specific cell surface molecules and pluripotent markers of the cells from the Wharton's jelly are characterized by the flow cytometric analysis. In FIG. 1C, the cells from the Wharton's jelly express the IL22RA1, and 45.4% cells express the IL22RA1 compared to a control group. In FIGS. 1D and 1E, the cells from the Wharton's jelly express CD13, CD29, CD44, CD73, CD90, CD105, CD166, and HLA-ABC. In addition, the cells from the Wharton's jelly do not express CD34, CD45, CD 117, and HLA-DR. The flow cytometric analysis results indicate that the cells from the Wharton's jelly are a penotype of the MSCs rather than hematopoietic stem cells. In FIG. 1F, the cells from the Wharton's jelly express Oct-4, Sox-2, Nanog, and SSEA-4; those are the pluripotent markers represented the multipotent capability.

Thereafter, the cells are analyzed using a flow cytometer (Becton Dickinson) and then mixed with the insulin-like growth factor 1 receptor antibody. Cells sorting is used to purify the IGF1R$^+$ MSCs (>95% IGF1R) using a FACSTAR$^+$ flow-cytometer (Becton Dickinson). Approximately 96% of the sorted cells are viable, as confirmed by Trypan blue exclusion test.

1.2 Culture of the IGF1R$^+$ MSCs

The sorted IGF1R$^+$ MSCs are cultured in the DMEM containing 2% hUCS or 10% fetal calf serum (FCS) and antibiotics at 37° C. in a 95% air/5% $CO_2$ humidified atmosphere. The IGF1R$^+$ MSCs cultured in 2% hUCS and in 10% FCS are analyzed their growth kinetics.

Figure 2:
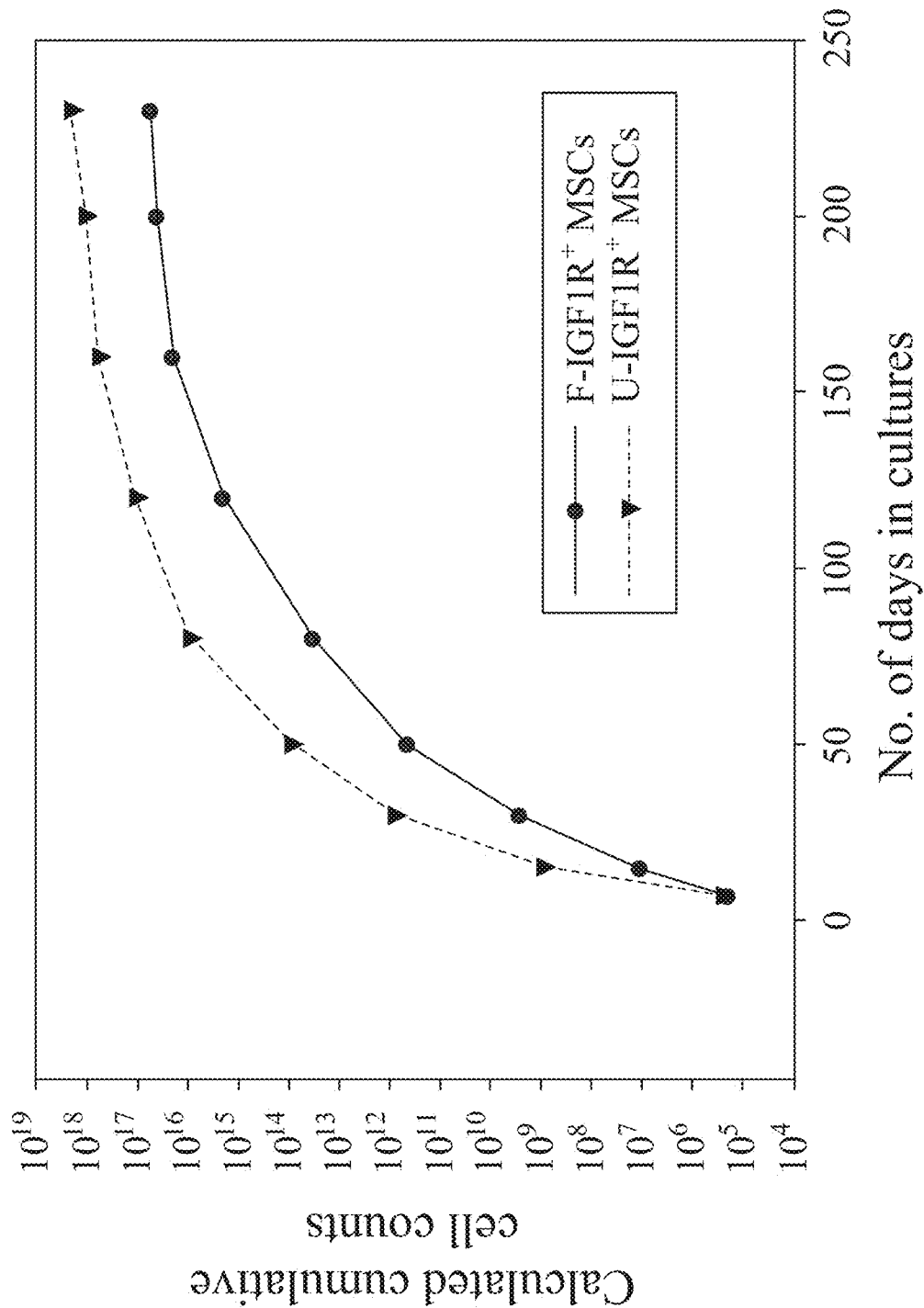
FIG. 2 is an exponential growth curve of the MSCs according to one embodiment of the present disclosure.

FIG. 2 is an exponential growth curve of the IGF1R$^+$ MSCs. In FIG. 2, the hUCS-cultured IGF1R$^+$ MSCs (U-IGF1R$^+$ MSCs) proliferate faster compared to FCS-cultured IGF1R$^+$ MSCs (F-IGF1R$^+$ MSCs). The U-IGF1R$^+$ MSCs grow exponentially with a doubling time of 22 hours and are extensively expanded for more than 150 days without signs of senescence and spontaneous differentiation.

To assess the advantages of using the medium containing the hUCS to culture the IGF1R$^+$ MSCs, we apply a human cytokine array system (RayBiotech) to identify and compare the specific cytokine(s) in the hUCS and the FCS. A total of 42 cytokines are examined in this example, and cytokine expression levels in the hUCS or the FCS are determined by a densitometry.

Figure 3A:
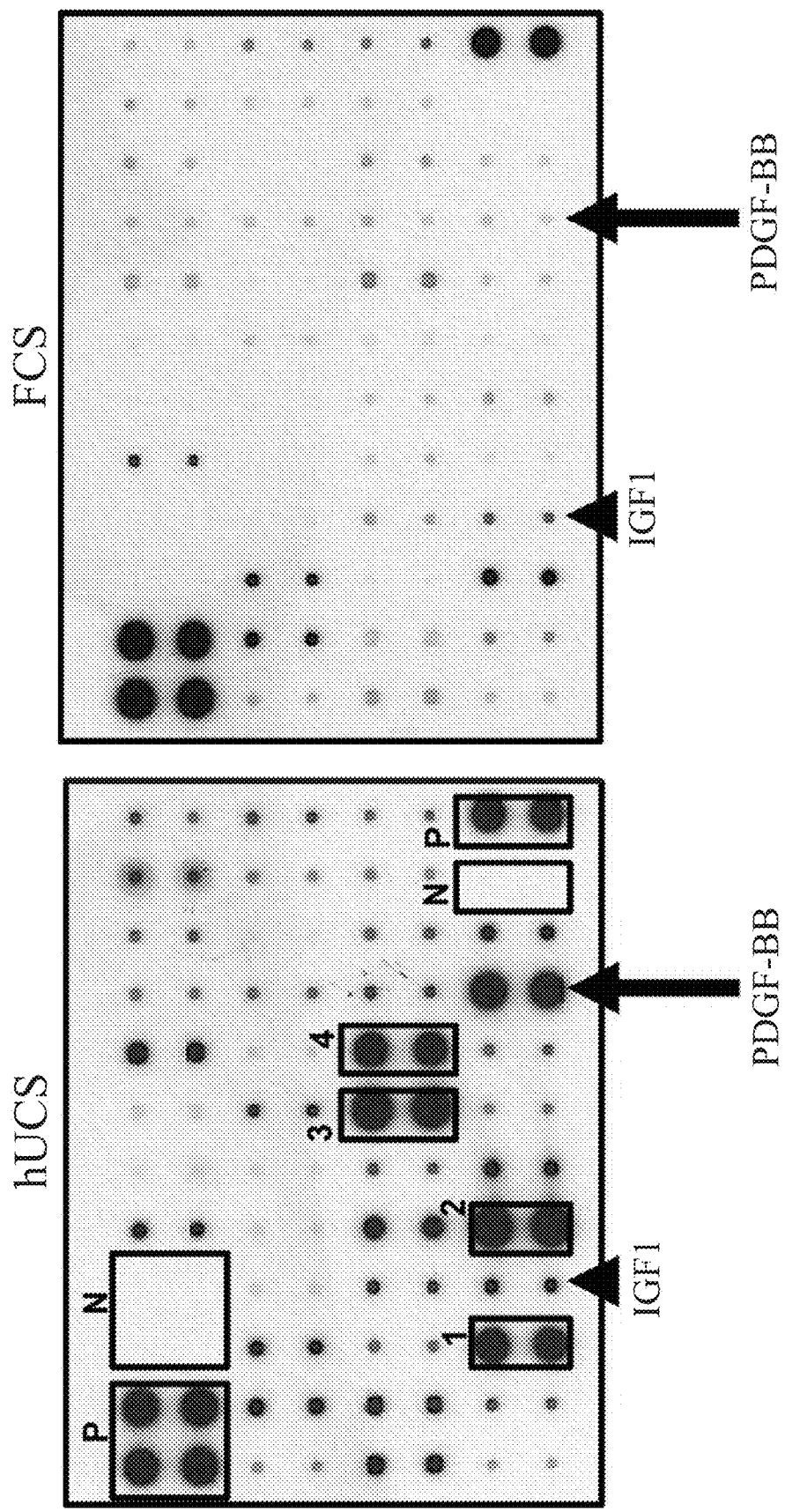
FIG. 3A shows analytical results of human cytokines arrays of a human cord blood serum (hUCS) and a fetal calf serum (FCS)

FIG. 3A shows the analytical results of human cytokines arrays of the hUCS and the FCS, wherein "P" represents a positive control and "N" represents a negative control. In FIG. 3A, expressions levels of five cytokines are significantly higher in the hUCS than in the FCS. These are epidermal growth factor (EGF, square 1), angiogenin (ANG, square 2), macrophage inflammatory protein-5 (MIP-1δ, square 3), regulated on activation, normal T-cell expressed and presumably secreted (RANTES, square 4) and platelet-derived growth factor BB (PDGF-BB). The ratio of differences expression levels of these five cytokines are 2, 3, 3, 2, and 4 times, respectively. In contrast, expression levels of the IGF1 are similar in the hUCS and the FCS.

To more accurately quantify the PDGF-BB and the IGF1 concentration in the hUCS and the FCS, enzyme-linked immunosorbent assay (ELISA) is performed using the hUCS and the FCS samples in this example to analyze the PDGF-BB concentration and the IGF1 concentration.

Figure 3B:
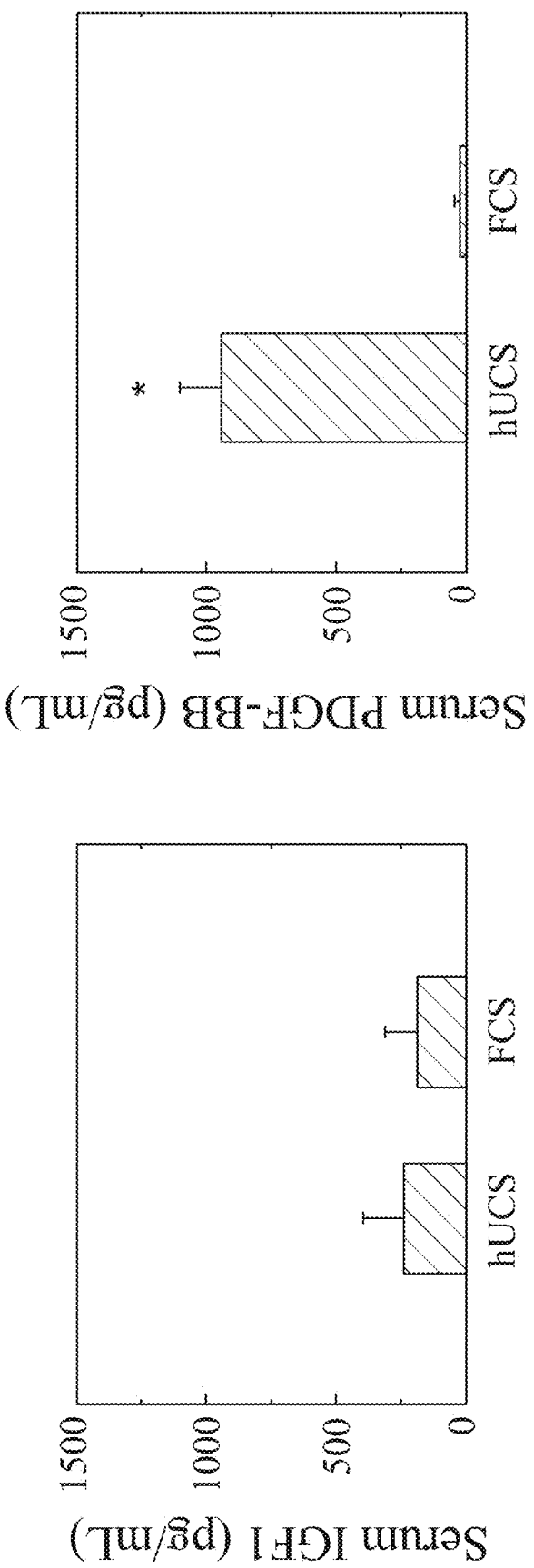
FIG. 3B shows quantitative results of enzyme-linked immunosorbent assay (ELISA) of the hUCS and the FCS.

FIG. 3B shows quantitative results of ELISA of the hUCS and the FCS. In FIG. 3B, the IGF1 expression levels are indistinguishable between the two types of serum, while the PDGF-BB concentration is substantially higher in the hUCS than in the FCS ($p<0.05$).

1.3 The Self-Renewal Capability of the IGF1R$^+$ MSCs

To investigate whether the IGF1R signaling pathway contributes to the regulation of the IGF1R$^+$ MSCs self-renewal capability, we use lentivirus-mediated shRNA targeting of IGFR1R (LV-IGF1R-sh,sc-29358-V, Santa Cruz Biotechnology) to the hUCS-cultured IGF1R$^+$ MSCs (U-IGF1R$^+$ MSCs) or the FCS-cultured IGF1R$^+$ MSCs (F-IGF1R$^+$ MSCs) for knocking down levels of the receptor. We also use lentivirus-mediated control shRNA (LV-control-sh, Santa Cruz Biotechnology) to the U-IGF1R$^+$ MSCs or the F-IGF1R$^+$ MSCs as the control group. After 48 hours lentivirus infection, the IGF1R protein expressions of the infected-IGF1R$^+$ MSCs are detected by the Western blotting analysis. The infected-IGF1R$^+$ MSCs are also analyzed their growth kinetics.

Figure 4A:
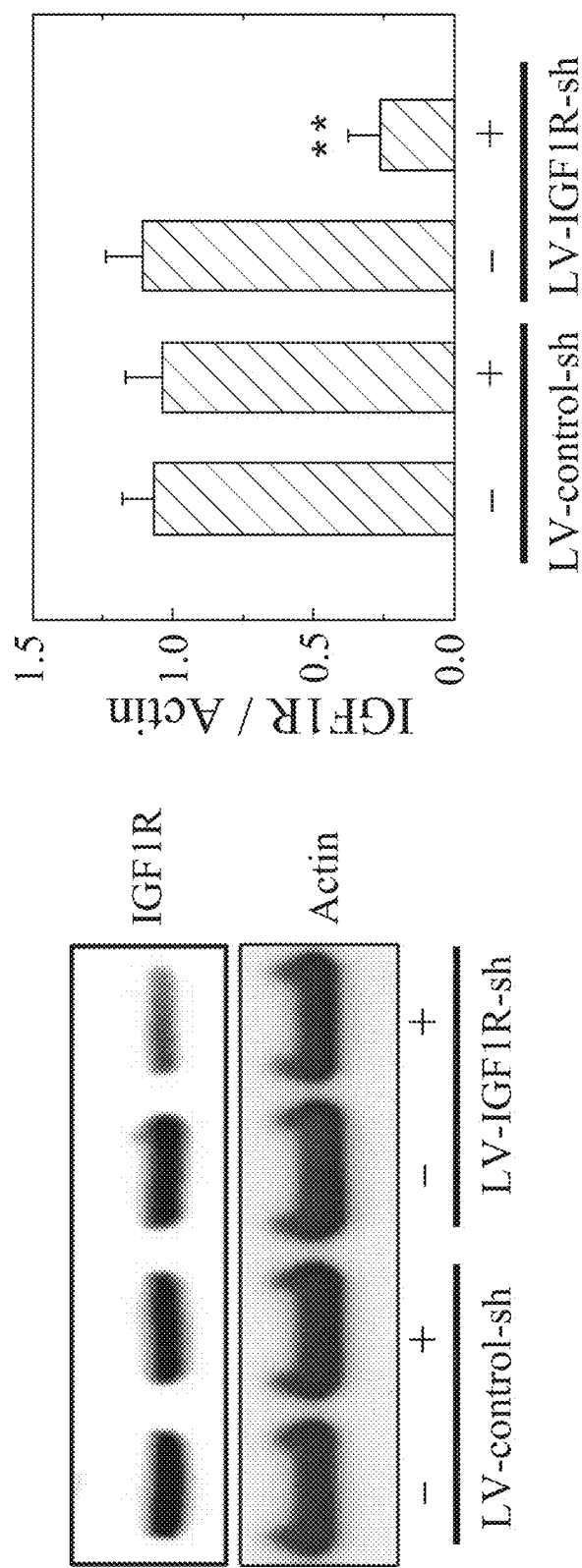
FIG. 4A shows analytical results of the IGF1R expressions of the MSCs after transducing shRNA according to one embodiment of the present disclosure.
Figure 4B:
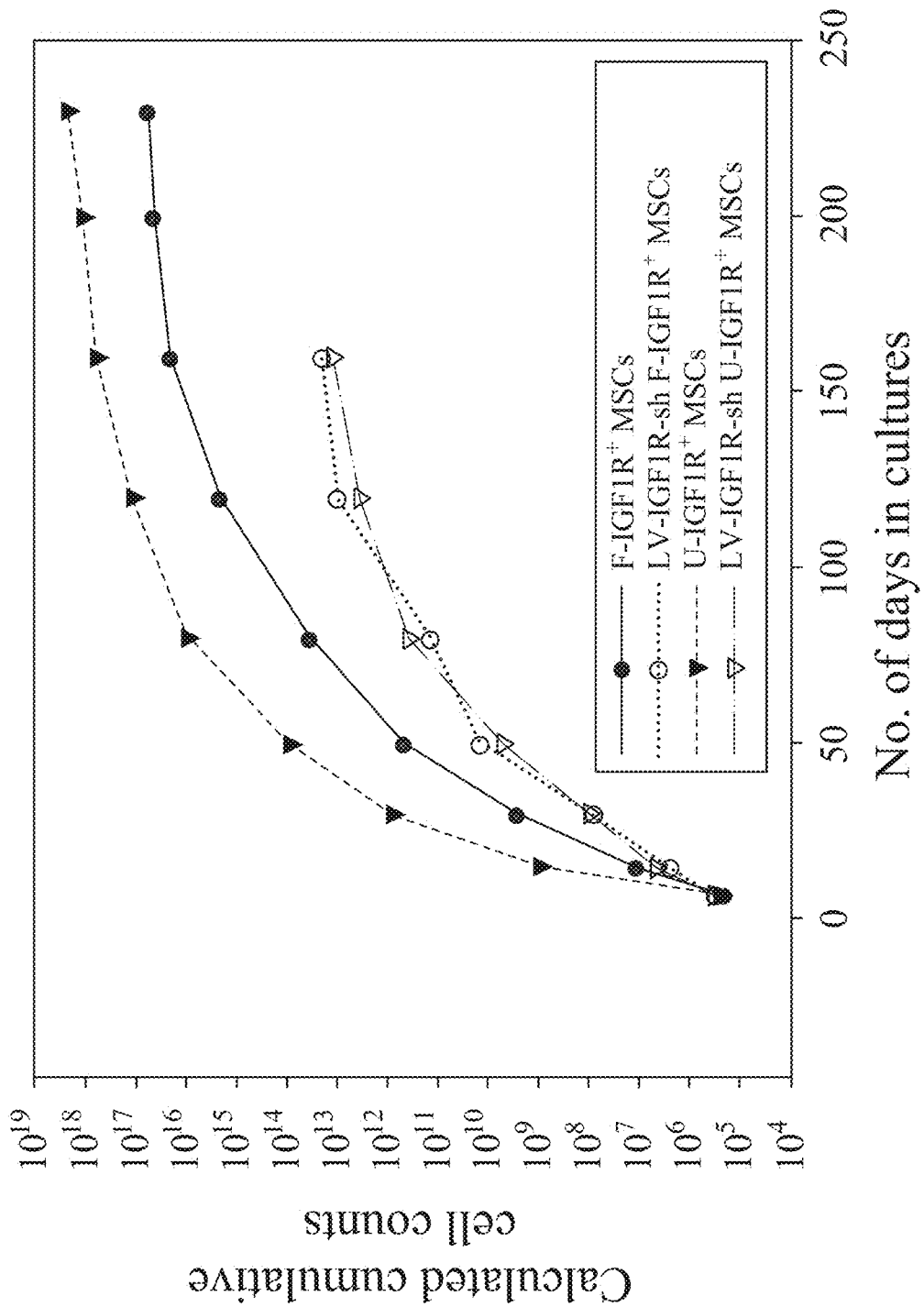
FIG. 4B is an exponential growth curve of the MSCs according to one embodiment of the present disclosure.

FIG. 4A shows the analytical results of the IGF1R expressions of the IGF1R$^+$ MSCs after transducing shRNA. FIG. 4B is the exponential growth curve of the IGF1R$^+$ MSCs. There are four groups in FIG. 4A, the U-IGF1R$^+$ MSCs transduced with or without LV-IGF1R-sh or the U-IGF1R$^+$ MSCs transduced with or without LV-control-sh, wherein all U-IGF1R$^+$ MSCs in FIG. 4A are cultured in the medium containing the hUCS. In FIG. 4A, the group of the IGF1R$^+$ MSCs transduced with LV-IGF1R-sh exhibits a significant reduction in the IGF1R protein expression 48 hours post-infection compared with the group transduced with LV-control-sh, while the IGF1R pretein expression are equivalent in other groups. There are four groups in FIG. 4B, the IGF1R$^+$ MSCs cultured in the medium containing the hUCS and transduced with the LV-control-sh (LV-control-sh U-IGF1R$^+$ MSCs), the IGF1R$^+$ MSCs cultured in the medium containing the FCS and transduced with the LV-control-sh (LV-control-sh F-IGF1R$^+$ MSCs), the IGF1R$^+$ MSCs cultured in the medium containing the hUCS and transduced with the LV-IGF1R-sh (LV-IGF1R-sh U-IGF1R$^+$ MSCs), and the IGF1R$^+$ MSCs cultured in the medium containing the FCS and transduced with the LV-IGF1R-sh (LV-IGF1R-sh F-IGF1R$^+$ MSCs), respectively. In FIG. 4B, the growth kinetic shows that the LV-IGF1R-sh U-IGF1R$^+$ MSCs and the LV-IGF1R-sh F-IGF1R$^+$ MSCs proliferate more slowly than the LV-control-sh U-IGF1R$^+$ MSCs and the LV-control-sh F-IGF1R$^+$ MSCs. It indicates that the LV-IGF1R-sh transduction reduces the proliferation of the IGF1R$^+$ MSCs.

To further evaluate the IGF1R$^+$ MSCs proliferation potential, we use Bromodeoxyuridine (BrdU) to label DNA and perform BrdU chemiluminescence ELISAs in this example. After a 4-6 hours starvation (incubation in the medium lacking supplements), the IGF1R$^+$ MSCs are incubated in the medium containing 10% FCS or 2% hUCS with supplement or the SDF-1α (100 ng/mL, positive control) for 2 days and then transduced with the LV-control-sh or the LV-IGF1R-sh. The proliferation of the IGF1R$^+$ MSCs are tested by measuring BrdU incorporation using a BrdU chemiluminescence immunoassay kits (Roche), and further confirmed by counting Trypan blue cell.

Figure 4C:
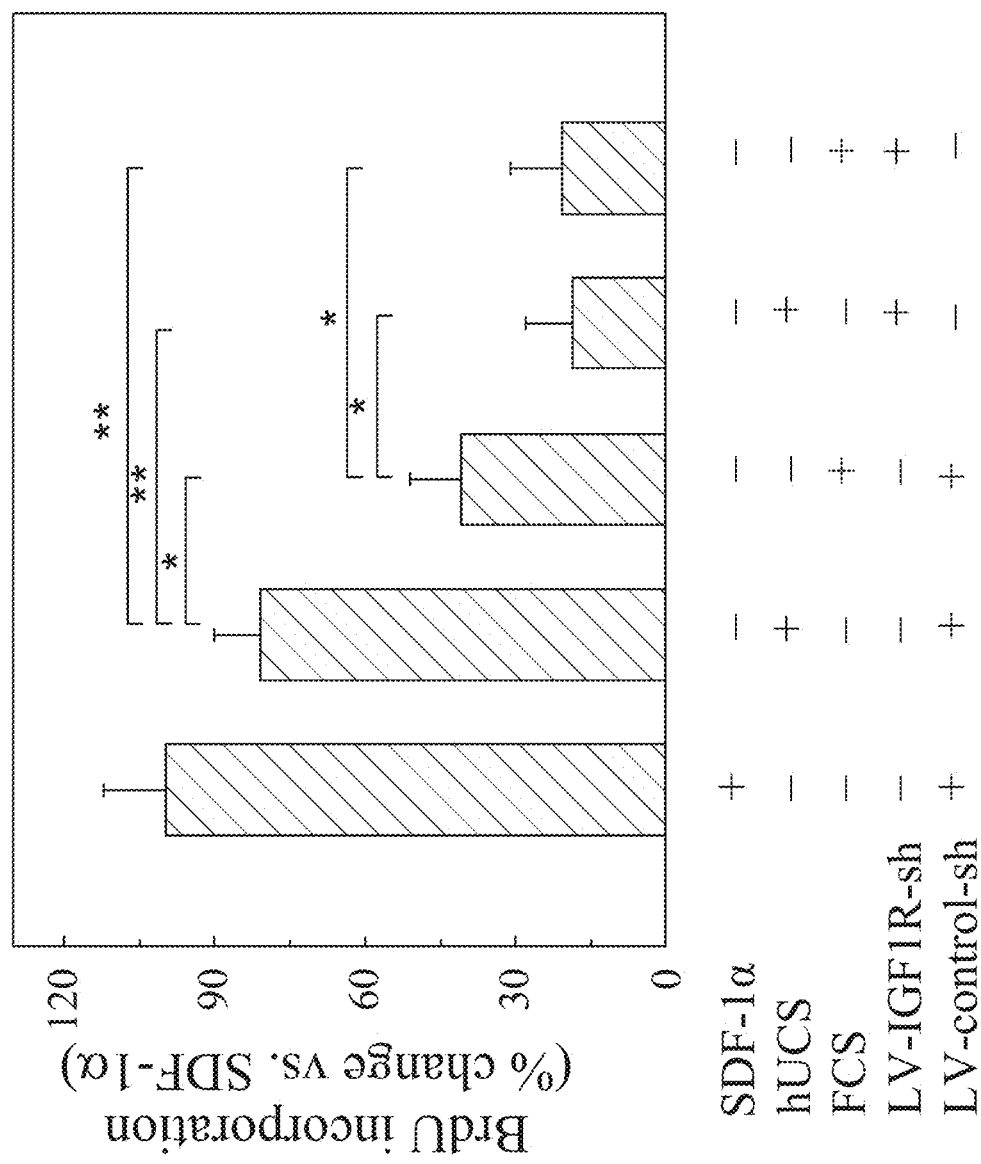
FIG. 4C is quantitative results of BrdU chemiluminescence ELISAs of the MSCs according to one embodiment of the present disclosure.

FIG. 4C is the quantitative results of BrdU chemiluminescence ELISAs of the IGF1R$^+$ MSCs. There are five groups in FIG. 4C, the IGF1R$^+$ MSCs cultured in the medium containing the SDF-1α as the positive control, the IGF1R$^+$ MSCs cultured in the medium containing the hUCS and transduced with the LV-control-sh, the IGF1R+ MSCs cultured in the medium containing the FCS and transduced with the LV-control-sh, the IGF1R+ MSCs cultured in the medium containing the hUCS and transduced with the LV-IGF1R-sh, and the IGF1R+ MSCs cultured in the medium containing the FCS and transduced with the LV-IGF1R-sh, respectively. In FIG. 4C, the IGF1R+ MSCs cultured in the hUCS show significant higher BrdU incorporation compared to the IGF1R+ MSCs cultured in the FCS. In contrast, the LV-IGF1R-sh transductions abolish the BrdU incorporation in the IGF1R+ MSCs cultured in either the hUCS or the FCS. It indicates that the IGF1R is essential for the IGF1R+ MSCs proliferation.

1.4 The Multipotent Capability of the IGF1R+ MSCs

To investigate whether the multipotent capability of the IGF1R+ MSCs is related to the IGF1R, we perform FACS double staining analysis and an immunofluorescent double staining assay. The IGF1R+ MSCs are stained with IGF1R/Oct-4 antibodies, IGF1R/Sox-2 antibodies, IGF1R/Nanog antibodies, and IGF1R/SSEA4 antibodies, respectively. The stained IGF1R+ MSCs are measured co-expressions between the IGF1R and the pluripotent markers using the flow cytometer and the immunofluorescent double staining assay.

Figure 5A:
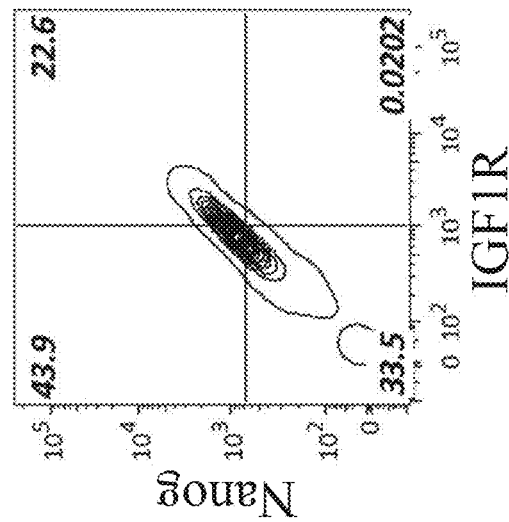
FIG. 5A is a set of histograms of FACS double staining analysis of the MSCs according to one embodiment of the present disclosure.
Figure 5A:
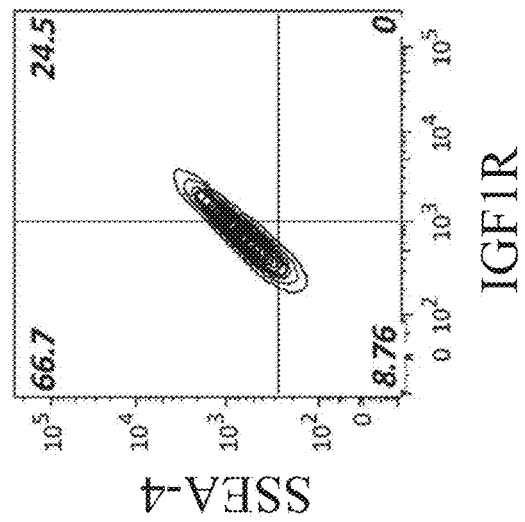
Figure 5A:
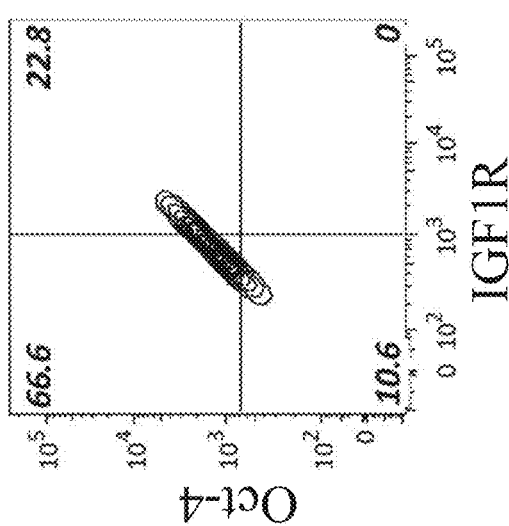
Figure 5A:
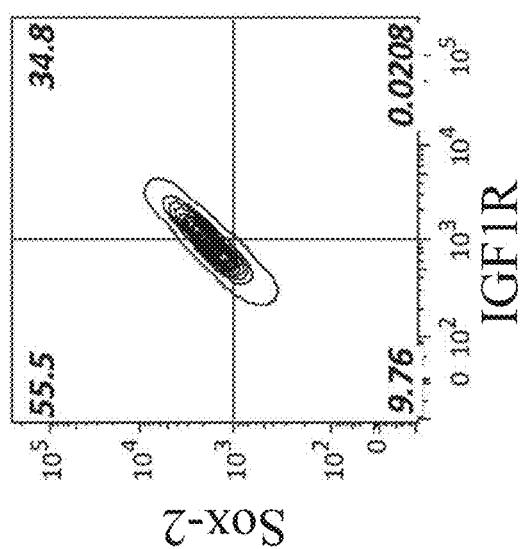
Figure 5B:
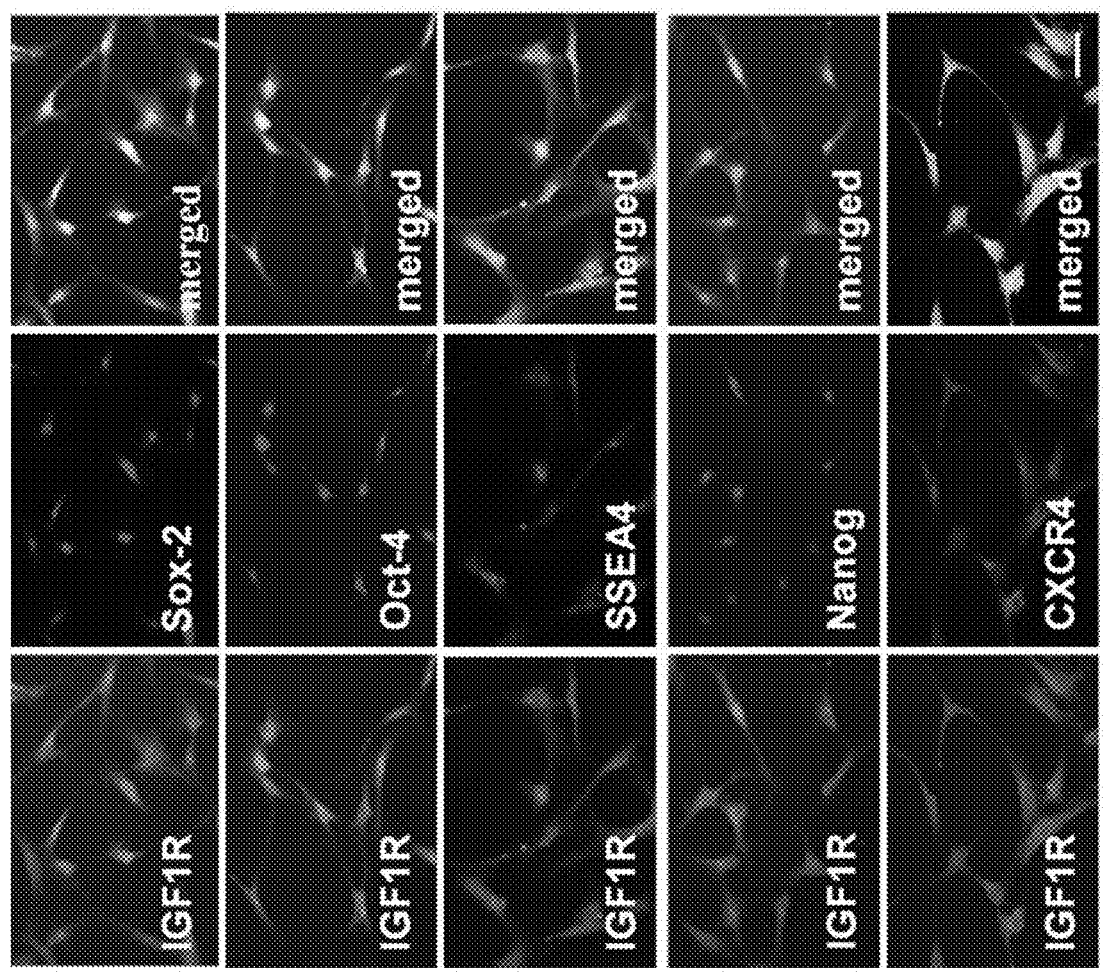
FIG. 5B is a micrograph of an immunofluorescence double staining assay of the MSCs according to one embodiment of the present disclosure.

FIG. 5A is a set of histograms of FACS double staining analysis of the IGF1R+ MSCs. FIG. 5B is a micrograph of Immunofluorescence double staining assay of the IGF1R+ MSCs, wherein the IGF1R+ MSCs are obtained from five independent samples. In FIGS. 5A and 5B, the results reveal that the IGF1R is co-expressed with the pluripotent markers of Oct-4, Sox-2, Nanog and SSEA-4. In FIG. 5B, the results further reveal that the IGF1R is co-expressed with the CXCR4.

Figure 5C:
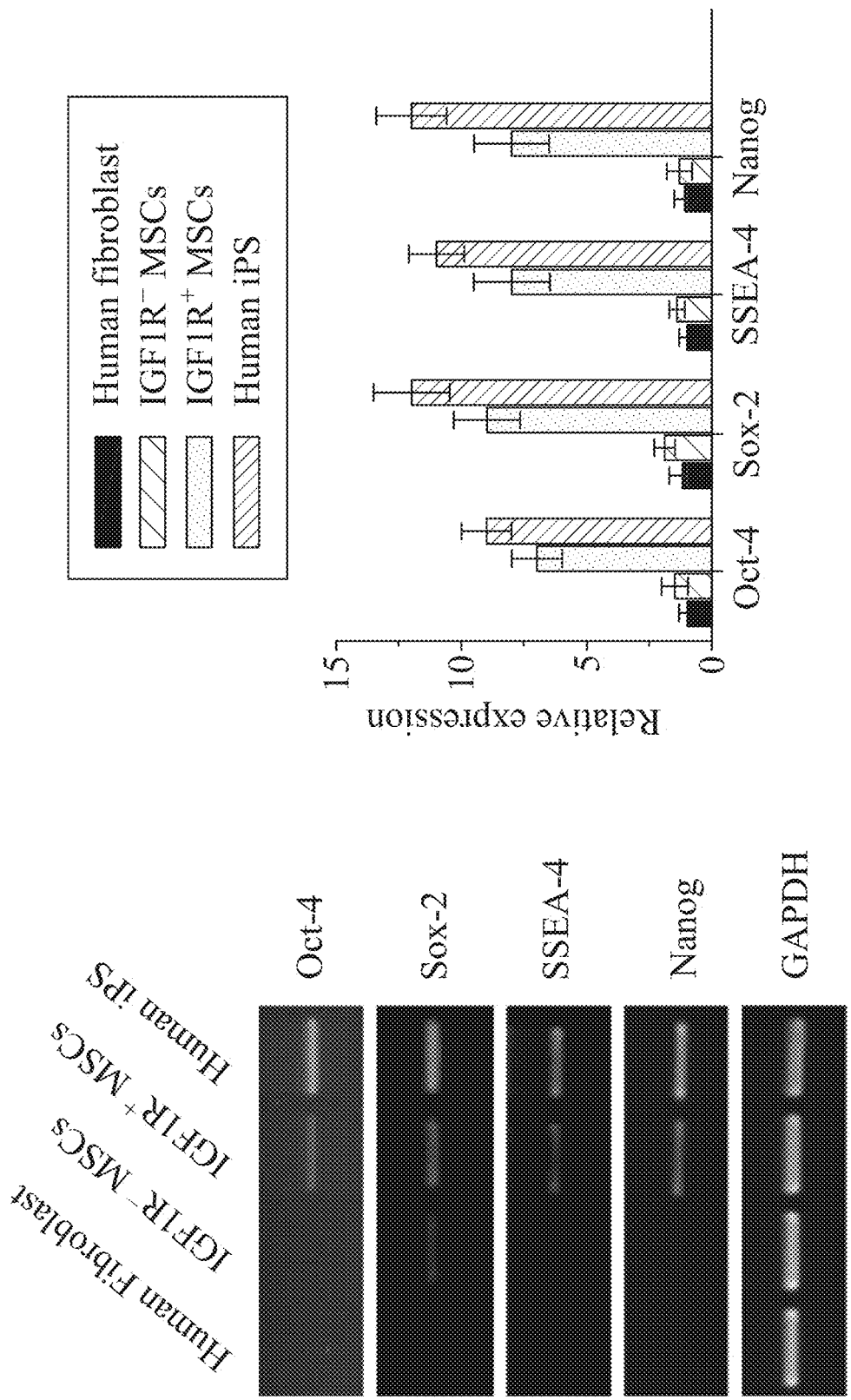
FIG. 5C shows quantitative real-time polymerase chain reaction (qRT-PCR) results of the pluripotent markers of the MSCs according to one embodiment of the present disclosure.

We perform quantitative real-time polymerase chain reaction (qRT-PCR) to further investigate the difference in the pluripotent markers expressions between the IGF1R+ MSCs and IGF1R− MSCs (the mesenchymal stem cells do not express IGF1R). FIG. 5C shows qRT-PCR results of the pluripotent markers of the MSCs, wherein the test cells are the IGF1R+ MSCs, the IGF1R− MSCs, human fibroblasts as the negative control, and induced pluripotent stem cells (iPS) as the positive control. In FIG. 5C, the IGF1R+ MSCs express higher levels of Oct-4, Sox-2, Nanog and SSEA-4 than that in the IGF1R− MSCs. It indicates that the IGF1R is essential for the IGF1R+ MSCs maintaining the multipotent capability.

1.5 In Vitro Differentiation of the IGF1R+ MSCs

To investigate whether the IGF1R+ MSCs cultured in the medium containing the hUCS or the FCS could affect the multipotent capability of the IGF1R+ MSCs, we perform the in vitro differentiation assay in this example. The fifth to tenth-passaged IGF1R+ MSCs (cultured in the medium containing the hUCS or the FCS) are seeded at a density of $5\times10^3$ cells/cm$^2$ in cell culture dishes and then cultured in different differentiation medium to induce an adipogenic differentiation, a chondrogenic differentiation, an osteogenic differentiation, a vascular tubes formation, and a neural cell differentiation. Cell morphologies of differentiated cells are observed by a microscope, and the cell types of the differentiated cells are further confirmed by staining assay.

Figure 6A:
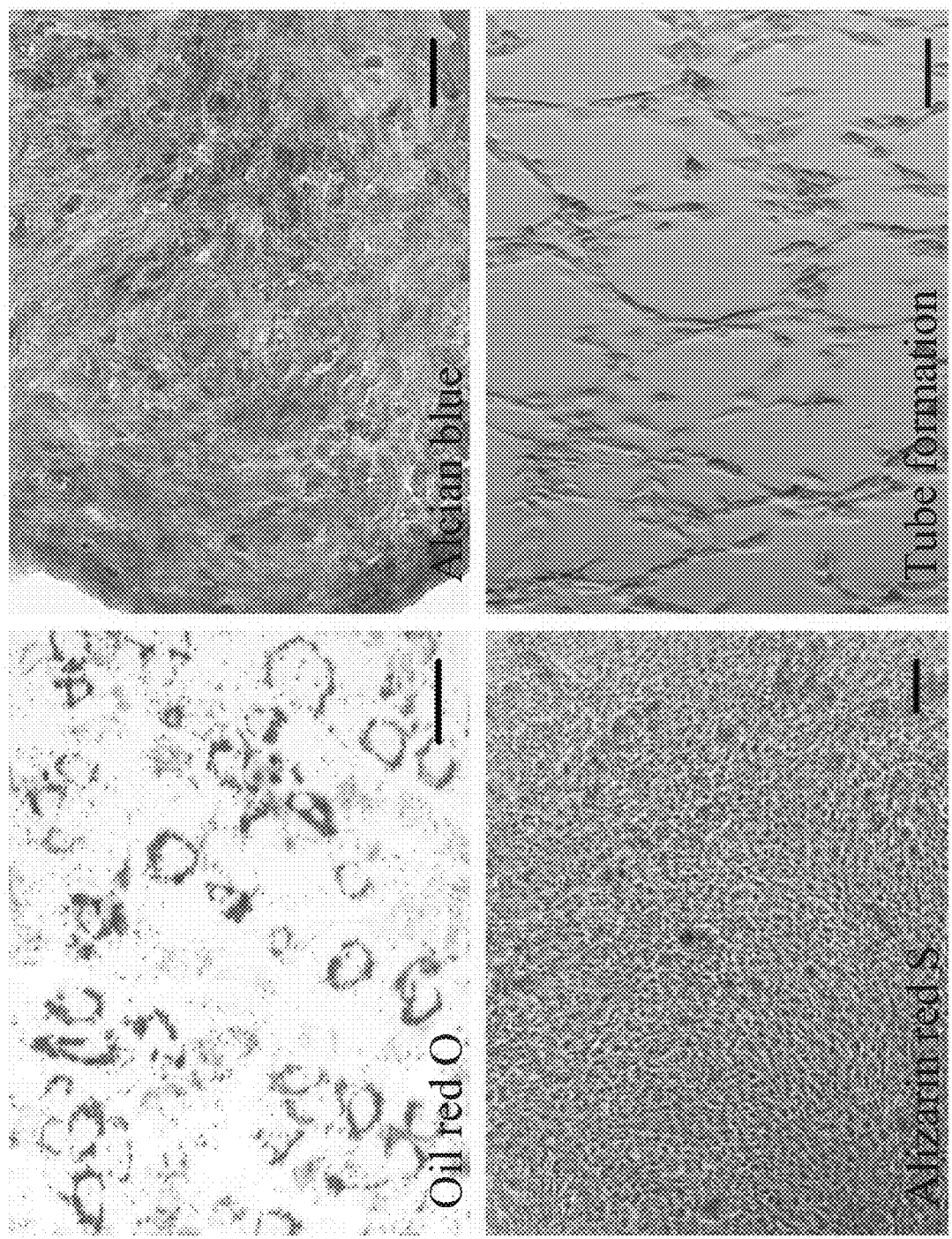
FIG. 6A is a micrograph showing that the MSCs differentiate into different tissue cells according to one embodiment of the present disclosure.
Figure 6B:
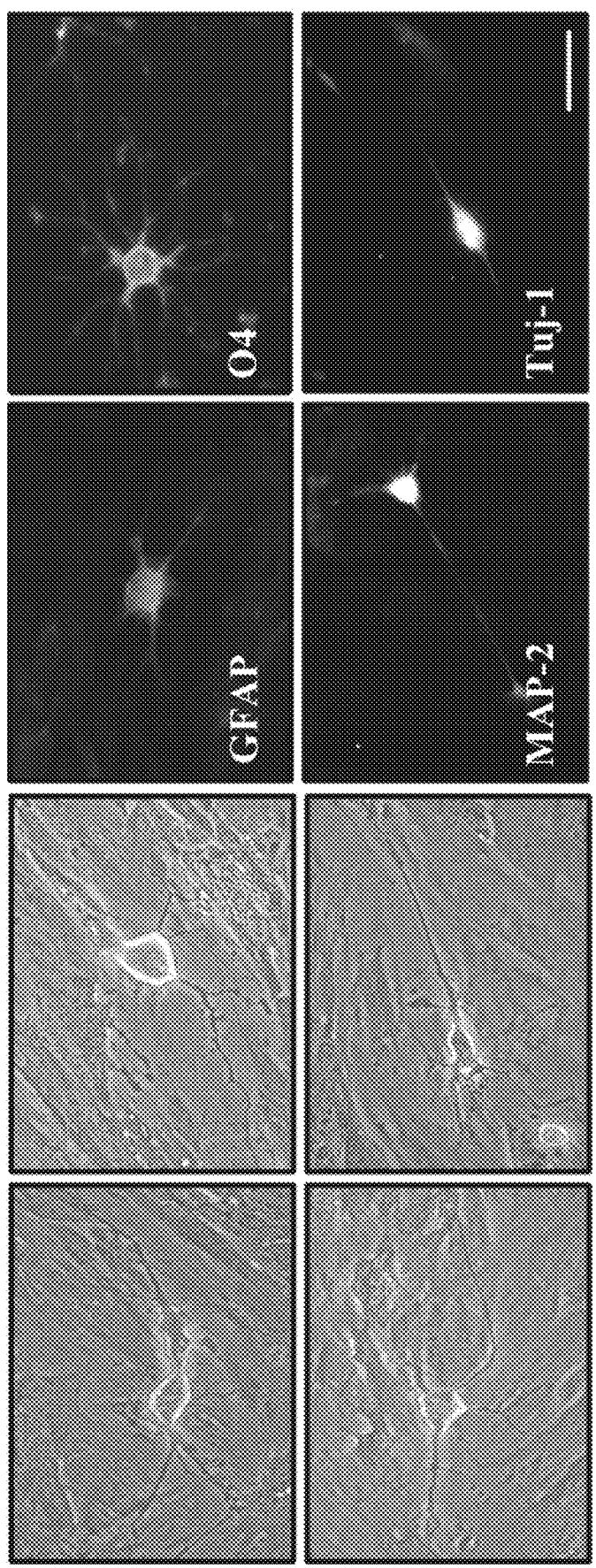
FIG. 6B is a micrograph showing that the MSCs differentiate into neuroglial cells according to one embodiment of the present disclosure.

FIG. 6A is the micrograph showing that the IGF1R+ MSCs differentiate into different tissue cells. FIG. 6B is the micrograph showing that the IGF1R+ MSCs differentiate into neuroglial cells.

In FIG. 6A, the adipogenic differentiation is confirmed by Oil red O stain, the osteogenic differentiation is confirmed by Alizarin red S stain, the chondrogenic differentiation is confirmed by Alcion blue stain, and the vascular tubes formation of the IGF1R+ MSCs is confirmed by the cell morphology observation in bright field. The results show that IGF1R+ MSCs have the abilities to differentiate into adipocytes, chondrocytes, and osteocytes and form vascular tubes.

In FIG. 6B, regarding neural differentiation, some IGF1R+ MSCs cultured in neural differentiation medium in the dish exhibit refractile cell body morphology with extended neurite-like cellular processes arranged into a network. We further identify mature neural markers expressions of the neural differentiated cell using an immunofluorescent assay. The mature neural markers includes glial fibrillary acidic protein (GFAP), microtubule-associated protein 2 (MAP-2), O4 and Neuron-specific class III beta-tubulin (Tuj-1). In FIG. 6B, IGF1R+ MSC-derived neuroglial cells express GFAP, MAP-2, O4 and Tuj-1. It indicates that the IGF1R+ MSC-derived neuroglial cells are indeed neuroglial cells.

The percentages of four mature neural markers expressions of the IGF1R+ MSCs cultured in the medium containing 2% hUCS or 10% FCS are shown in Table 1 as follows. In Table 1, the percentages of four mature neural markers expressions are higher in U-IGF1R+ MSCs than that in F-IGF1R+ MSCs. It indicates that the medium containing the hUCS improves the IGF1R+ MSCs differentiating into neuroglial cells.

TABLE 1

| serum | GFAP | MAP-2 | O4 | Tuj-1 |
|---|---|---|---|---|
| 2% hUCS | 15.2 ± 3.1% | 12.1 ± 3.1% | 9.4 ± 2.1% | 10.2 ± 1.7% |
| 10% FCS | 8.6 ± 2.2% | 7.1 ± 2.7% | 5.8 ± 1.6% | 6.1 ± 1.5% |

1.6 Regulatory Mechanism of the IGF1R+ MSCs

To investigate whether the IGF1 alone or with the PDGF-BB (a key ingredient of the hUCS) regulate the IGF1R or the CXCR4 levels of the IGF1R+ MSCs, we performed the Western blotting analysis for the IGF1R+ MSCs. The IGF1R+ MSCs are treated with different dose of the IGF1 or different dose of the PDGF-BB, and the protein expressions of the IGF1R and the CXCR4 are detected by the Western blotting analysis.

Figure 7A:
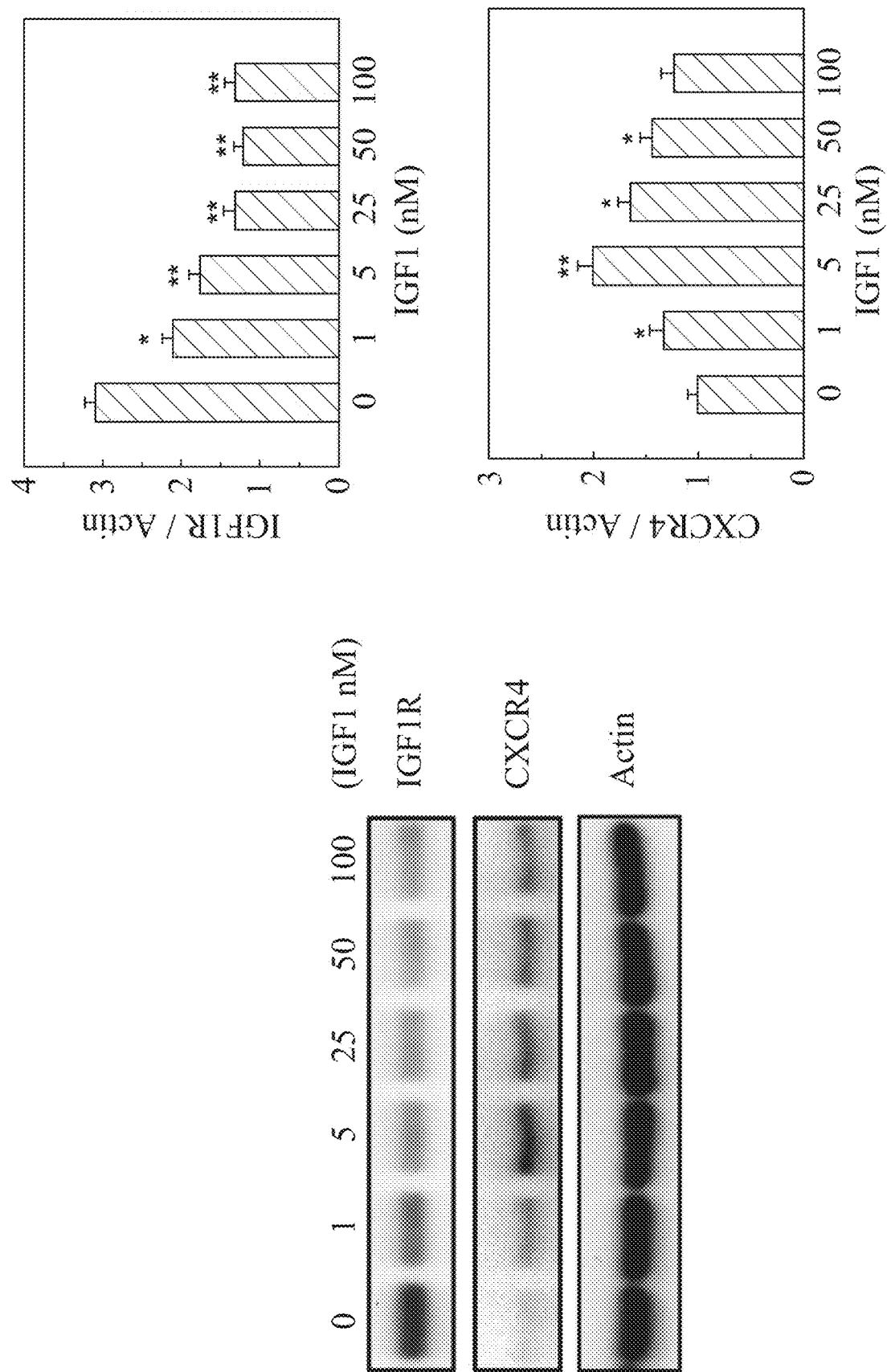
FIG. 7A shows the analytical results of the IGF1R expression and a C-X-C chemokine receptor type 4 (CXCR4) expression of the MSCs after treating different dose of insulin-like growth factor 1 (IGF1) according to one embodiment of the present disclosure.
Figure 7B:
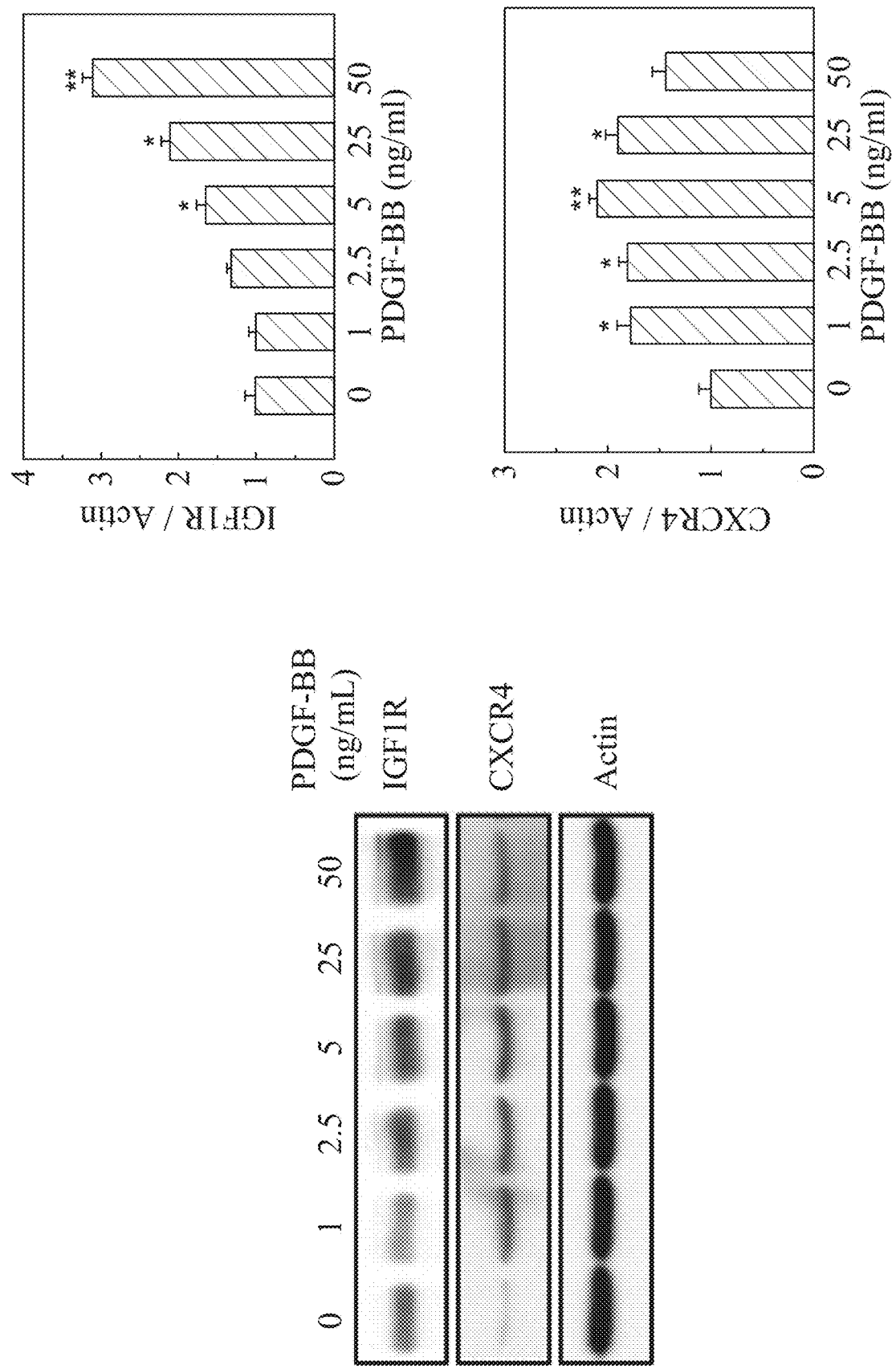
FIG. 7B shows the analytical results of the IGF1R expression and the CXCR4 expression of the MSCs after treating different dose of platelet-derived growth factor BB (PDGF-BB) according to one embodiment of the present disclosure.

FIG. 7A shows the analytical results of the IGF1R expression and the CXCR4 expression of the IGF1R+ MSCs after treating different dose of insulin-like growth factor 1 (IGF1). FIG. 7B shows the analytical results of the IGF1R expression and the CXCR4 expression of the IGF1R+ MSCs after treating different dose of the PDGF-BB. FIG. 7C shows the analytical results of the IGF1R expression and the CXCR4 expression of the IGF1R+ MSCs after treating different dose of the IGF1 and the PDGF-BB simultaneously, wherein * represents p<0.05 and ** represents p<0.01 compared to the control group (the IGF1R+ MSCs untreated with the IGF1 and the PDGF-BB). In FIG. 7A, IGF1 treatments reduce expression of IGF1R in the IGF1R+ MSCs in a dose-dependent manner, but the IGF1 treatments up-regulate the CXCR4 levels. In particular, the CXCR4 level is significantly increased by treating 5 nM IGF1. In FIG. 7B, the PDGF-BB dose-dependently increases both the IGF1R and the CXCR4 expression in the IGF1R$^+$ MSCs. In FIG. 7C, an IGF1-induced down-regulation of IGF1R is effectively inhibited by addition of the PDGF-BB.

To further determine whether the PDGF-BB is more effective than the IGF1 in activating signaling pathways that control cell proliferations, the IGF1R$^+$ MSCs are treated with the IGF1 and/or the PDGF-BB (under serum-free conditions) and the expression level of phosphorylated forms of Akt (p-Akt) and Stat3 (p-Stat3) are determined by the Western blotting analysis.

Figure 7D:
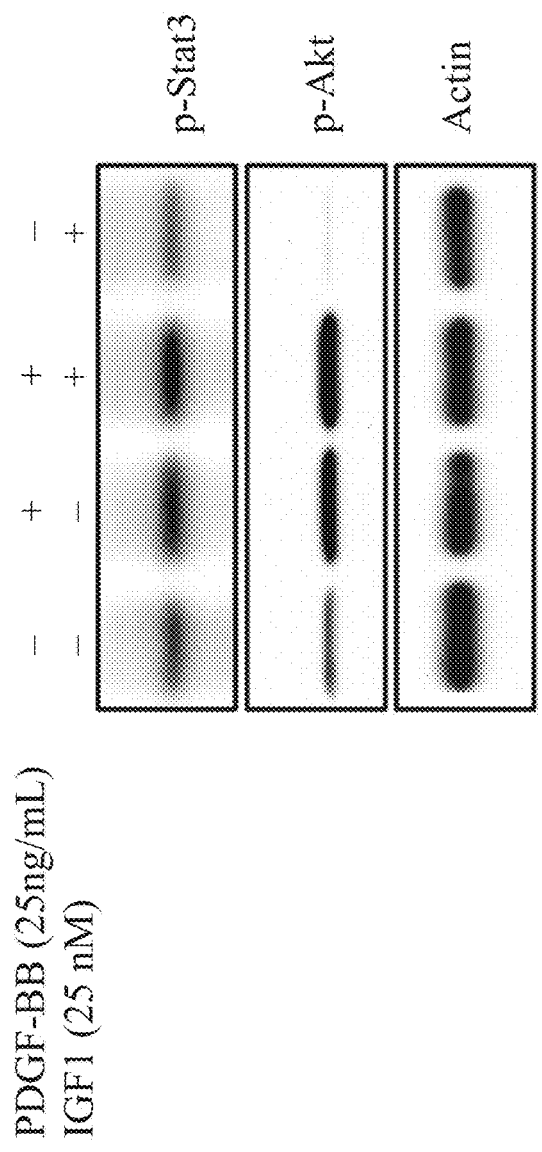
FIG. 7D shows analytical results of a phospho-Akt (p-Akt) expression and a phospho-Stat3 (p-Stat3) expression of the MSCs after treating different dose of the IGF1 and the PDGF-BB simultaneously according to one embodiment of the present disclosure.
Figure 7D:
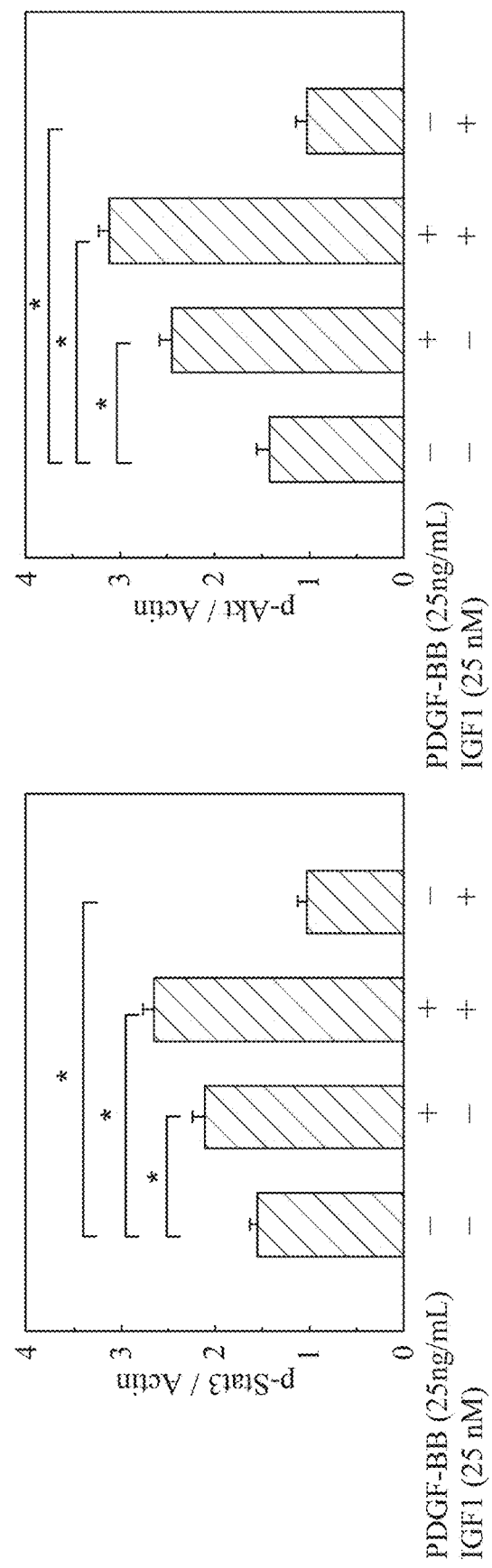

FIG. 7D shows the analytical results of the p-Akt expression and the p-Stat3 expression of the IGF1R$^+$ MSCs after treating different dose of the IGF1 and the PDGF-BB simultaneously, wherein * represents p<0.05 compared to the control group (the IGF1R$^+$ MSCs untreated with the IGF1 and the PDGF-BB). In FIG. 7D, PDGF-BB treatments significantly up-regulate the p-Akt expression and the p-Stat3 expression, whereas the IGF1 treatments have no effect on the p-Akt expression and the p-Stat3 expression (either alone or in combination with the PDGF-BB). The IGF1R$^+$ MSCs are further treated with specific pharmacological inhibitors of the p-Akt (LY294002) and the p-Stat3 (AG490) respectively. PDGF-BB-induced phosphorylations of the Akt and the Stat3 are completely inhibited by LY294002 and AG490 respectively (data not shown). Taken together, these results reveal that the PDGF-BB is more effective than the IGF1 in activating these important downstream signaling pathways, suggesting that the hUCS is better for culturing the IGF1R$^+$ MSCs than the FCS.

II. The IGF1R$^+$ MSCs Used for Treating the Brain Tissue Damage

The data of the first part examples demonstrate that the IGF1R$^+$ MSCs have self-renewal capability and multipotent capability. In the second part examples, we further discuss the effect on the IGF1R$^+$ MSCs used for treating the brain tissue damage.

2.1 The IGF1R$^+$ MSCs Transplantation Improved Neurological Behavior in Stroke Rat Model In vivo self-renewal and neuroregenerative potentials of the IGF1R$^+$ MSCs are assessed in a stroke model in the second part examples. Rats before and after the stroke are measured by three modalities of neurological deficits to evaluate the neurological recovery.

An ischemia-reperfusion model is used to simulate transient focal cerebral ischemia in rats. Test animals are male Sprague-Dawley (SD) rats weighing 225-275 g. The ischemia-reperfusion model is induced by ligations of bilateral common carotid arteries (CCAs) and a right middle cerebral artery (MCA). The bilateral CCAs are clamped with non-traumatic arterial clips, and the right MCA is ligated with an 10-0 nylon suture. After 90 minutes ischemia, the suture on the MCA and the arterial clips on CCAs are removed to allow reperfusion. One hour after brain ischemia, the rats are injected intravenously with approximately 2×10$^6$ cells into femoral vein. The rats are subdivided into five treatment groups: (1) a U-IGF1R$^+$ MSCs treatment group (n=8), (2) the IGF1R$^+$ MSCs cultured in the medium containing the FCS (F-IGF1R$^+$ MSCs treatment group; n=8), (3) the MSCs cultured in the medium containing the hUCS (U-MSCs treatment group; n=8), (4) the MSCs cultured in the medium containing the FCS (F-MSCs treatment group; n=8), and (5) vehicle-control group (n=8). The rats of the U-IGF1R$^+$ MSCs treatment group further perform a blocking experiment by administering a CXCR4 antibody (CXCR4-Ab mAb 173, R&D System) and an IGF1R inhibitor (PPP, Santa Cruz Biotechnology) to block the CXCR4 and the IGF1R. For the blocking experiment, the rats of group 1 are administered the CXCR4-Ab mAb by intraperitoneal injection twice weekly for two weeks and received i.p. injections of the PPP (20 mg/kg/day) for three days.

Neurological behavioral assessments are performed 5 days before cerebral ischemia/reperfusion, and 1, 7, 14 and 28 days after cell transplantation. The three modalities of neurological deficits measure body asymmetry, locomotor activity and grip strength of the rats.

i. A Body Swing Test

The body swing test is used to assess body asymmetry after MCA ligation. Initially, the rats are suspended by their tail 10 cm above the cage floor, and lateral body movements are recorded. Specifically, the frequency with which the initial head swing contra-lateral to the ischemic side is counted in twenty consecutive tests and is normalized to the baseline score.

Figure 8A:
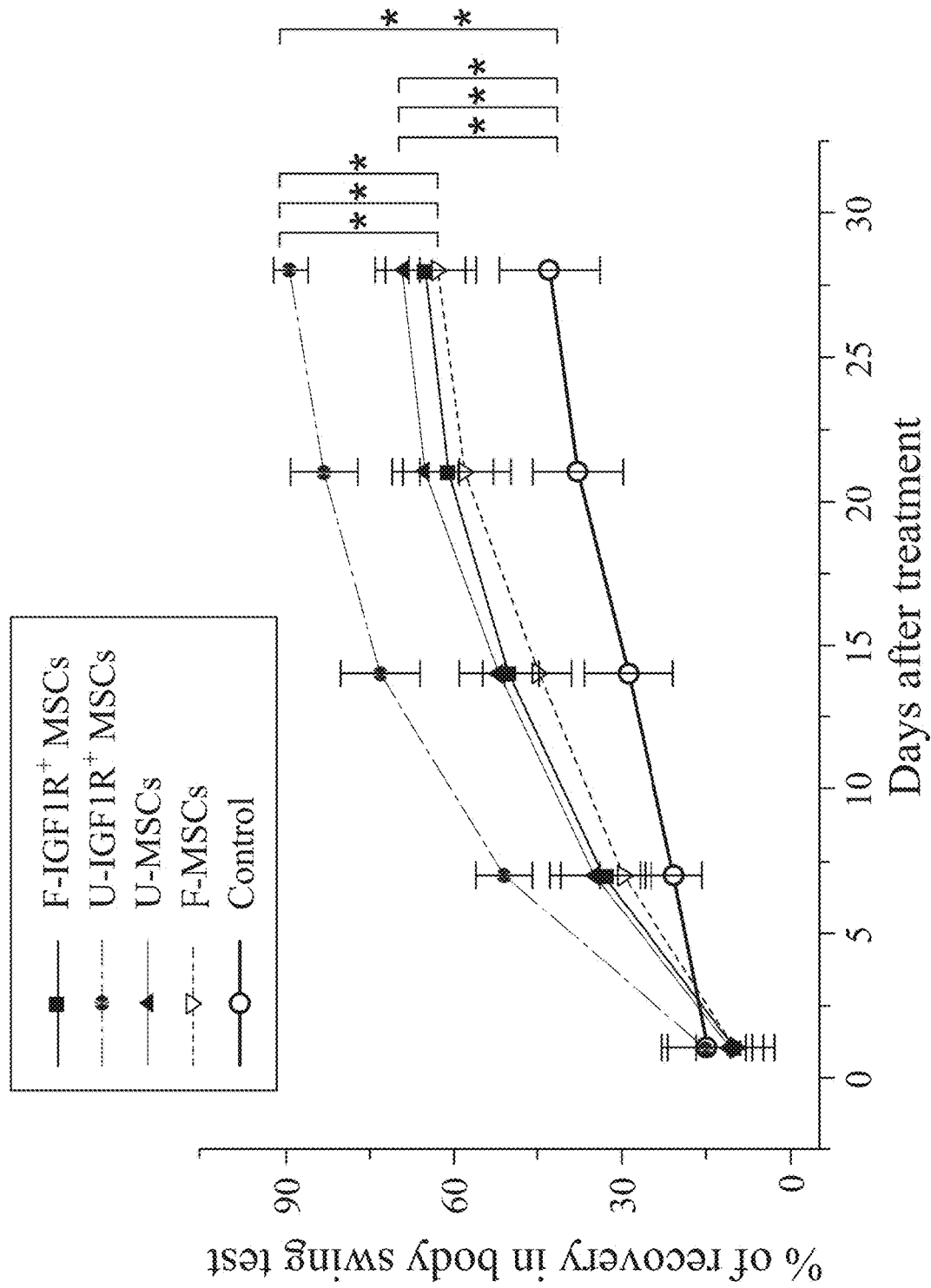
FIG. 8A shows analytical results of a body swing test of the rats.
Figure 8B:
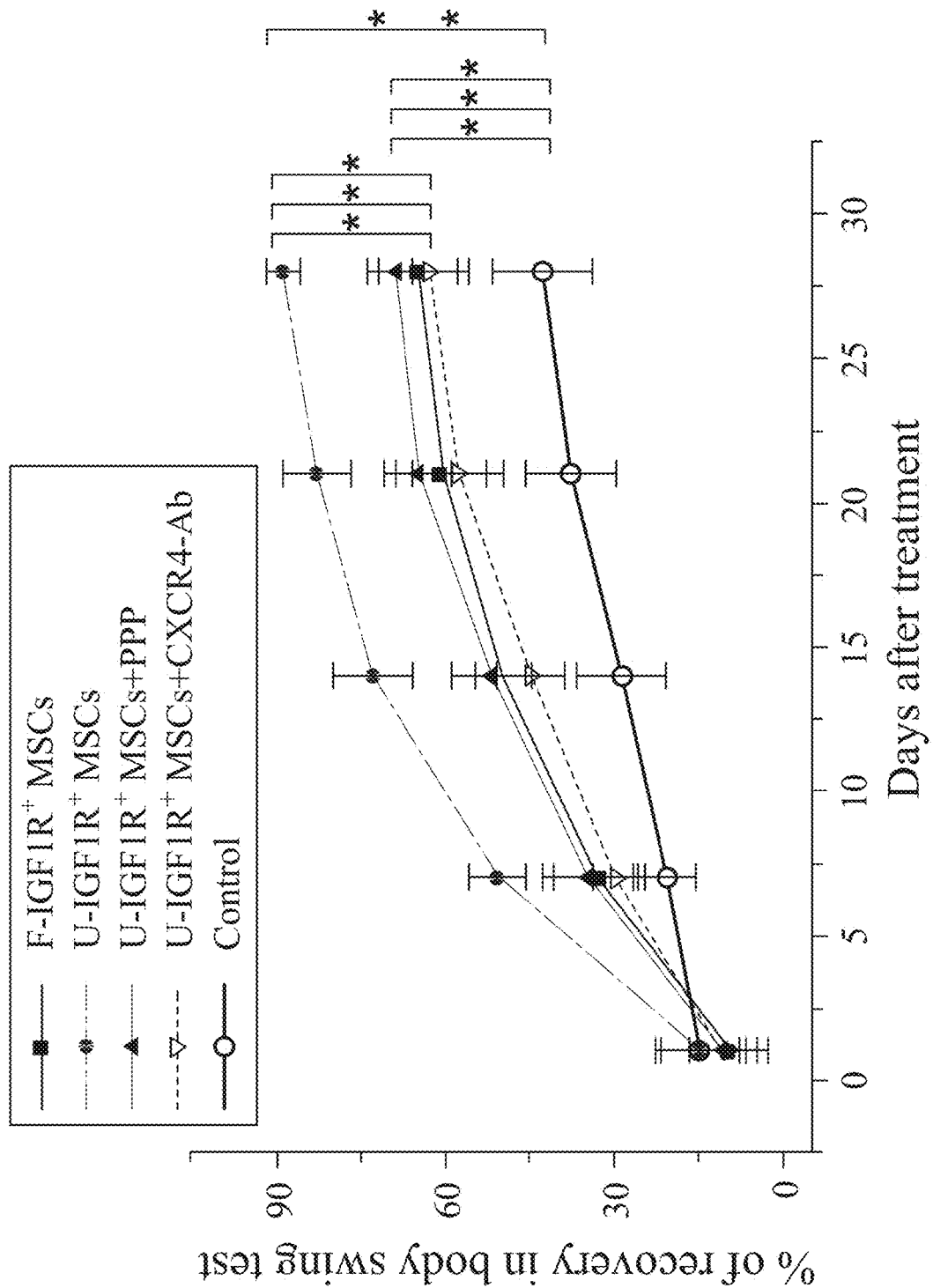
FIG. 8B shows analytical results of the body swing test of the rats performed a blocking experiment.

FIG. 8A shows the analytical results of the body swing test of the rats. FIG. 8B shows the analytical results of the body swing test of the rats performed a blocking experiment. In FIG. 8A, all rats treated with the MSCs (four MSCs in this example) exhibit significantly better functional recovery than control. The neurological recovery of the rats treated with the MSCs cultured in the medium containing the hUCS (group 1 and group 3) are better than the neurological recovery of the rats treated with the MSCs cultured in the medium containing the FCS (group 2 and group 4). In particular, the rats treated with the U-IGF1R$^+$ MSCs (group 1) show significantly more improvement than all other groups. In FIG. 8B, when the group 1 is treated with the PPP (n=8) or the CXCR4-Ab mAb 173 (n=8), the neurological recovery for the body swing test is similar to control. It indicates that the effect on the functional recovery through the U-IGF1R$^+$ MSCs treatment is inhibiting by blocking the CXCR4 and the IGF1R.

ii. A Locomotor Activity Test

The locomotor activity test is measured for about 2 hours using VersaMax Animal Activity Monitoring System (Accuscan Instruments), which contains 16 horizontal infrared sensors and 8 vertical infrared sensors. The vertical sensors are situated 10 cm above the chamber floor and the locomotor activity is quantified by a number of a beam broken by the rat's movement in the chamber. Three vertical-movement parameters are measured: (i) vertical activity (ii) vertical time (iii) number of vertical movements by the manufacturer's instruction.

Figure 9A:
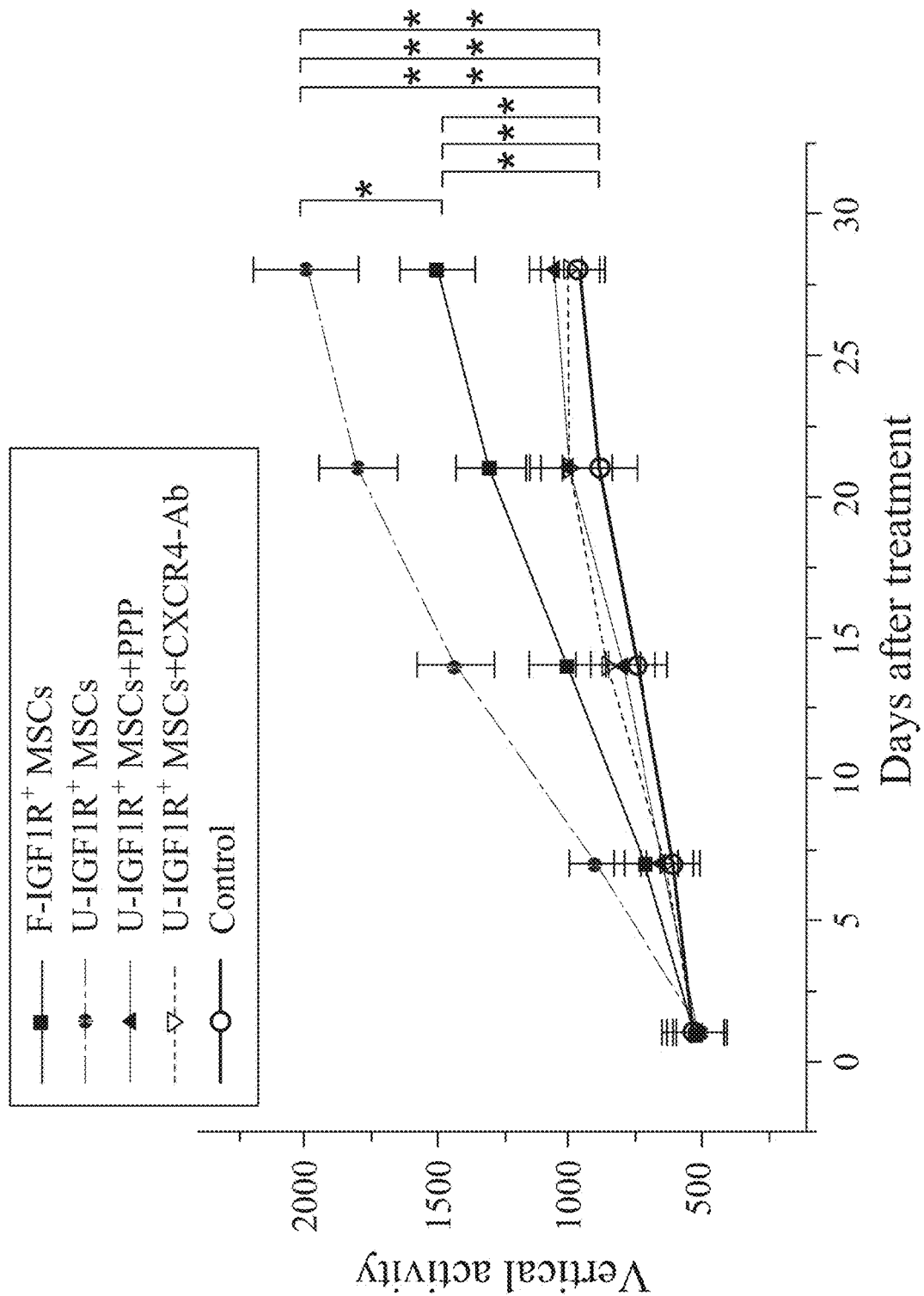
FIG. 9A shows analytical results of a vertical activity in a locomotor activity test.
Figure 9B:
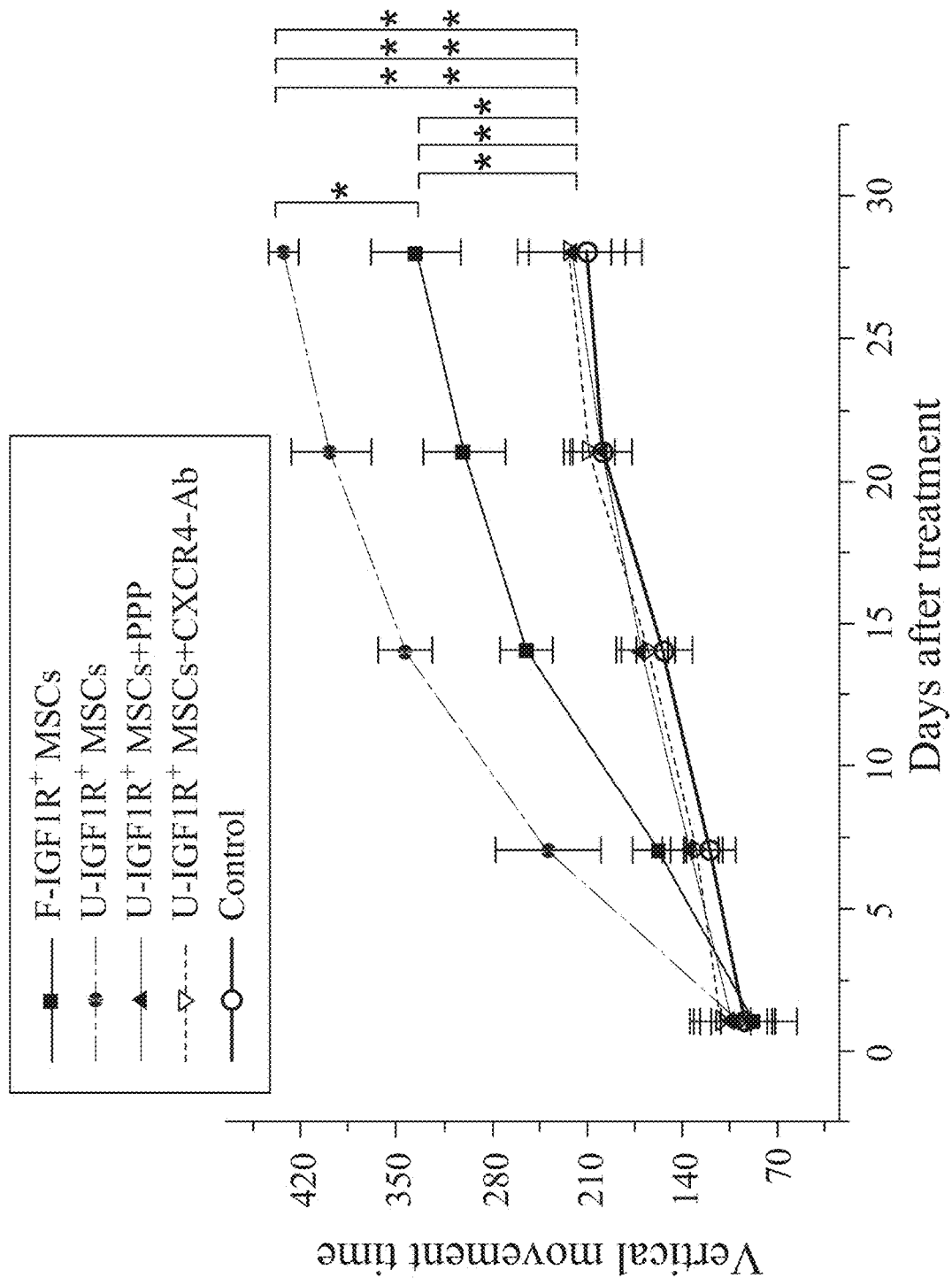
FIG. 9B shows analytical results of a vertical movement time in the locomotor activity test.
Figure 9C:
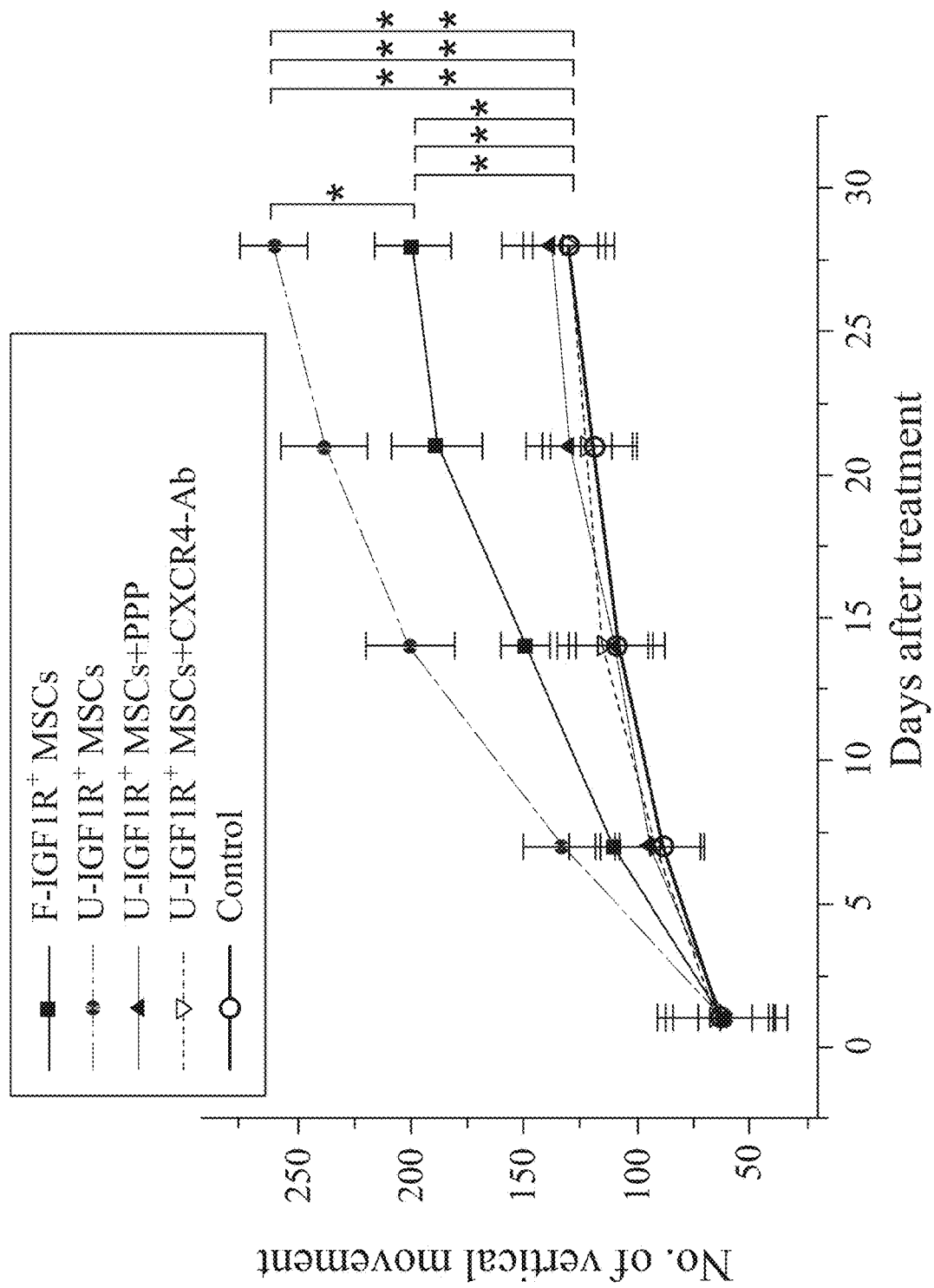
FIG. 9C shows analytical results of a number of the vertical movements in the locomotor activity test.

FIG. 9A shows the analytical results of the vertical activity in the locomotor activity test. FIG. 9B shows the analytical results of the vertical movement time in the locomotor activity test. FIG. 9C shows the analytical results of the number of the vertical movements in the locomotor activity test. In FIGS. 9A-9C, all rats treated with the MSCs (four MSCs in this example) exhibit significantly improvement in the locomotor activity than the control group, and the rats treated with the U-IGF1R$^+$ MSCs show significantly more improvement in the locomotor activity than the rats treated with the F-IGF1R$^+$ MSCs. However, the locomotor activity of group 1 is similar to the control group when the group 1 is treated with the PPP or the CXCR4-Ab. It indicates that the effect on locomotor activity improvement through the U-IGF1R$^+$ MSCs treatment is inhibiting by blocking the CXCR4 and the IGF1R.

iii. A Grip Strength Test

The grip strength is analyzed using Grip Strength Meter (TSE-Systems). In brief, the grip strength of each forelimb of the rat is measured separately from the mean of 20 pulls, and the ratio of ipsilateral grip strength to contralateral grip strength is calculated. In addition, the ratio of grip strength post-cell-treatment and pre-cell-treatment is also calculated, and the changes are presented as a percentage of the pre-cell-treatment value.

Figure 10:
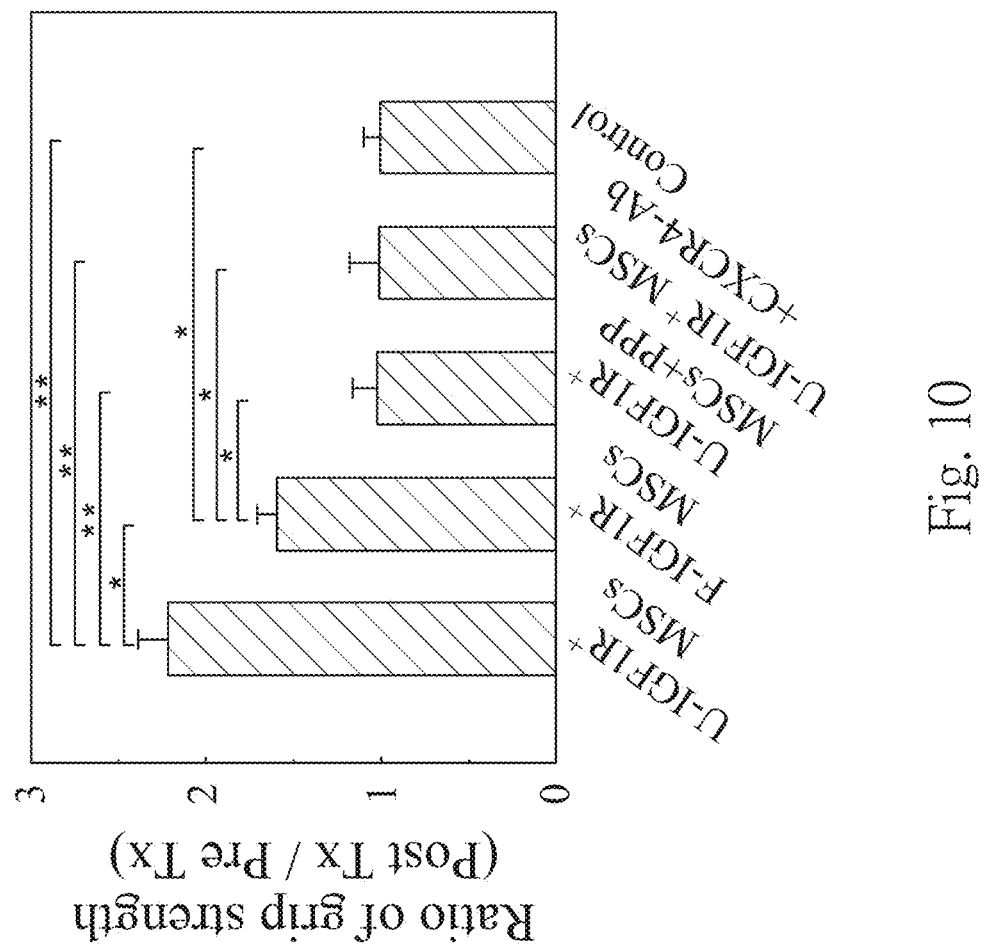
FIG. 10 shows analytical results of a grip strength test of the rats.

FIG. 10 shows the analytical results of the grip strength test of the rats. In FIG. 10, the rats treated with the IGF1R$^+$ MSCs exhibit significantly improvement in the grip strength than the control group, and the rats treated with the U-IGF1R$^+$ MSCs show significantly more improvement in the grip strength than the rats treated with the F-IGF1R$^+$ MSCs. However, the grip strength of group 1 is similar to the control group when the group 1 is treated with the PPP or the CXCR4-Ab. It indicates that the effect on grip strength improvement through the U-IGF1R$^+$ MSCs treatment is inhibiting by blocking the CXCR4 and the IGF1R.

These results of three modalities of neurological deficits suggest that the IGF1R$^+$ MSCs can improve the neurological behaviors in stroke-induced rats. In particular, the U-IGF1R$^+$ MSCs rather than the F-IGF1R$^+$ MSCs have superior neuroregenerative potential that required the IGF1R and the CXCR4 receptor pathways.

2.2 The IGF1R$^+$ MSCs Transplantation Enhance a Glucose Metabolism

To investigate whether the U-IGF1R$^+$ MSCs implantation affected glucose metabolic activity following cerebral ischemia, the glucose metabolic activity of the stroke-induced rats treated with the U-IGF1R$^+$ MSCs are examined by using microPET to perform [$^{18}$F] fluoro-2-deoxyglucose positron emission tomography (FDG-PET).

Figure 11A:
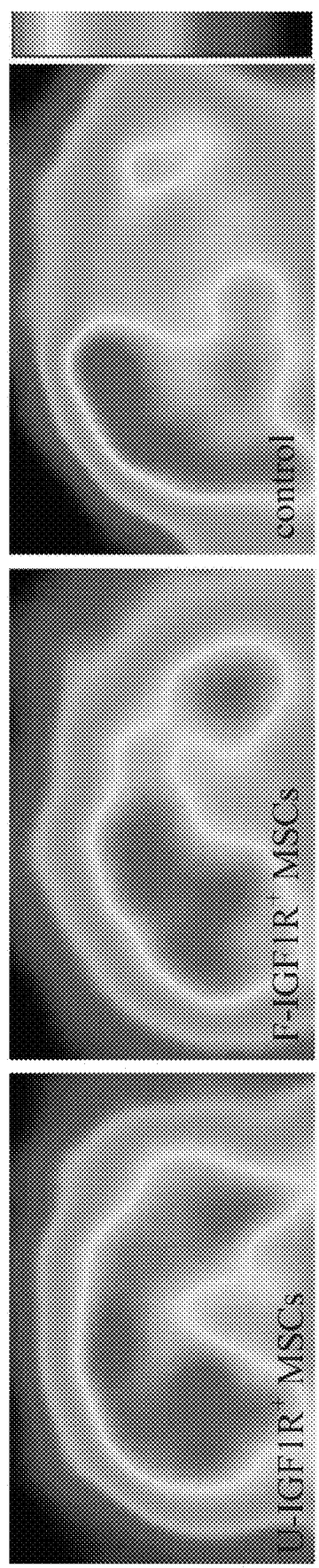
FIG. 11A is a [$^{18}$F] fluoro-2-deoxyglucose positron emission tomography (FDG-PET) image of the rats administered with a cell treatment.
Figure 11B:
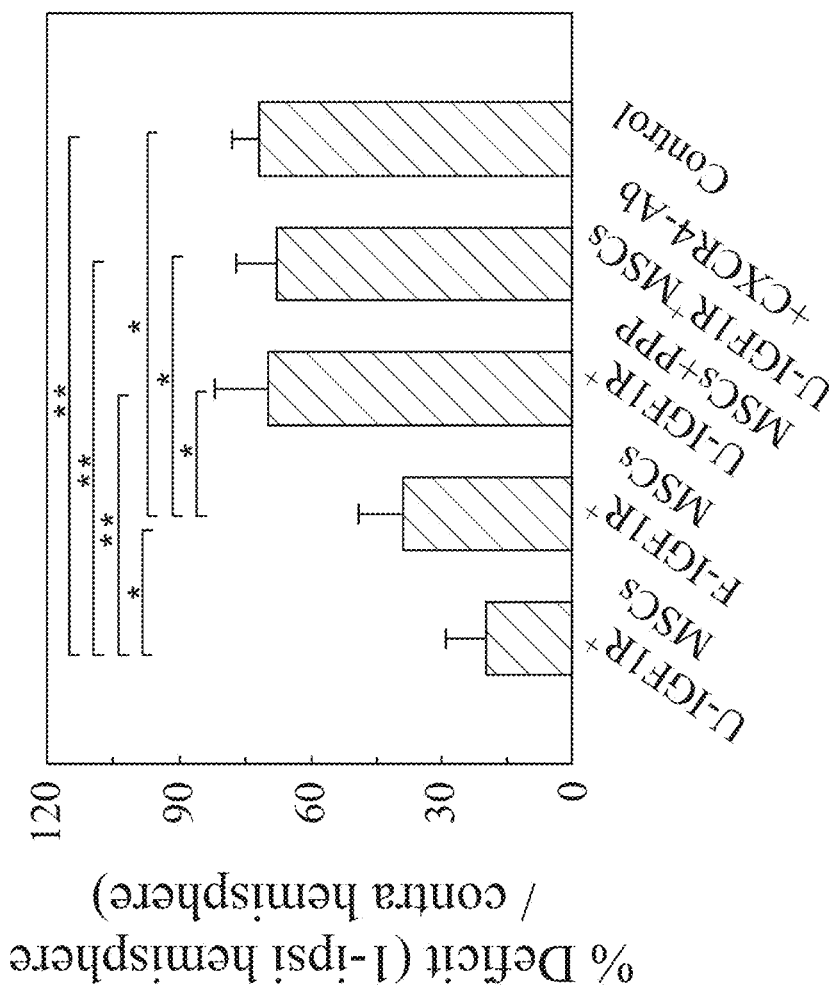
FIG. 11B is a quantitative diagram of the [$^{18}$F] FDG-PET image of the rats administered with the cell treatment.

FIG. 11A is a [$^{18}$F] image of the rats administered with a cell treatment. FIG. 11B is a quantitative diagram of the [$^{18}$F] FDG-PET image of the rats administered with the cell treatment. The rats are subdivided into five cell treatment groups: the U-IGF1R$^+$ MSCs treatment group (n=6), the F-IGF1R$^+$ MSCs treatment group (n=6), the U-IGF1R$^+$ MSCs treatment and the PPP injection simultaneously group (n=6), the U-IGF1R$^+$ MSCs treatment and the CXCR4-Ab injection simultaneously group (n=6), and the control group (n=6). The rats are performed [$^{18}$F] FDG-PET at four weeks after the cell treatment. In FIG. 11A, the IGF1R$^+$ MSCs implantation increase the FDG uptake in damaged cortical regions (right side of the brain), and the FDG uptake enhancement in the U-IGF1R$^+$ MSCs treatment group is greater than the F-IGF1R$^+$ MSCs treatment group and control group. FIG. 11B is a semiquantitative measurement of the [$^{18}$F] FDG-PET image. In FIG. 11B, the enhancement in the glucose metabolic activity is abolished in the U-IGF1R$^+$ MSCs treatment and the PPP injection simultaneously group or the U-IGF1R$^+$ MSCs treatment and the CXCR4-Ab injection simultaneously group. It indicates that the effect on the glucose metabolic activity enhancement through the U-IGF1R$^+$ MSCs treatment is inhibiting by blocking the CXCR4 and the IGF1R.

2.3 Intravenous Transplantation of the IGF1R$^+$ MSCs Increases the Expression of Anti-Apoptotic Proteins In Vivo In order to determine whether the stroke-induced rats treated with the U-IGF1R$^+$ MSCs exhibit improved neurological function by means of up-regulation of survival factors, we examine the protein expression of the anti-apoptotic proteins in the ischemic area of the stroke-induced rats using the Western blotting analysis. The detected anti-apoptotic proteins are B-cell lymphoma 2 (Bcl-2) and B-cell lymphoma-extra large (Bcl-xL). The expression of pro-apoptotic proteins are also detected in this example, wherein the detected pro-apoptotic proteins are BCl2-associated X protein (Bax) and BCl2-associated death promoter (Bad).

Figure 12:
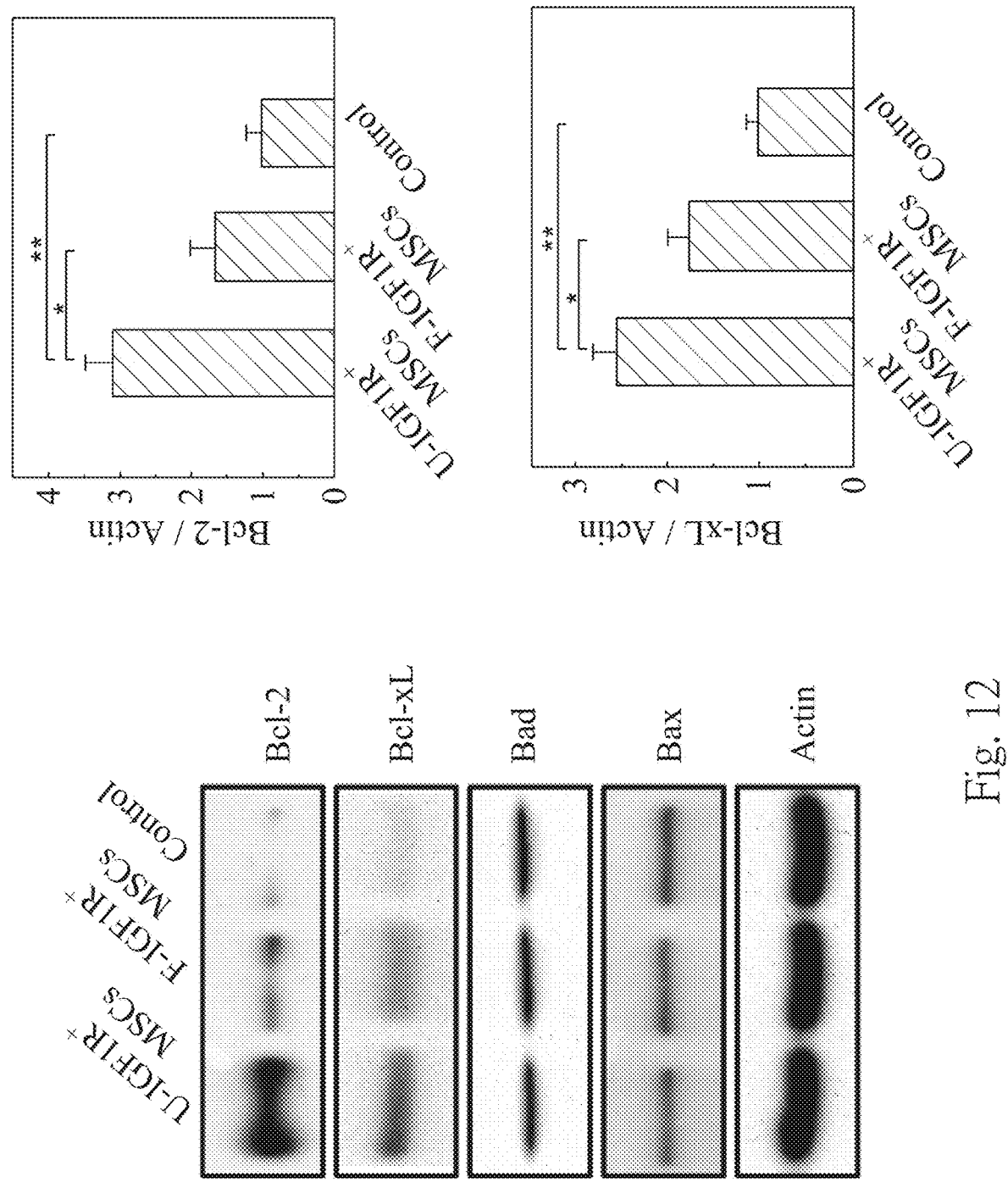
FIG. 12 shows analytical results of anti-apoptotic proteins expression levels of an ischemic area in the rats administered with the cell treatment.

FIG. 12 shows the analytical results of anti-apoptotic proteins expression levels of the ischemic area in the rats administered with the cell treatment. In FIG. 12, the protein expressions of the Bcl-2 and the Bcl-xL of the ischemic area are increased in the rats administered with the IGF1R$^+$ MSCs treatment. Significant up-regulations of anti-apoptotic proteins of the Bcl-2 and the Bcl-xL are found in the U-IGF1R$^+$ MSCs treatment group (n=6) compared with the F-IGF1R$^+$ MSCs treatment group (n=6) and the control group (n=6), wherein $p<0.05$ when the F-IGF1R$^+$ MSCs treatment group compares to the control group, and $p<0.01$ when the U-IGF1R$^+$ MSCs treatment group compares to the control group. In contrast, the protein expression levels of the Bax and the Bad in the ischemic area are not affected by the IGF1R$^+$ MSCs treatment (the F-IGF1R$^+$ MSCs treatment and the U-IGF1R$^+$ MSCs treatment).

2.4 The IGF1R$^+$ MSCs Treatment Enhances Neural Differentiation In Vivo

To analyze whether transplanted the IGF1R$^+$ MSCs could differentiate into the neuroglial cells, we perform the immunofluorescence staining assay to determine number of the implanted IGF1R$^+$ MSCs in the ischemic area of the rats and the immunofluorescence double staining assay to determine the differentiation cell-type of the implanted IGF1R$^+$ MSCs using laser scanning confocal microscopy at 28 days after transplantation.

Figure 13A:
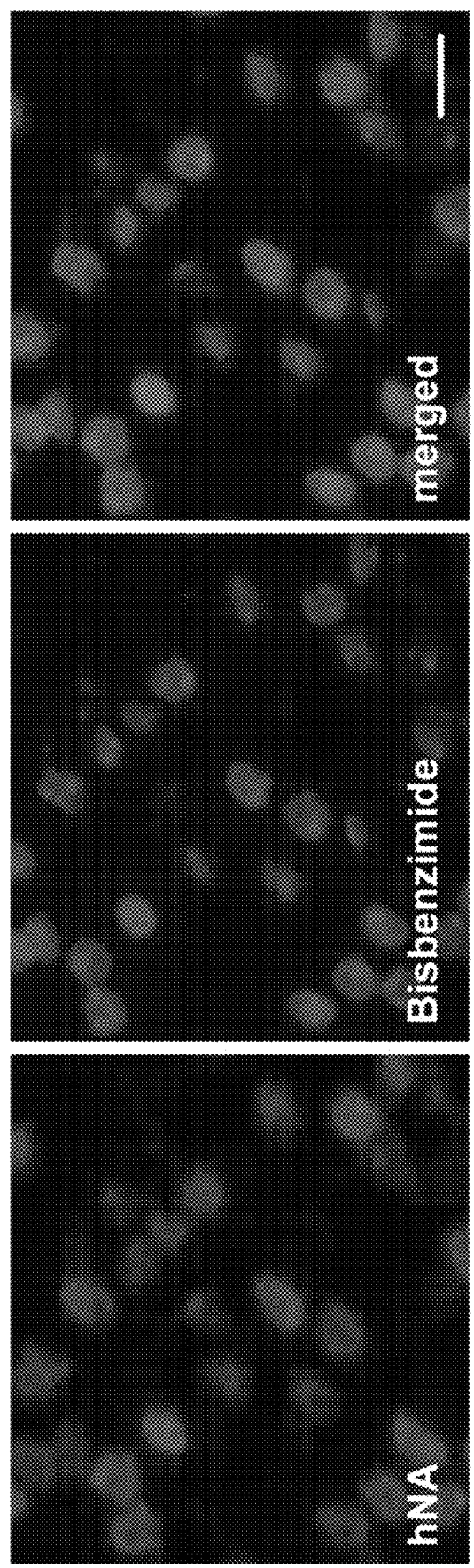
FIG. 13A is a micrograph showing that bisbenzimide and human nuclear antigen (hNA) are co-localization in the ischemic area of the rats administered with the cell treatment.
Figure 13B:
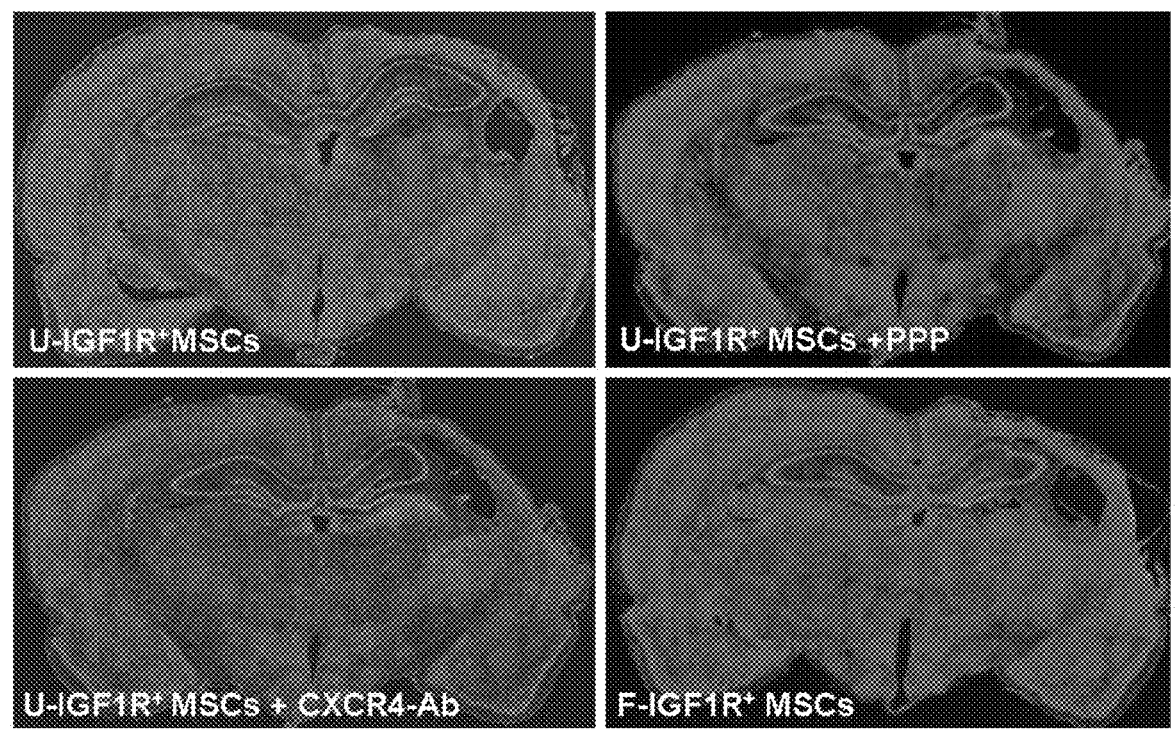
FIG. 13B is a micrograph showing number of implanted IGF1R$^+$ mesenchymal stem cells (IGF1R$^+$ MSCs) in brain tissues of the rats administered with the cell treatment.
Figure 13B:
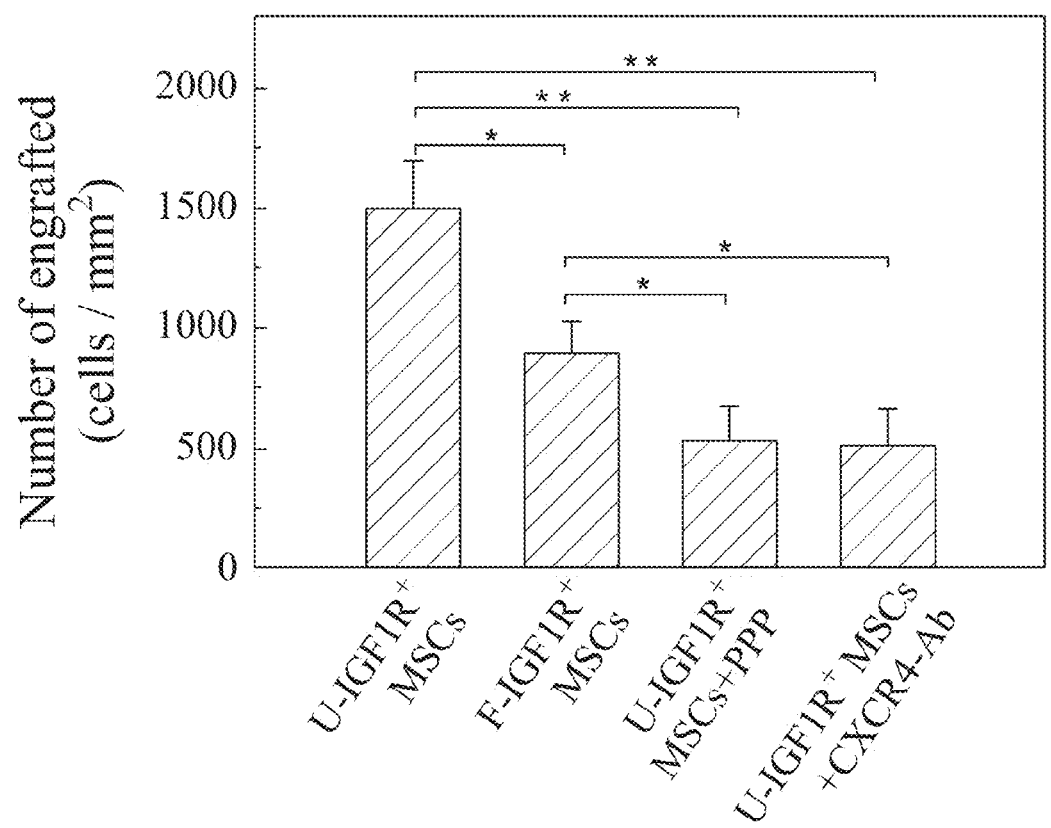

FIG. 13A is the micrograph showing that bisbenzimide and human nuclear antigen (hNA) are co-localization in the ischemic area of the rats administered with the cell treatment. FIG. 13B is the micrograph showing number of implanted IGF1R$^+$ MSCs in the brain tissues of the rats administered with the cell treatment. In FIG. 13A, all bisbenzimide-labeled IGF1R$^+$ MSCs express the hNA, confirming their human origin. In FIG. 13B, the U-IGF1R$^+$ MSCs treatment group (n=8) have more implanted IGF1R$^+$ MSCs in the ischemic area than the F-IGF1R$^+$ MSCs treatment group (n=8) ($p<0.05$). However, the blocking experiment (the U-IGF1R$^+$ MSCs treatment and the PPP injection simultaneously group or the U-IGF1R$^+$ MSCs treatment and the CXCR4-Ab injection simultaneously group) results show that the difference is abolished by the injection of the PPP and the CXCR4-Ab.

To further confirm the differentiation cell-type of the implanted IGF1R$^+$ MSCs, we perform the immunofluorescence double staining assay labeling cell-type specific markers, the IGF1R, and the CXCR4 to determine the co-localization of the cell-type specific markers and the IGF1R, and the co-localization of the cell-type specific markers and the CXCR4. The nucleus is labeled by the bisbenzimide. The cell-type specific markers include glial fibrillary acidic protein (GFAP), microtubule-associated protein 2 (MAP-2), and neuronal nuclear antigen (NeuN).

Figure 14A:
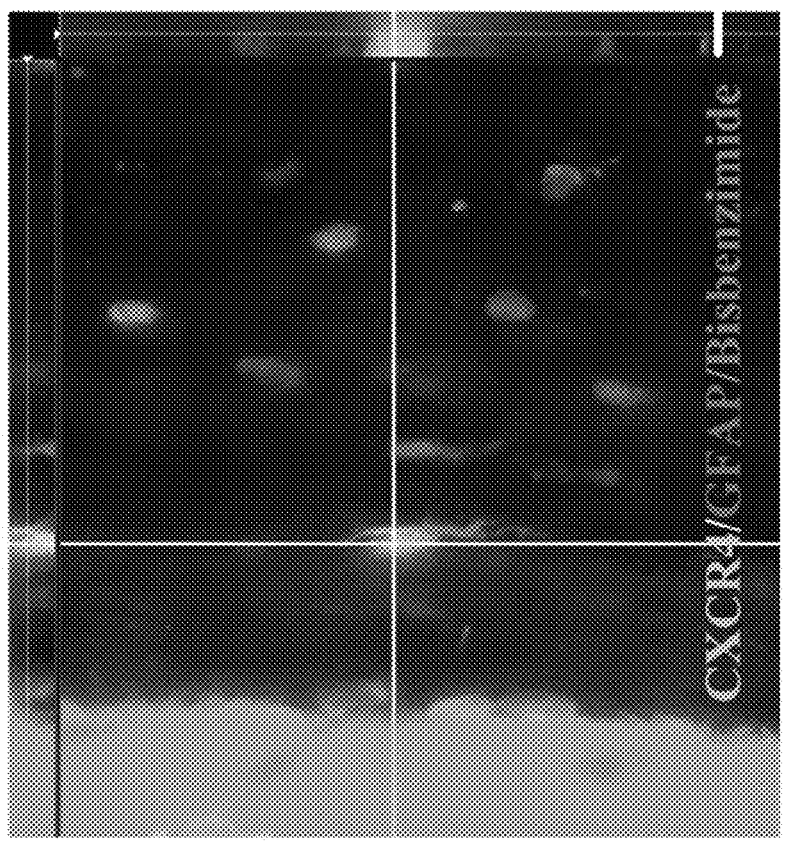
FIG. 14A is a micrograph showing that glial fibrillary acidic protein (GFAP) is co-localized with the IGF1R or the CXCR4 in the IGF1R$^+$ MSCs which are implanted into the ischemic area of stroke-induced rats.
Figure 14A:
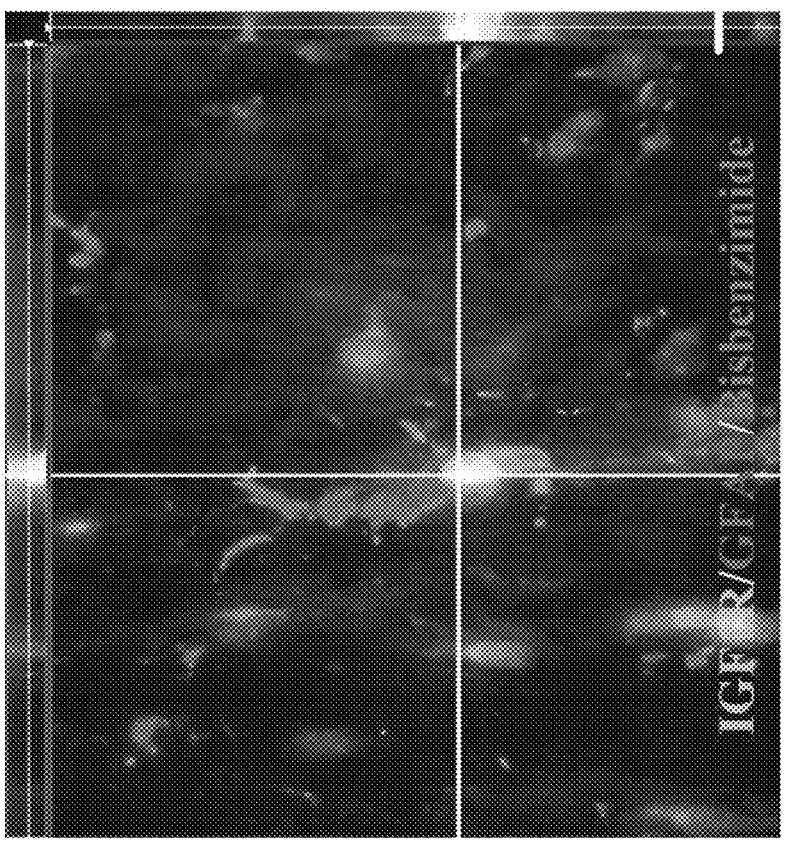
Figure 14B:
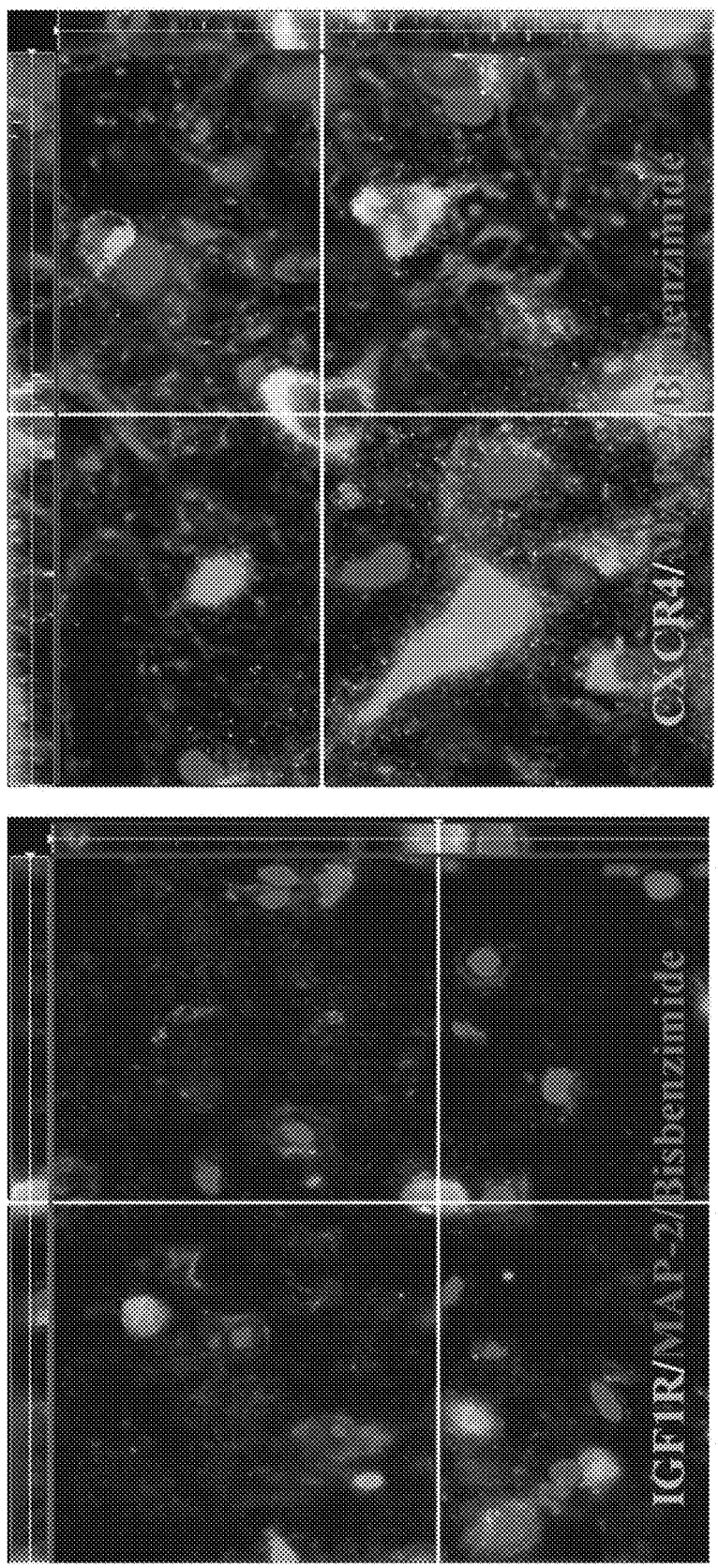
FIG. 14B is a micrograph showing that microtubule-associated protein 2 (MAP-2) is co-localized with the IGF1R or the CXCR4 in the IGF1R$^+$ MSCs which are implanted into the ischemic area of the stroke-induced rats.
Figure 14C:
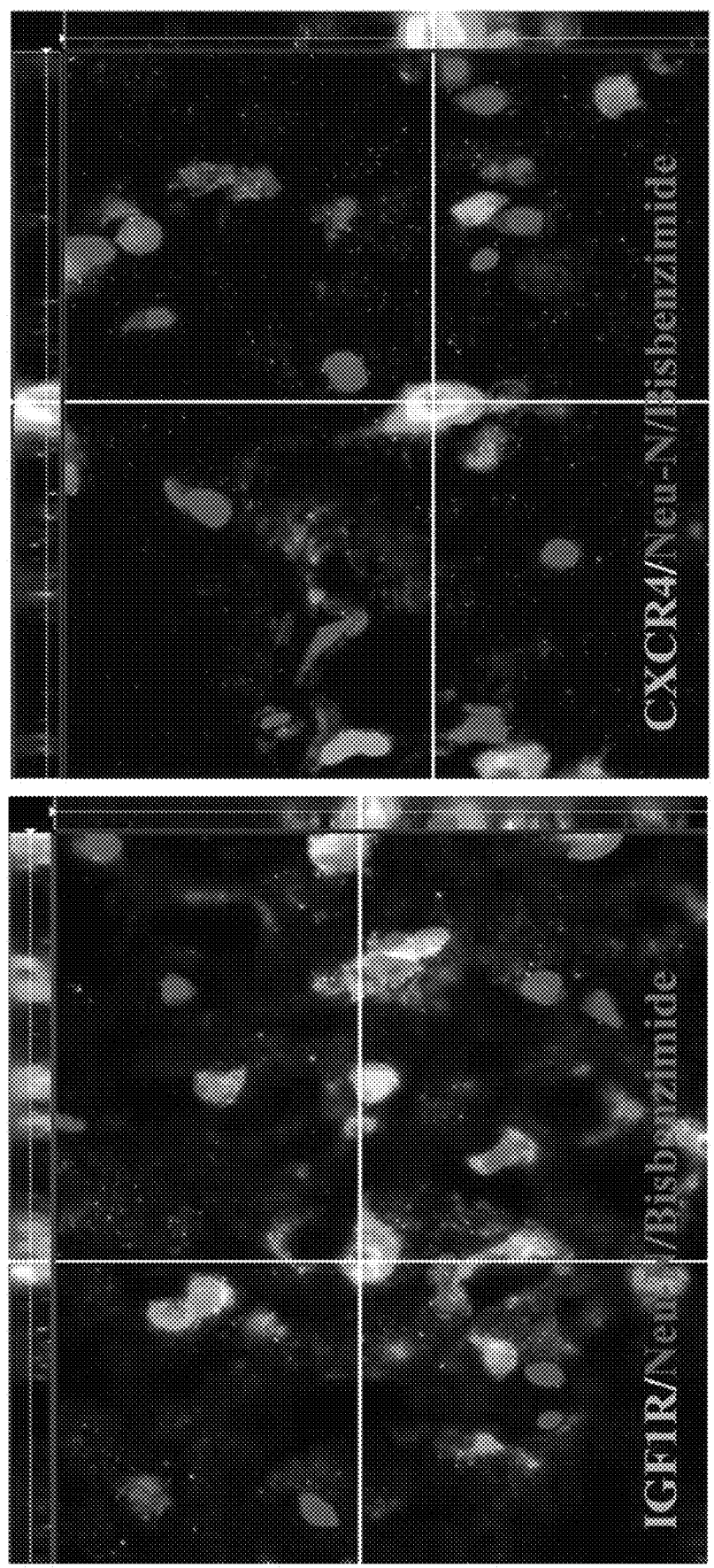
FIG. 14C is a micrograph showing that neuronal nuclear antigen (NeuN) is co-localized with the IGF1R or the CXCR4 in the IGF1R$^+$ MSCs which are implanted into an ischemic area of the stroke-induced rats.

FIG. 14A is the micrograph showing that the GFAP is co-localized with the IGF1R or the CXCR4 in the IGF1R$^+$ MSCs which are implanted into the ischemic area of the stroke-induced rats. FIG. 14B is the micrographs showing that the MAP-2 is co-localized with the IGF1R or the CXCR4 in the IGF1R$^+$ MSCs which are implanted into the ischemic area of the stroke-induced rats. FIG. 14C is the micrographs showing that the NeuN is co-localized with the IGF1R or the CXCR4 in the IGF1R$^+$ MSCs which are implanted into the ischemic area of the stroke-induced rats.

In FIGS. 14A-14C, some bisbenzimide-labeled cells that express the CXCR4 are co-localized with neural markers of the GFAP, the MAP-2, and the Neu-N, respectively. In addition, some bisbenzimide-labeled cells that express the IGF1R are co-localized with neural markers of the GFAP, the MAP-2, and the Neu-N, respectively.

The percentages of the co-localization of the bisbenzimide-labeled cells and the GFAP, the MAP-2, and the Neu-N in the immunofluorescence double staining assay are shown in Table 2 as follows, wherein brain tissues of the stroke-induced rats implanted the U-IGF1R$^+$ MSCs (n=8) or the brain tissues of the stroke-induced rats implanted the F-IGF1R$^+$ MSCs (n=8) are labeled by the immunofluorescence double staining assay. In Table 2, the percentages of the bisbenzimide-labeled cells co-localizing with the GFAP, the MAP-2 and the Neu-N are significantly higher in the U-IGF1R$^+$ MSCs treated rats (9.5%, 12%, and 10%, respectively) (n=8) than in the F-IGF1R$^+$ MSCs treated rats (4%, 5%, and 4%, respectively). It suggests higher levels of neurogenesis rate in the stroke-induced rats that received the U-IGF1R$^+$ MSCs treatment.

TABLE 2

| | marker | | |
|---|---|---|---|
| Cell type | Bisbenzimide/ GFAP | Bisbenzimide/ MAP-2 | Bisbenzimide/ Neu-N |
| U-IGF1R$^+$ MSCs | 9.5% | 12% | 10% |
| F-IGF1R$^+$ MSCs | 4% | 5% | 4% |

2.5 The IGF1R$^+$ MSCs Transplantation Promotes an Angiogenesis In Vivo

To determine whether the U-IGF1R$^+$ MSCs transplantation potentiates angiogenesis in the ischemic area of the stroke-induced rats, we perform the immunofluorescence double staining assay, FITC-dextran perfusion studies, and blood vessel density assays in this example.

Figure 15A:
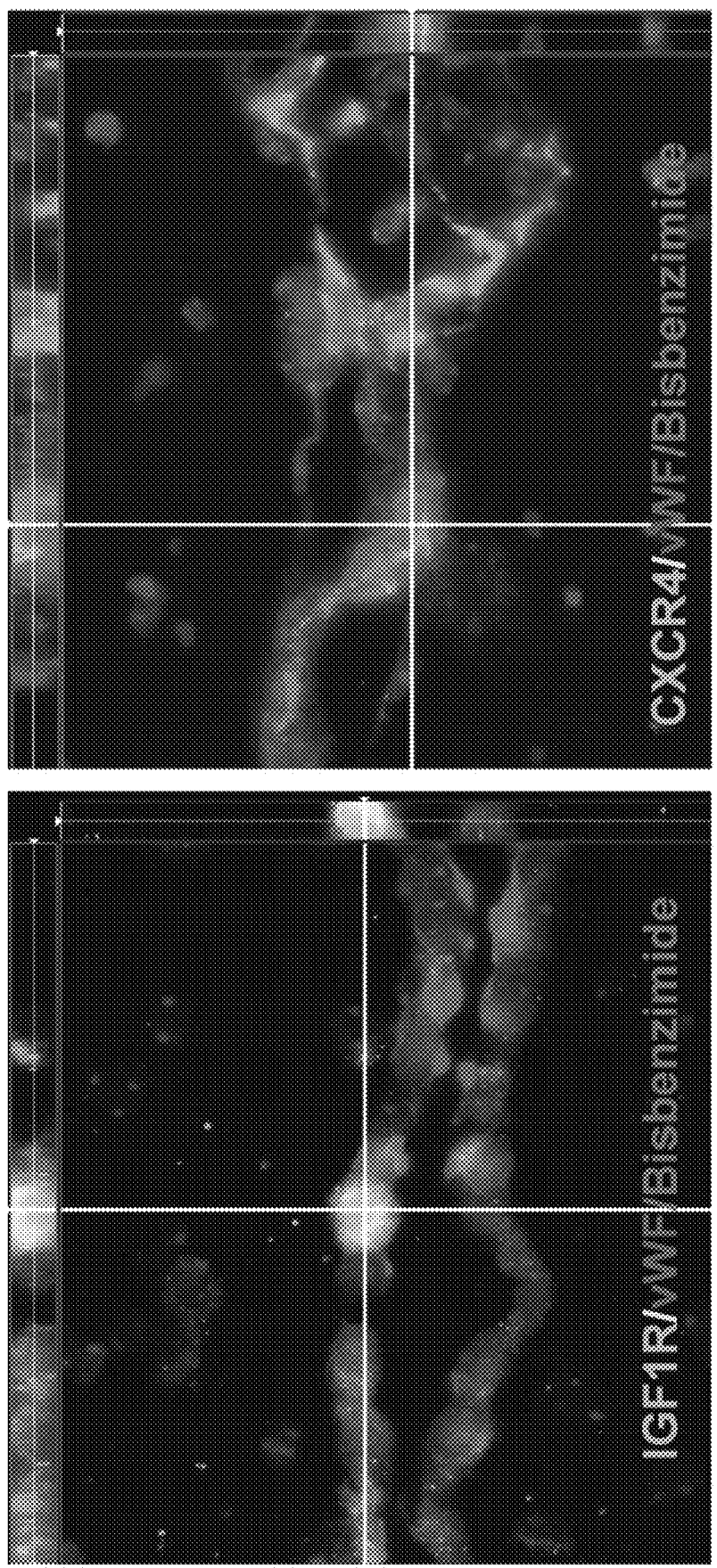
FIG. 15A is a micrograph showing that Von Willebrand factor (vWF) is co-localized with the IGF1R or the CXCR4 in the IGF1R$^+$ MSCs which are implanted into the ischemic area of the stroke-induced rats.

Brain slices of the stroke-induced rats are performed the immunofluorescence double staining assay labeling vascular endothelial cell marker Von Willebrand factor (vWF), the IGF1R and the CXCR4 to determine the co-localization of the vWF and the IGF1R, and the co-localization of the vWF and the CXCR4. The nucleus is labeled by the bisbenzimide. FIG. 15A is the micrographs showing that vWF is co-localized with the IGF1R or the CXCR4 in the IGF1R$^+$ MSCs which are implanted into the ischemic area of the stroke-induced rats. In FIG. 15A, several bisbenzimide-labeled cells co-expressing the IGF1R and the CXCR4 are co-localized with cells of vascular phenotype (vWF$^+$) in the perivascular and endothelial regions within the ischemic hemisphere of the stroke-induced rats treated with the U-IGF1R$^+$ MSCs.

Figure 15B:
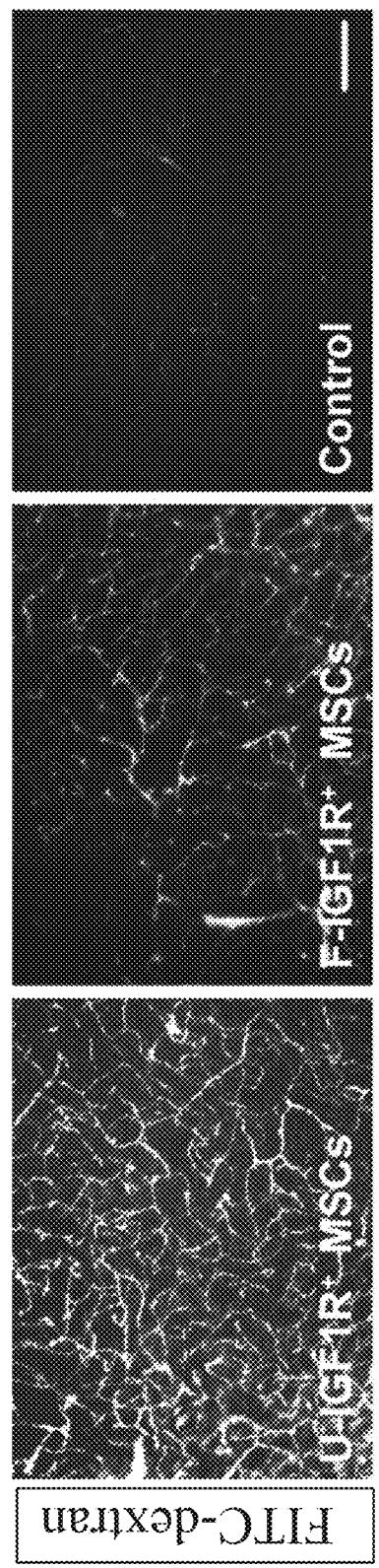
FIG. 15B shows analytical results of a FITC-dextran perfusion study in the stroke-induced rats administered with the IGF1R$^+$ MSCs treatment.

A cerebral microcirculation of the ischemic area of the stroke-induced rats is further analyzed by a FITC-dextran perfusion study in this example to determine the angiogenesis in the ischemic area of the stroke-induced rats. FIG. 15B shows the analytical results of the FITC-dextran perfusion study in the stroke-induced rats administered with the IGF1R$^+$ MSCs treatment. The rats are subdivided into three treatment groups: (1) the stroke-induced rats treated with the U-IGF1R$^+$ MSCs (n=6), (2) the stroke-induced rats treated with the F-IGF1R$^+$ MSCs (n=6), and (3) the stroke-induced rats injected with PBS as control group (n=6). In FIG. 15B, brains perfused with the FITC-dextran show significantly enhanced cerebral microvascular perfusion in the U-IGF1R$^+$ MSCs treatment group compared to the F-IGF1R$^+$ MSCs treatment group and the control group.

Figure 15C:
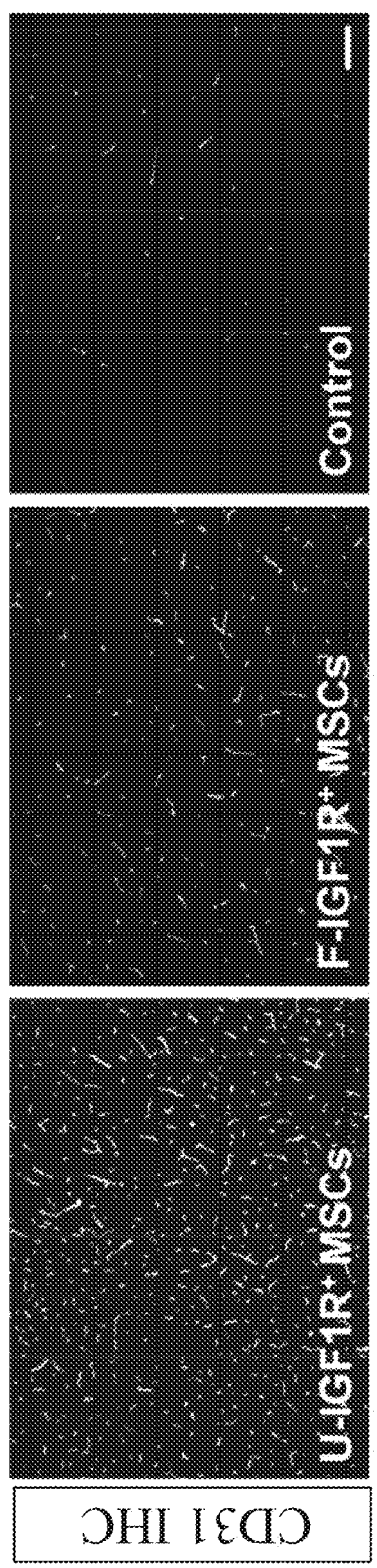
FIG. 15C shows analytical results of blood vessel density assays in the stroke-induced rats administered with the IGF1R$^+$ MSCs treatment.
Figure 15C:
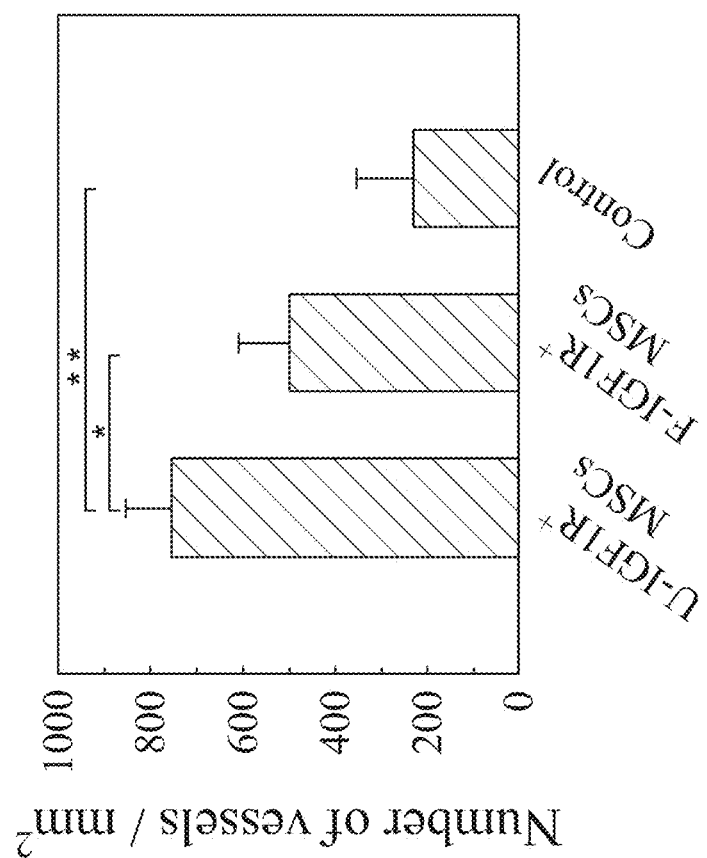

Finally, vascular endothelial cell marker CD31 in the ischemic area of the stroke-induced rats is labeled by the immunofluorescence staining assay to determine the blood vessel density. The detected groups include the stroke-induced rats treated with the U-IGF1R$^+$ MSCs (n=6), the stroke-induced rats treated with the F-IGF1R$^+$ MSCs (n=6), and the stroke-induced rats injected with the PBS as the control group (n=6). FIG. 15C shows the analytical results of the blood vessel density assays in the stroke-induced rats administered with the IGF1R$^+$ MSCs treatment. In FIG. 15C, the blood vessel density of the U-IGF1R$^+$ MSCs treatment is higher than other groups, wherein $p<0.05$ when the U-IGF1R$^+$ MSCs treatment group compares to the F-IGF1R$^+$ MSCs treatment group, and $p<0.01$ when the U-IGF1R$^+$ MSCs treatment group compares to the control group.

These results in this example suggest that the IGF1R$^+$ MSCs treatment can improve the angiogenesis in the ischemic area of the stroke-induced rats. In particular, the U-IGF1R$^+$ MSCs rather than the F-IGF1R$^+$ MSCs have superior angiogenesis potential in the ischemic area of the brain tissues.

Figure 16:
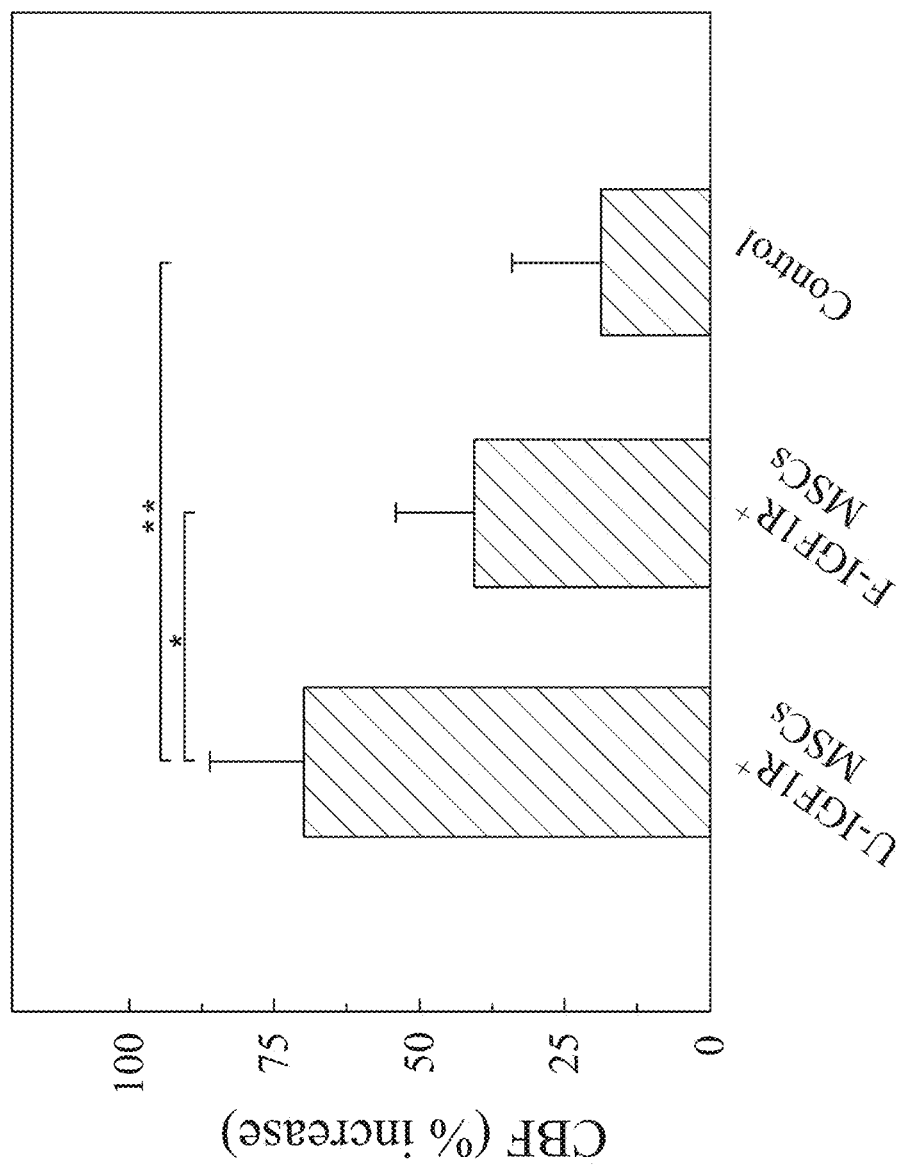
FIG. 16 shows analytical results of cerebral blood flow (CBF) in the stroke-induced rats administered with the IGF1R$^+$ MSCs treatment.

2.6 The IGF1R$^+$ MSCs Implantation Facilitates Cerebral Blood Flow (CBF) in the Ischemic Brain Increased blood vessel density is often associated with an increased cerebral blood flow (CBF), more efficient delivery of oxygen, nutrients, and enhancing neuronal survival. Therefore, we monitor the CBF in the ischemic area of the stroke-induced rats in this example. The stroke-induced rats are anesthetized by chloral hydrate, and baseline local CBF is monitored immediately after cerebral ischemia using a laser doppler flowmeter (LDF monitor, Moor Instrutment). The detected groups include the stroke-induced rats treated with the U-IGF1R$^+$ MSCs (n=6), the stroke-induced rats treated with the F-IGF1R$^+$ MSCs (n=6), and the stroke-induced rats injected with the PBS as control group (n=6). FIG. 16 shows the analytical results of the CBF in the stroke-induced rats administered with the IGF1R$^+$ MSCs treatment. In FIG. 16, the IGF1R$^+$ MSCs treatment can increase the CBF in the ischemic area of the stroke-induced rats. Furthermore, there is significantly more CBF within the ischemic area of the stroke-induced rats in the U-IGF1R$^+$ MSCs treatment group, wherein $p<0.05$ when the U-IGF1R$^+$ MSCs treatment group compares to the F-IGF1R$^+$ MSCs treatment group, and p<0.01 when the U-IGF1R+ MSCs treatment group compares to the control group.

2.7 Interactions of the CXCR4 and the IGF1R Modulate the IGF1R+ MSCs-Induced Neurite Regeneration In order to demonstrate whether the interaction between the IGF1R+ MSCs and neural tissue stimulated neurite outgrowth in vivo and in vitro, we quantify neurite regenerations in the ischemic area of the stroke-induced rats and in the MSCs/PCCs (primary cortical culture) co-cultures.

In the in vivo neurite regeneration test, the IGF1R+ MSCs are intravenous transplanted into the stroke-induced rats. The test groups are the U-IGF1R+ MSCs transplanted group, the F-IGF1R+ MSCs transplanted group, the blocking group, and the control group, wherein the blocking group are the stroke-induced rats transplanted the U-IGF1R+ MSCs transduced with the LV-IGF1R-sh (LV-IGF1R-sh-IGF1R+ MSCs) and the stroke-induced rats transplanted the U-IGF1R+ MSCs transduced with the LV-CXCR4-sh (LV-CXCR4-sh-IGF1R+ MSCs), and the control group is the stroke-induced rats injected with the PBS. The stroke-induced rats are sacrificed at 28 days after transplanting the IGF1R+ MSCs, and the brain tissue samples are fixed and immunostained with specific antibody against βIII-tubulin. Image analysis software (SigmaScan) is used for quantifying length of the neurite, and neurons with processes greater than twice the cell body diameter are counted as neurite-bearing cells.

Figure 17A:
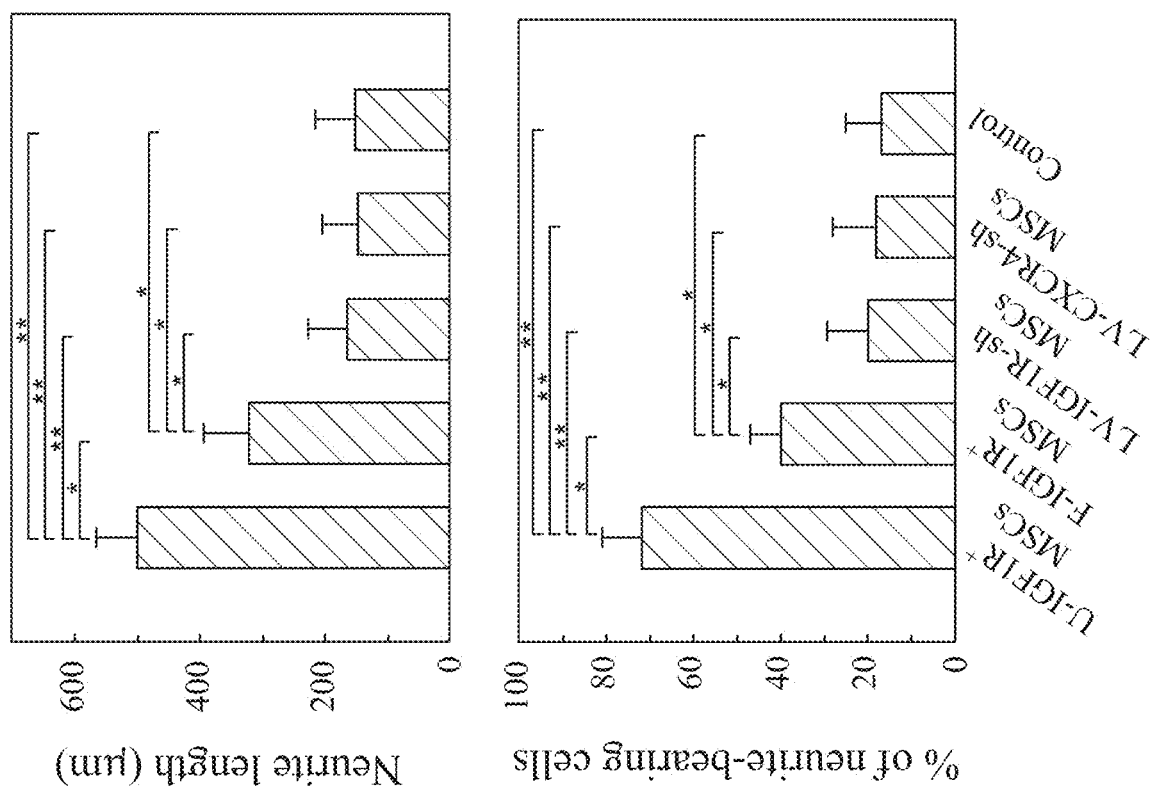
FIG. 17A shows analytical results of in vivo neurite regeneration test.
Figure 17A:
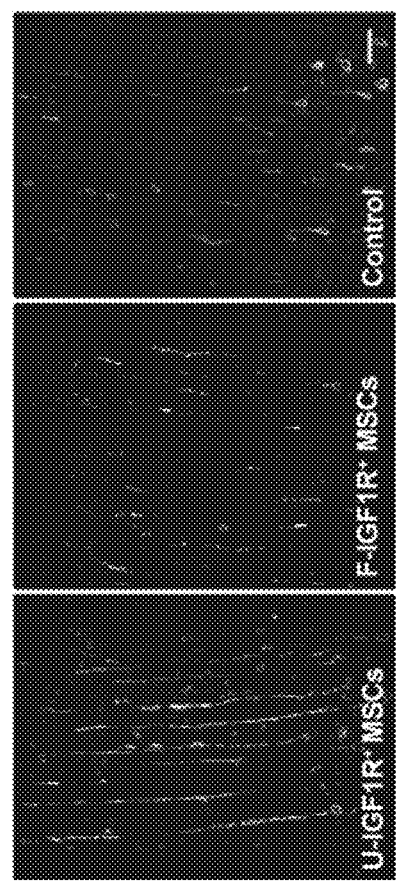

FIG. 17A shows the analytical results of the in vivo neurite regeneration test. In FIG. 17A, intravenous IGF1R+ MSCs transplantations improve the neurite regeneration in the ischemic area of the stroke-induced rats. In the U-IGF1R+ MSCs transplanted group, the number of the neurite-bearing cells is significantly higher than other groups, and the neurite length is significantly longer than other groups. However, the results of the blocking groups show that the increase in the neurite length and the number of the neurite-bearing cells are abolished following treatment with the LV-IGF1R-sh-IGF1R+ MSCs and LV-CXCR4-sh-IGF1R+ MSCs.

To evaluate whether the IGF1R+ MSCs could affect the response of the PCCs to oxygen glucose deprivation (OGD), the neurite regeneration and neuronal survival are measured in PCCs co-cultured with or without the IGF1R+ MSCs in the OGD in this example. The IGF1R+ MSCs include the U-IGF1R+ MSCs, the F-IGF1R+ MSCs, and the blocking groups, wherein cells in the blocking groups are the LV-IGF1R-sh-IGF1R+ MSCs and the LV-CXCR4-sh-IGF1R+ MSCs. The control group in this example is the PCCs alone cultured in the OGD. The co-cultured cells are fixed and immunostained with specific antibody against βIII-tubulin, and the neurite regeneration and neuronal survival are measured by aforementioned methods.

Figure 17B:
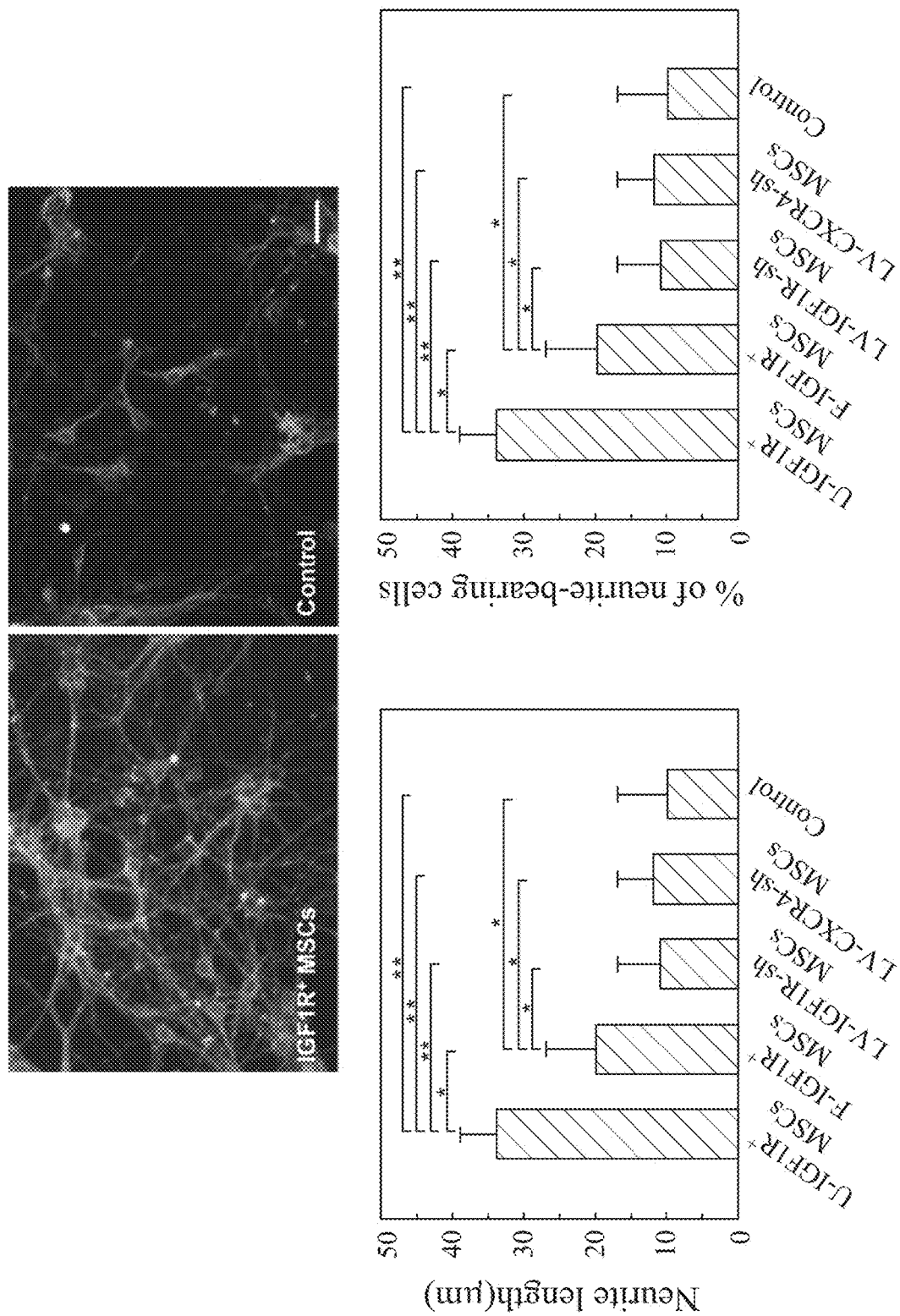
FIG. 17B shows analytical results of in vitro neurite regeneration test.

FIG. 17B shows the analytical results of the in vitro neurite regeneration test. In FIG. 17B, the IGF1R+ MSCs/PCCs co-cultures following the OGD can increase the neurite length and the number of neurite-bearing cells. It suggests that the IGF1R+ MSCs can improve the neurite regeneration of the PCCs under the OGD. In addition, the neurite length is significantly longer and more neurite-bearing cells are found in the U-IGF1R+ MSCs/PCCs co-cultures compared to the F-IGF1R+ MSCs/PCCs co-cultures and control group. Conversely, the PCCs co-cultures with the LV-IGF1R-sh-IGF1R+ MSCs or LV-CXCR4-sh-IGF1R+ MSCs show no improvement of the neurite length and the number of neurite-bearing cells.

The results of the in vivo and the in vitro neurite regeneration test indicate that the IGF1R+ MSCs can improve the neurite regeneration in the ischemic and hypoxic brain tissues or brain cells. In particular, the U-IGF1R+ MSCs have superior neurite regeneration potential in the ischemic and hypoxic brain tissues or brain cells that required the IGF1R and the CXCR4 receptor pathways.

III. The IGF1R+ MSCs Used for Treating the Ischemic Heart Disease

The data of the first part examples demonstrate that the IGF1R+ MSCs have self-renewal capability and multipotent capability, and the second part examples demonstrate that the IGF1R+ MSCs can be used for treating the brain tissue damage. In the third part examples, we further discuss the effect on the IGF1R+ MSCs used for treating the ischemic heart disease.

3.1 The IGF1R+ MSCs Treatment Attenuate the Post-MI LV Dysfunction and Reduce the Infarct Size After the MI In attempting to emphasize that IGF1R+ MSCs play a significant role in rescuing the heart from ischemic damage, we assess that in a rat model of an acute myocardial infarction (AMI) in the third part examples.

The rats are subjected to AMI by ligation of left anterior descending (LAD) coronary artery to simulate transient cardiac ischemia symptoms in the rats. The test animals are male Sprague-Dawley (SD) rats weighing 225-275 g. In brief, after induction of anaesthesia with 2% isoflurane in 100% oxygen, the rats receive artificial ventilation using a respirator (SN-480-7) with a tidal volume of 1 mL/100 g and respiratory rate 80/min. A left thoracotomy is performed in the 4-5th intercostal space using a rib retractor (MY-9454S), and the left lung is deflated using a small piece of gauze soaked in saline. The pericardium is then removed and an intra-myocardial ligature places 1-2 mm below the atrioventricular groove using a 6-O polyethylene suture needle with thread (Ethicon). When ligation area becomes white and T-wave of an electrocardiogram great rise, lungs are then re-inflated before the thorax is closed. The AMI-induced rats are then subdivided into three treated groups and injected intravenously with MSCs ($2\times10^6$ cells), IGF1R+ MSCs ($2\times10^6$ cells) or saline as the control group post-MI immediately. Sham rats undergo the same protocol with the exception of the ligation of the coronary artery.

Figure 18:
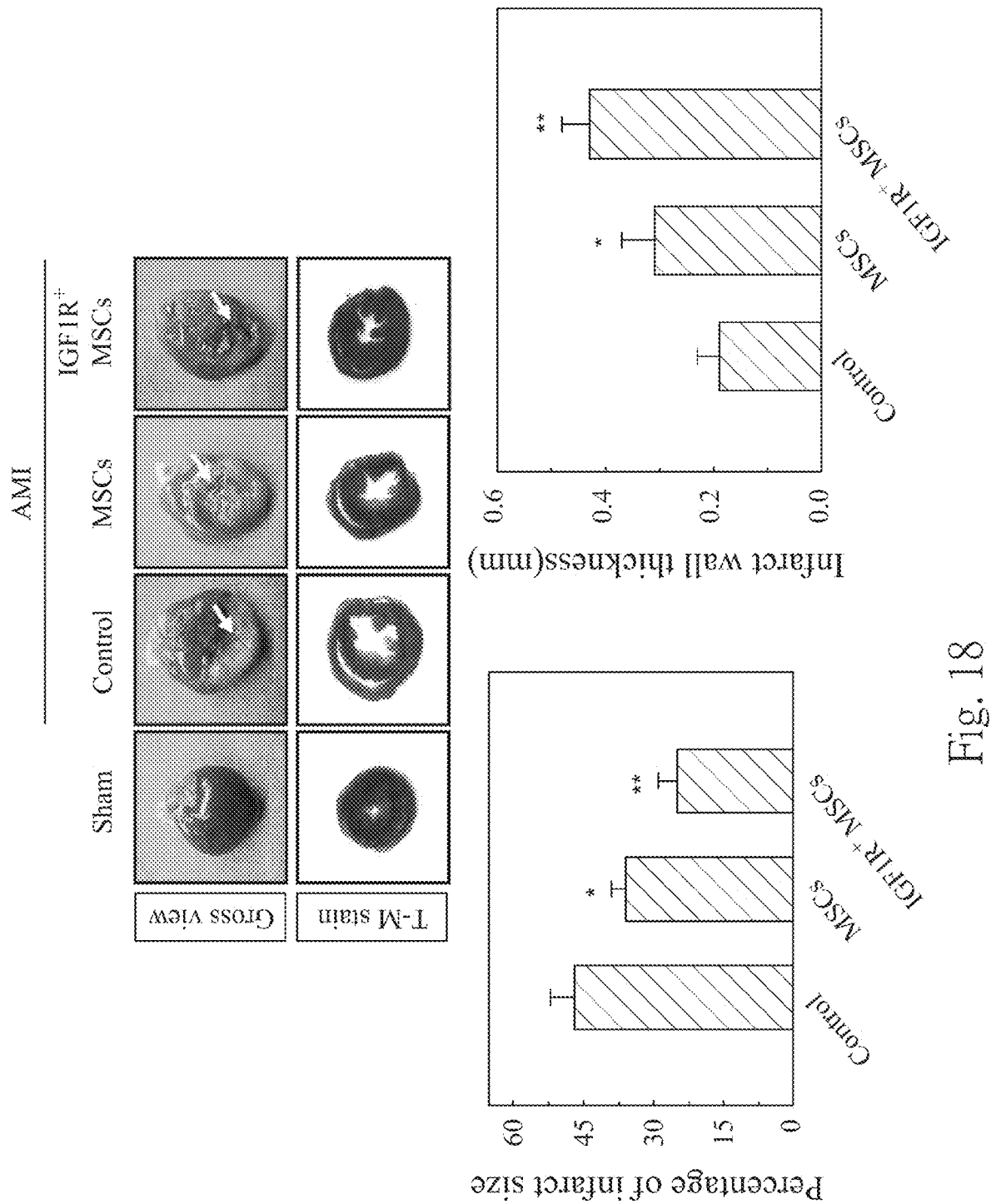
FIG. 18 is a photograph showing a myocardial infarction (MI) area in acute myocardial infarction (AMI) induced rats treated with the IGF1R$^+$ MSCs.

FIG. 18 is a photograph showing a MI area in the AMI-induced rats treated with IGF1R+ MSCs. The AMI-induced rats are sacrificed at 28 days after transplanting the IGF1R+ MSCs or the MSCs. Heart tissue samples are soaked in triphenyltetrazolium chloride, and then soaked in dehydrogenase, wherein the MI area is stained red-blue, and healthy viable heart muscle is stained deep red. In FIG. 18, the MSCs treatment and the IGF1R+ MSCs treatment can reduce the infarct size and increase a thickness of an infarct arterial wall in the AMI-induced rats. In addition, the infarct size of the IGF1R+ MSC-treated group is much smaller than the infarct size in the MSC-treated group and the control group, and the thickness of infarct arterial wall of the IGF1R+ MSC-treated group is much thicker than the thickness of infarct arterial wall in the MSC-treated group and the control group.

Figure 19A:
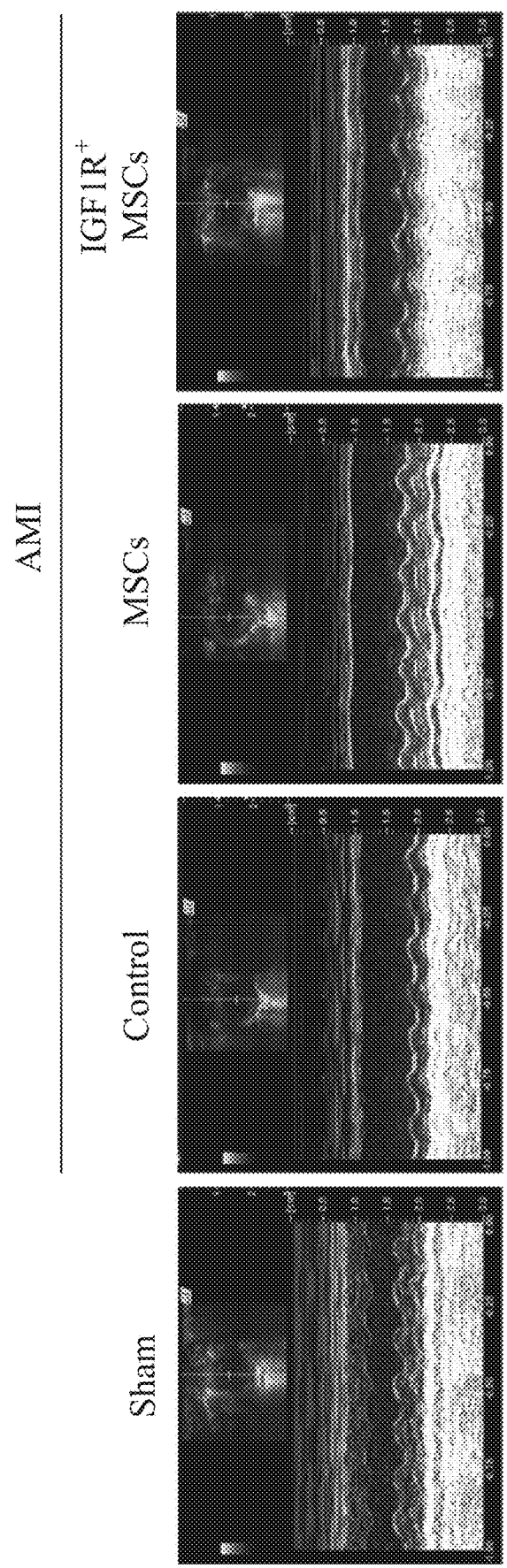
FIG. 19A is a transthoracic echocardiogram of the AMI-induced rats treated with the IGF1R$^+$ MSCs.
Figure 19B:
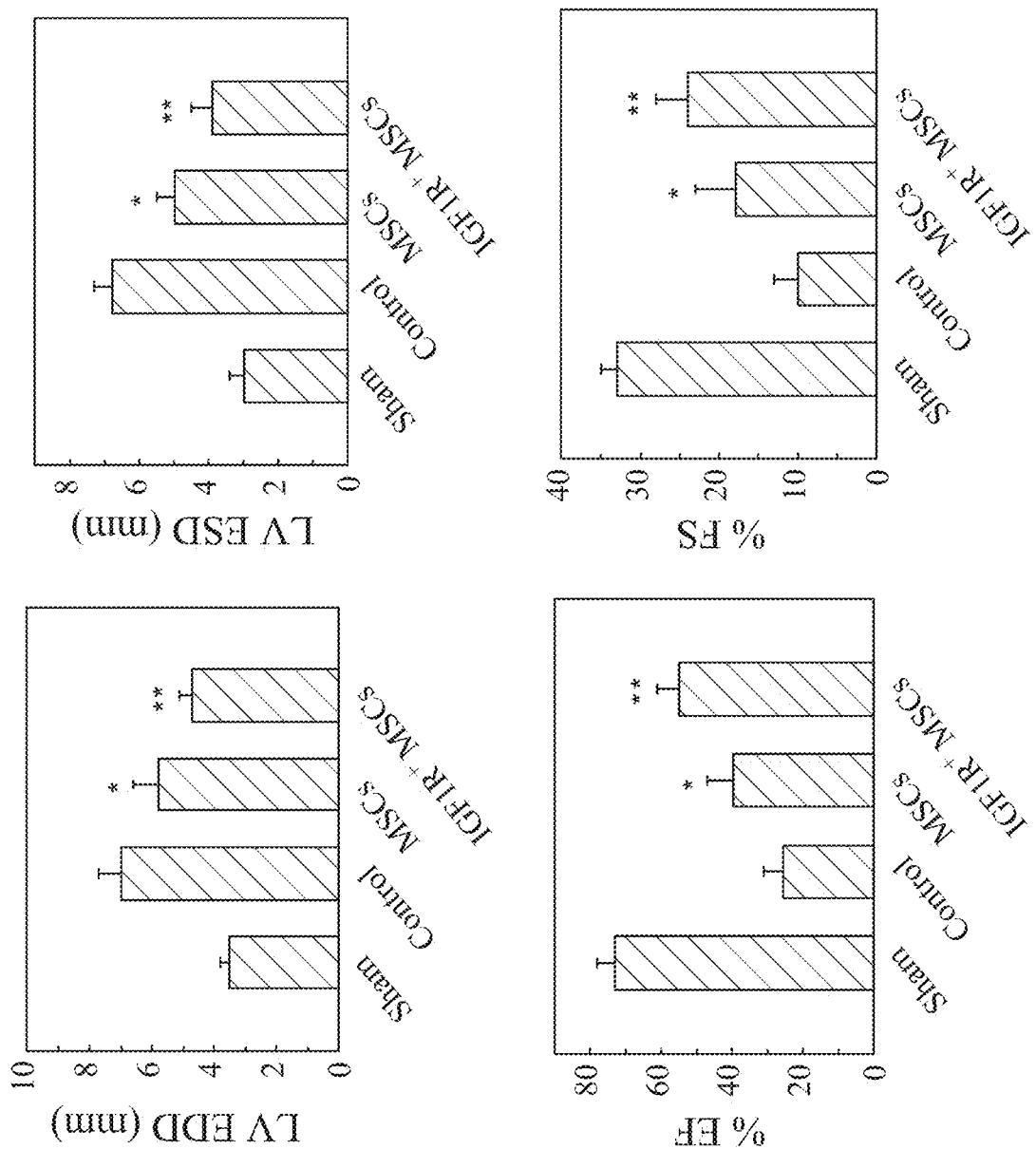
FIG. 19B is a quantitative diagram of the transthoracic echocardiogram of the AMI-induced rats treated with the IGF1R$^+$ MSCs.

M-mode tracing of echocardiography is further performed for LV function assessment at 28 days post-MI to determine the effect on the IGF1R+ MSCs used for treating the ischemic heart disease in this example. The assessed groups include the AMI-induced rats treated with the MSCs, the AMI-induced rats treated with the IGF1R+ MSCs, the control group, and the sham rats. FIG. 19A is a transthoracic echocardiogram of the AMI-induced rats treated with the IGF1R+ MSCs. FIG. 19B is a quantitative diagram of the transthoracic echocardiogram of the AMI-induced rats treated with the IGF1R+ MSCs. In FIGS. 19A and 19B, the transthoracic echocardiogram results show lower left ventricular end systolic diameter (LVESD)/left ventricular end diastolic diameter (LVEDD) and higher fraction shortening (FS)/ejection fraction (EF) in the IGF1R+ MSCs treatment group and the MSCs treatment group than that of the control group at 28 days post-MI, but not influence of the heart rates among the groups. It indicates that the IGF1R+ MSCs treatment and the MSCs treatment can improve cardiac function in the AMI-induced rats. In addition, improvement of the cardiac function of the AMI-induced rats in the IGF1R+ MSCs treatment group is greater than other groups.

3.2 Anti-Inflammatory Effect of the IGF1R+ MSCs on Ischemic Myocardium

To further examine whether the MSCs treatment and the IGF1R+ MSCs treatment suppress an inflammatory response post-MI in the AMI-induced rats, we perform an immunohistochemical analysis for studying the inflammatory cell infiltration, the immunofluorescence staining assay for detecting the expressions of macrophages, and the qRT-PCR for detecting the expression of various pro-inflammatory factors in the heart tissue of the AMI-induced rats, wherein the AMI-induced rats are sacrificed at 3 days after the MSCs treatment and the IGF1R+ MSCs treatment.

Figure 20:
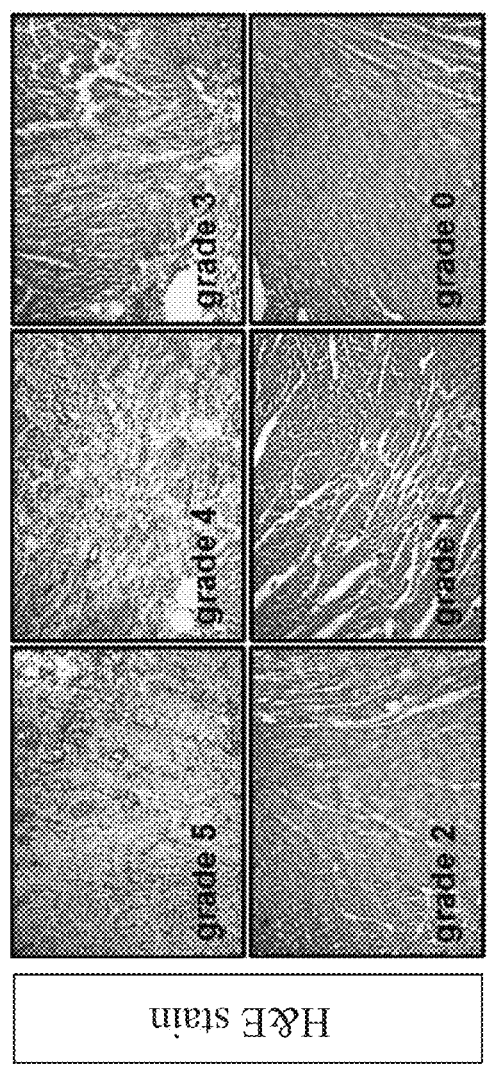
FIG. 20 shows analytical results of an immunohistochemical analysis in the AMI-induced rats at 3 days after the IGF1R$^+$ MSCs treatment.
Figure 20:
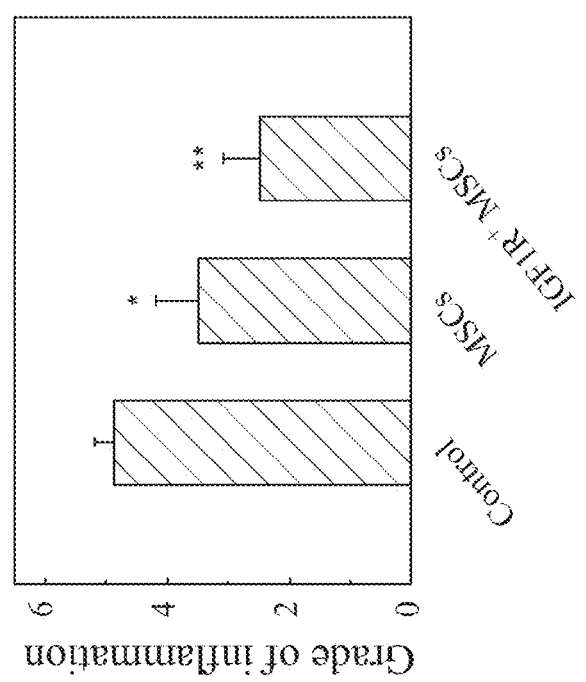

FIG. 20 shows the analytical results of the immunohistochemical analysis in the AMI-induced rats at 3 days after the IGF1R+ MSCs treatment. In FIG. 20, upper figures are the micrographs of hematoxylin and eosin (H&E) stain in heart tissue slices of the AMI-induced rats. According to the results of the immunohistochemical analysis, inflammatory conditions of the heart tissue are categorized into six grades (0, 1, 2, 3, 4, or 5), and the higher grade represents more severe inflammation. The results taken from different treated groups are classified according to the above criteria and then gathered statistics. The statistic result is shown in lower figure of the FIG. 20. In FIG. 20, the MSCs treatment and the IGF1R+ MSCs treatment reduce the inflammation in the heart tissues of the AMI-induced rats. Furthermore, significant reduction of the inflammation is observed in the IGF1R+ MSCs treatment group compared to the MSCs treatment and control group, wherein $p<0.05$ when the MSCs treatment group compares to the control group, and $p<0.01$ when the IGF1R+ MSCs treatment group compares to the control group.

Figure 21:
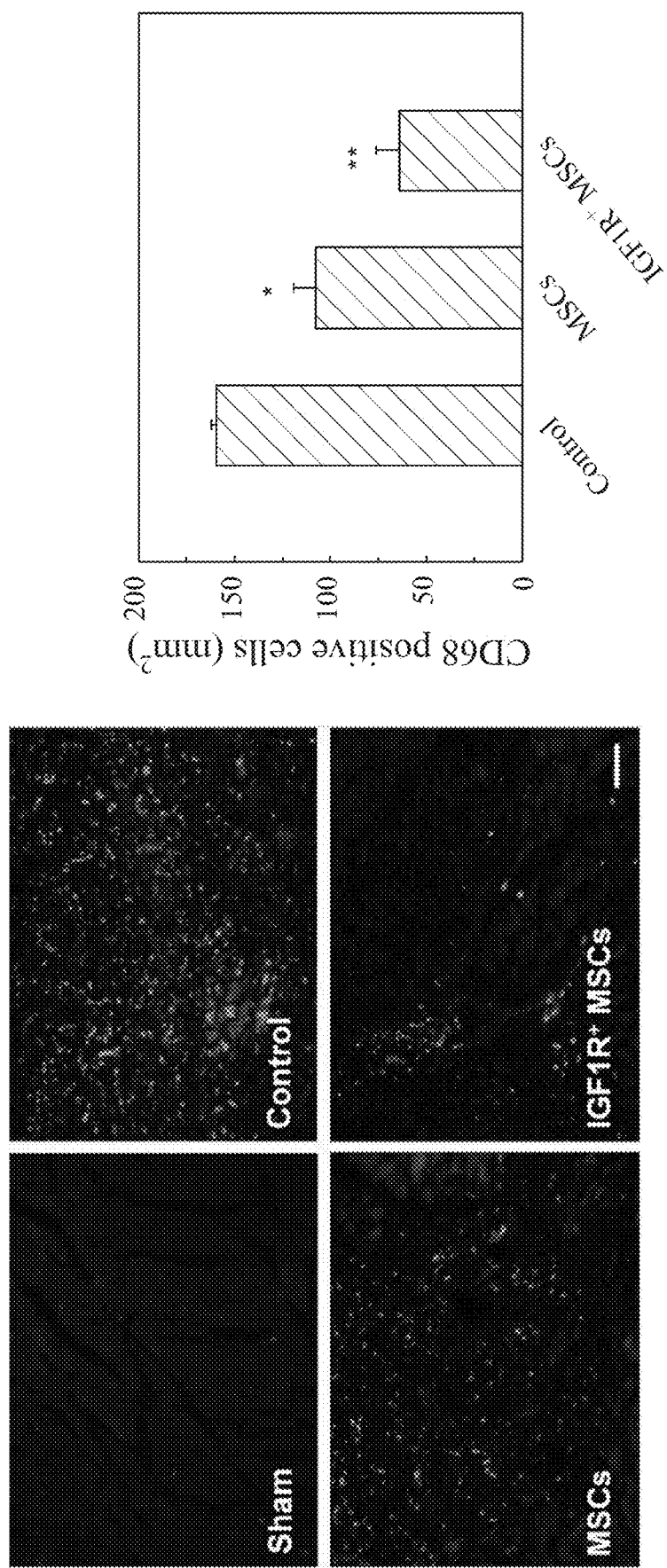
FIG. 21 shows analytical results of the immunofluorescence staining assay in the AMI-induced rats at 3 days after the IGF1R$^+$ MSCs treatment.

To further detect the expression of the macrophages in the AMI-induced rats treated with the MSCs or the IGF1R+ MSCs at 3 days after the MSCs treatment and the IGF1R+ MSCs treatment, we perform the immunofluorescence staining assay labeling a macrophage marker CD68 in the heart tissue slice of the AMI-induced rats, and the results are observed by using a fluorescent microscope. FIG. 21 shows the analytical results of the immunofluorescence staining assay in the AMI-induced rats at 3 days after the IGF1R+ MSCs treatment or the MSCs treatment. In FIG. 21, fewer CD68+ cells are infiltrated at the peri-infarct area at 3 days after the MI in the MSC treatment group or the IGF1R+ MSC treatment group than that of the control group. In addition, the IGF1R+ MSC treatment group shows significantly less expression of the CD68+ cells than the MSCs treatment group and the control group. It indicates that the IGF1R+ MSC treatment can greatly improve the inflammatory condition in the heart tissue of the AMI-induced rats.

Figure 22:
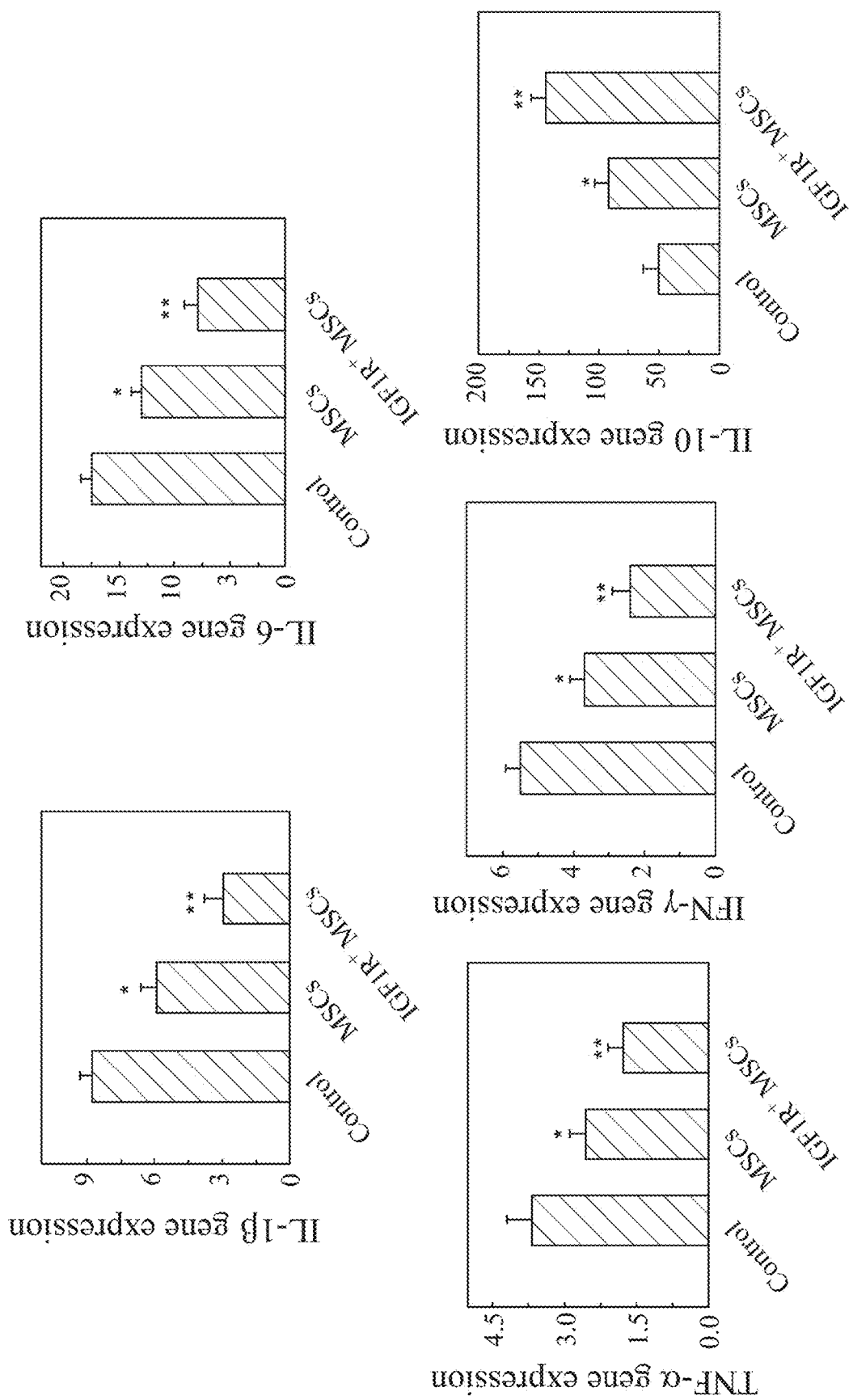
FIG. 22 shows analytical results of the expressions of pro-inflammatory factors in the AMI-induced rats at 3 days after the IGF1R$^+$ MSCs treatment.

Increased expression of proinflammatory cytokines are usually observed with many inflammatory cells infiltration in the ischemic myocardium. Quantitative RT-PCR is performed for assessing expressions of various pro-inflammatory factors in the AMI-induced rats at 3 days post-MI. The detected pro-inflammatory factors are IL-1β, IL-6, TNF-α, and INF-γ. The expression of anti-inflammatory factor IL-10 is also detected in this example. FIG. 22 shows the analytical results of the expression of pro-inflammatory factors in the AMI-induced rats at 3 days after the IGF1R+ MSCs treatment. In FIG. 22, the expression of the pro-inflammatory factors of IL-1β, IL-6, TNF-α, and INF-γ are decreased in the heart tissues at 3 days post-MI of the AMI-induced rats treated with the MSCs or the IGF1R+ MSCs. In particular, mRNA expression levels of the pro-inflammatory factors of IL-1β, IL-6, TNF-α, and INF-γ are significantly reduced in the IGF1R+ MSC treatment group compared to the MSCs treatment group and the control group. In contrast, the expression of the anti-inflammatory factor IL-10 is increased in the MSCs treatment group and the IGF1R+ MSCs treatment group. In particular, significant increase level of IL-10 is found in the IGF1R+ MSC treatment group. It suggests that the IGF1R+ MSC treatment can greatly improve the inflammatory condition in the heart tissue of the AMI-induced rats.

3.3 The IGF1R+ MSCs Treatment Attenuate the MI-Induced Fibrosis

Myocardial fibers are different from muscle fibers, the myocardial fibers can work long hours to pump blood into every part of a body. The myocardial fibers will produce irreversible necrosis after the MI. The necrosis part is replaced with fibrous tissue, and then fibrosis is generated in a few weeks. To examine whether the IGF1R+ MSCs treatment could attenuate the MI-induced fibrosis, we perform a Masson's trichrome stain for studying fibrosis conditions in the heart tissue of the AMI-induced rats, wherein the AMI-induced rats are sacrificed at 28 days after the MSCs treatment and the IGF1R+ MSCs treatment. In the Masson's trichrome stain, collagen fibers are stained blue, and muscle fibers are stained red. The analyzed groups include the AMI-induced rats treated with the MSCs, the AMI-induced rats treated with the IGF1R+ MSCs, the control group, and the sham rats.

Figure 23:
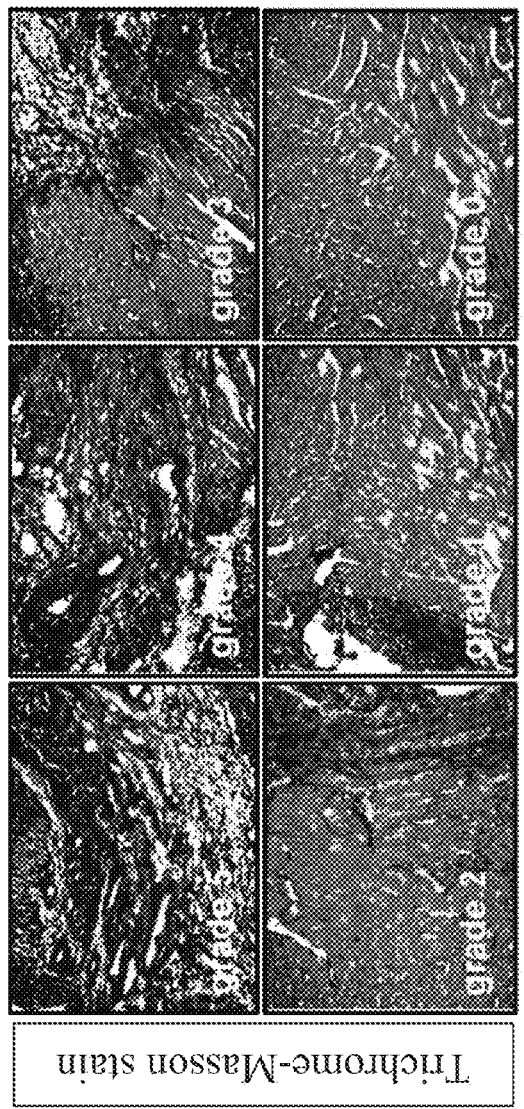
FIG. 23 shows analytical results of a Masson's trichrome stain in the AMI-induced rats at 28 days after the IGF1R$^+$ MSCs treatment.
Figure 23:
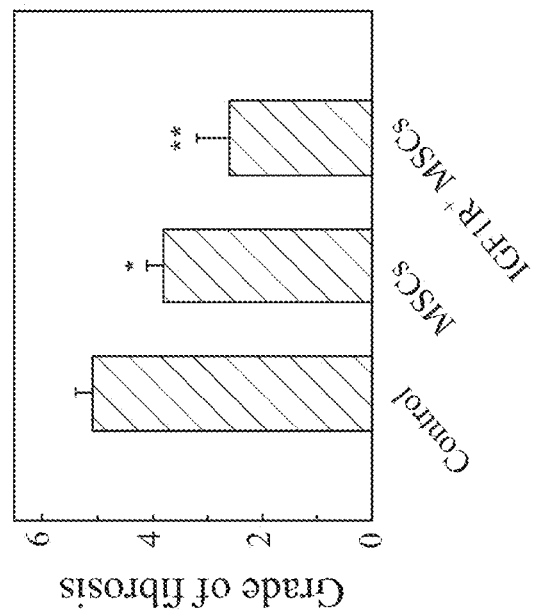

FIG. 23 shows the analytical results of the Masson's trichrome stain in the AMI-induced rats at 28 days after the IGF1R+ MSCs treatment. In FIG. 23, the upper figures are the micrographs of the Masson's trichrome stain in the heart tissue slices of the AMI-induced rats. According to the results of the Masson's trichrome stain, the fibrosis conditions of the heart tissue are categorized into six grades (0, 1, 2, 3, 4, or 5), and the higher grade represents more severe fibrosis. The results taken from different treated groups are classified according to the above criteria and then gathered statistics. The statistic result is shown in the lower figure of the FIG. 23. In FIG. 23, the MSCs treatment and the IGF1R+ MSCs treatment attenuate the fibrosis in the heart tissues of the AMI-induced rats. In particular, significantly reduced MI-induced fibrosis is observed in the IGF1R+ MSCs treatment group compared to the MSCs treatment group and the control group, wherein $p<0.05$ when the MSCs treatment group compares to the control group, and $p<0.01$ when the IGF1R$^+$ MSCs treatment group compares to the control group.

To sum up, the present disclosure provides the mesenchymal stem cell expresses the IGF1R on its cell surface (IGF1R$^+$ MSC). The IGF1R$^+$ MSC has self-renewal capability and multipotent differentiation capability. In the method for the clonogenic expansion of a plurality of IGF1R$^+$ MSCs of the present disclosure, the culture medium is containing the hUCS, wherein the hUCS is rich in growth factors, especially the PDGF-BB. The growth factors can enhance the expression of the IGF1R in the IGF1R$^+$ MSC and maintain the multipotent differentiation capability of the IGF1R$^+$ MSC. Using the medium containing the hUCS has advantages of easy obtaining easy and avoiding the risk of allergic reactions and infections of viruses or pathogens resulting from using non-human serum. The method for obtaining a plurality of multipotent MSCs of the present disclosure can screen the IGF1R positive cells, or further screen the IL22RA1 positive cells from the mammalian tissue cell mixture, wherein the screened cells are the MSCs having multipotent differentiation capability. Therefore, the method can quickly and specifically screen the multipotent MSCs. Furthermore, the IGF1R$^+$ MSC of the present disclosure can be used in the cell treatment for treating the ischemic heart disease and the brain tissue damage. In more details, for treating the brain tissue damage, the IGF1R$^+$ MSCs can increase the glucose metabolic activity of the subject, enhance the angiogenesis of the subject, and augments the neurite regeneration of the subject. The IGF1R$^+$ MSCs have the neuroplasticity effect through the IGF1R and the CXCR4 interactions. For treating the ischemic heart disease, the IGF1R$^+$ MSCs can attenuate the post-MI LV dysfunction, reduce the infarct size after the MI, reduce the fibrosis caused by the MI, and reduce the inflammatory effect on the MI.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A method for treating a brain tissue damage, the method comprising administering a composition containing a plurality of umbilical cord mesenchymal stem cells to a subject in need for a treatment of the brain tissue damage, wherein the umbilical cord mesenchymal stem cell is isolated from Wharton's jelly, and is insulin-like growth factor 1 receptor positive selected by using an insulin-like growth factor 1 receptor antibody and then cultured in a medium containing platelet-derived growth factor BB (PDGF-BB) at 2.5-50 ng/mL to enhance the expression of insulin-like growth factor 1 receptor in the mesenchymal stem cell;

wherein the brain tissue damage results from a cerebral ischemic disease.

2. The method of claim 1, wherein the cerebral ischemic disease is a stroke.

3. The method of claim 1, wherein the medium further comprises a cytokine selected from a group consisting of epidermal growth factor (EGF), angiogenin (ANG), macrophage inflammatory protein-5 (MIP-1δ), regulated on activation, normal T-cell expressed and presumably secreted (RANTES), and a combination thereof.

4. The method of claim 1, wherein a source of the PDGF-BB is human cord blood serum.

* * * * *